United States Patent
Gray et al.

(10) Patent No.: US 12,359,181 B2
(45) Date of Patent: Jul. 15, 2025

(54) OPTIMIZED GALC GENES AND EXPRESSION CASSETTES AND THEIR USE

(71) Applicants: The University of North Carolina at Chapel Hill, Chapel Hill, NC (US); The Trustees of the University of Pennsylvania, Philadelphia, PA (US)

(72) Inventors: Steven James Gray, Southlake, TX (US); Erik Lykken, Dallas, TX (US); Charles H. Vite, Philadelphia, PA (US); Allison Bradbury, Philadelphia, PA (US)

(73) Assignees: The University of North Carolina at Chapel Hill, Chapel Hill, NC (US); The Trustees of the University of Pennsylvania, Philadelphia, PA (US)

( * ) Notice: Subject to any disclaimer, the term of this patent is extended or adjusted under 35 U.S.C. 154(b) by 1041 days.

(21) Appl. No.: 17/416,559

(22) PCT Filed: Dec. 20, 2019

(86) PCT No.: PCT/US2019/067727
§ 371 (c)(1),
(2) Date: Jun. 21, 2021

(87) PCT Pub. No.: WO2020/132385
PCT Pub. Date: Jun. 25, 2020

(65) Prior Publication Data
US 2021/0395712 A1 Dec. 23, 2021

Related U.S. Application Data

(60) Provisional application No. 62/783,856, filed on Dec. 21, 2018.

(51) Int. Cl.
*A61K 48/00* (2006.01)
*A61P 25/02* (2006.01)
*C12N 9/24* (2006.01)
*C12N 15/86* (2006.01)

(52) U.S. Cl.
CPC ............ *C12N 9/2402* (2013.01); *A61P 25/02* (2018.01); *C12N 15/86* (2013.01); *C12Y 302/01046* (2013.01); *A61K 48/00* (2013.01); *C12N 2830/50* (2013.01)

(58) Field of Classification Search
CPC ....... C12N 9/2402; C12N 15/86; A61P 25/02; C12Y 302/01046
See application file for complete search history.

(56) References Cited

U.S. PATENT DOCUMENTS

| | | |
|---|---|---|
| 4,501,729 A | 2/1985 | Boucher et al. |
| 5,399,346 A | 3/1995 | Anderson et al. |
| 5,478,745 A | 12/1995 | Samulski et al. |
| 6,040,183 A | 3/2000 | Ferrari et al. |
| 6,093,570 A | 7/2000 | Ferrari et al. |
| 6,156,303 A | 12/2000 | Russell et al. |
| 7,201,898 B2 | 4/2007 | Monahan et al. |
| 9,636,370 B2 | 5/2017 | McCown et al. |
| 2014/0221465 A1 | 8/2014 | Bancel et al. |
| 2017/0360960 A1 | 12/2017 | Gray et al. |

FOREIGN PATENT DOCUMENTS

| | | |
|---|---|---|
| WO | 9811244 A2 | 3/1998 |
| WO | 9961601 A2 | 12/1999 |
| WO | 0017377 A2 | 3/2000 |
| WO | 0028004 A1 | 5/2000 |
| WO | 0028061 A2 | 5/2000 |
| WO | 0191803 A2 | 12/2001 |
| WO | 0192551 A2 | 12/2001 |
| WO | 2018136710 A1 | 7/2018 |
| WO | 2019169004 A1 | 9/2019 |

OTHER PUBLICATIONS

Chen et al. "Cloning and expression of cDNA encoding human galactocerebrosidase, the enzyme deficient in globoid cell leukodystrophy" Human Molecular Genetics, 2(11):1841-1845 (1993).
International Search Report and the Written Opinion of the International Searching Authority corresponding to International Patent Application No. PCT/US2019/067727 (14 pages) (mailed May 1, 2020).
Ungari et al. "Design of a regulated lentiviral vector for hematopoietic stem cell gene therapy of globoid cell leukodystrophy" Molecular Therapy—Methods & Clinical Development, 2(15038):1-10 (2015).
Victoria et al. "Cloning of the Canine GALC cDNA and Identification of the Mutation Causing Globoid Cell Leukodystrophy in West Highland White and Cairn Terriers" Genomics, 33:457-462 (1996).
Abdelhalim et al. "Patterns of Magnetic Resonance Imaging Abnormalities in Symptomatic Patients With Krabbe Disease Correspond to Phenotype" Pediatric Neurology, 50:127-134 (2014).
Aldenhoven et al. "Cord blood is the optimal graft source for the treatment of pediatric patients with lysosomal storage diseases: clinical outcomes and future directions" Cytotherapy, 17(6):765-774 (2015).
Allewelt et al. "Long-Term Functional Outcomes after Hematopoietic Stem Cell Transplant for Early Infantile KrabbeDisease" Biology of Blood and Marrow Transplantation, 24:2233-2238 (2018).

(Continued)

*Primary Examiner* — Evelyn Y Pyla
*Assistant Examiner* — Katherine R Small
(74) *Attorney, Agent, or Firm* — Myers Bigel, P.A.

(57) ABSTRACT

This invention relates to polynucleotides comprising optimized GALC open reading frame (ORF) sequences, vectors comprising the same, and methods of using the same for delivery of the ORF to a cell or a subject and to treat disorders associated with aberrant expression of a GALC gene or aberrant activity of a GALC gene product in the subject, such as Krabbe disease (i.e., globoid cell leukodystrophy (GLD)).

26 Claims, 6 Drawing Sheets
Specification includes a Sequence Listing.

(56) References Cited

OTHER PUBLICATIONS

Bascou et al. "A prospective natural history study of Krabbe disease in a patient cohort with onset between 6 months and 3 years of life" Orphanet Journal of Rare Diseases, 13:126 (2018).
Bonkowsky et al. "Scope and Burden of Non-Standard of Care Hematopoietic Stem Cell Transplantation in Pediatric Leukodystrophy Patients" Journal of Child Neurology, 33(14):882-887 (2018).
Bradbury et al. "AAVrh10 Gene Therapy Ameliorates Central and Peripheral Nervous System Disease in Canine Globoid Cell Leukodystrophy (Krabbe Disease)" Human Gene Therapy, 29(7):785-801 (2018).
Bradbury et al. "Clinical, electrophysiological, and biochemical markers of peripheral and central nervous system disease in canine globoid cell leukodystrophy (Krabbe disease)" Journal of Neuroscience Research, 94(11):1007-1017 (2016).
Bradbury et al. "Diffusion tensor imaging analysis of the brain in the canine model of Krabbe disease" The Neuroradiology Journal, 29(6):417-424 (2016).
Chao et al. "Several Log Increase in Therapeutic Transgene Delivery by Distinct Adeno-Associated Viral Serotype Vectors" Molecular Therapy, 2(6):619-623 (2000).
Chuang et al. "Determination of psychosine concentration in dried blood spots from newborns that were identified via newborn screening to be at risk for Krabbe disease" Clinica Chimica Acta, 419:73-76 (2013).
Conway et al. "High-titer recombinant adeno-associated virus production utilizing a recombinant herpes simplex virus type I vector expressing AAV-2 Rep and Cap" Gene Therapy, 6:986-993 (1999).
Escolar et al. "A staging system for infantile Krabbe disease to predict outcome after unrelated umbilical cord blood transplantation" Pediatrics 118(3):e879-889 (2006).
Escolar et al. "Neurodevelopmental outcomes of children with infantile Krabbe disease treated with umbilical cord blood transplantation: 10 years of follow up" CML: Lysosomal Storage Disease, 6(3):72-79 (2006).
Escolar et al. "Psychosine, a marker of Krabbe phenotype and treatment effect" Molecular Genetics and Metabolism, 121(3):271-278 (2017).
Escolar et al. "Transplantation of Umbilical Cord Blood in Babies with Infantile Krabbe's Disease" New England Journal of Medicine, 352(20):2069-2081 (2005).
Gao et al. "Clades of Adeno-Associated Viruses Are Widely Disseminated in Human Tissues" Journal of Virology, 78(12):6381-6388 (2004).
International Preliminary Report on Patentability corresponding to International Patent Application No. PCT/US2019/067727 (8 pages) (dated Jun. 16, 2021).
Karumuthil-Melethil et al. "Intrathecal Administration of AAV/GALC Vectors in 10-11 Day old Twitcher Mice Improves Survival and is Enhanced by Bone Marrow Transplant" Journal of Neuroscience Research, 94(11):1138-1151 (2016).
Kobayashi et al. "The Twitcher mouse: an enzymatically authentic model of human globoid cell leukodystrophy (Krabbe disease)" Brain Research, 202:479-483 (1980).
Krivit et al. "Hematopoietic stem-cell transplantation in globoid-cell leukodystrophy" The New England Journal of Medicine, 338(16):1119-1126 (1998).
Kwon et al. "Consensus guidelines for newborn screening, diagnosis and treatment of infantile Krabbe disease" Orphanet Journal of Rare Diseases, 13:30 (2018).
Li et al. "Quantitative DTI metrics in a canine model of Krabbe disease: comparisons versus age-matched controls across multiple ages" The Neuroradiology Journal, 31(2):168-176 (2018).
Liao et al. "Lymphocyte Galactocerebrosidase Activity by Liquid Chromatography-Tandem Mass Spectrometry for Post-Newborn Screening Evaluation of Krabbe Disease" Clinical Chemistry, 63(8):1363-1369 (2017).
Lim et al. "Sustained neurological improvement following reduced-intensity conditioning allogeneic haematopoietic stem cell transplantation for late-onset Krabbe disease" Bone Marrow Transplantation, 41(9):831-832 (2008).
Margolskee, R. F. "Epstein-Barr Virus Based Expression Vectors" Current Topics in Microbiology and Immunology, 158:67-95 (1992).
Marshall et al. "Long-Term Improvement of Neurological Signs and Metabolic Dysfunction in a Mouse Model of Krabbe's Disease after Global Gene Therapy" Molecular Therapy, 26(3):874-889 (2018).
McGowan et al. "Investigating Demyelination in the Brain in a Canine Model of Globoid Cell Leukodystrophy (Krabbe Disease) Using Magnetization Transfer Contrast: Preliminary Results" Journal of Computer Assisted Tomography, 24(2):316-321 (2000).
Moser, Hugo W. "Peripheral nerve involvement in Krabbe disease: A guide to therapy selection and evaluation" Neurology, 67(2):201-202 (2006).
Musolino et al. "Hematopoietic Stem Cell Transplantation in the Leukodystrophies: A Systematic Review of the Literature" Neuropediatrics, 45(3):169-174 (2014).
Palombo et al. "Site-Specific Integration in Mammalian Cells Mediated by a New Hybrid Baculovirus-Adeno-Associated Virus Vector" Journal of Virology, 72(6):5025-5034 (1998).
Prasad et al. "Unrelated donor umbilical cord blood transplantation for inherited metabolic disorders in 159 pediatric patients from a single center: influence of cellular composition of the graft on transplantation outcomes" Blood, 112(7):2979-2989 (2008).
Shapiro et al. "Neuropsychological outcomes of several storage diseases with and without bone marrow transplantation" Journal of Inherited Metabolic Disease, 18(4):413-429 (1995).
Shin et al. "Altered Trafficking and Processing of GALC Mutants Correlates with Globoid Cell Leukodystrophy Severity" The Journal of Neuroscience, 36(6):1858-1870 (2016).
Siddiqi et al. "Peripheral neuropathy in Krabbe disease: effect of hematopoietic stem cell transplantation" Neurology, 67:263-267 (2006).
Syed et al. "Central Nervous System Complications of Hematopoietic Stem Cell Transplant" Hematology/Oncology Clinics of North America, 30(4):887-898 (2016).
Turgeon et al. "Measurement of psychosine in dried blood spots—a possible improvement to newborn screening programs for Krabbe disease" Journal of Inherited Metabolic Disease, 38(5):923-929 (2015).
Tyle, Praveen "Iontophoretic Devices for Drug Delivery" Pharmaceutical Research, 3(6):318-326 (1986).
Vite et al. "Correlating magnetic resonance findings with neuropathology and clinical signs in dogs and cats" Veterinary Radiology & Ultrasound, 52(1 Suppl. 1):S23-S31 (2011).
Weimer et al. "Serial Electrophysiologic Studies in Rhesus Monkeys with Krabbe Disease" Muscle & Nerve 32:185-190 (2005).
Wenger et al. "Globoid Cell Leukodystrophy in Cairn and West Highland White Terriers" Journal of Heredity, 90(1):138-142 (1999).
Wenger et al. "Krabbe disease: One Hundred years from the bedside to the bench to the bedside" Journal of Neuroscience Research, 94(11):982-989 (2016).
Wright et al. "Developmental outcomes of cord blood transplantation for Krabbe disease: A 15-year study" Neurology, 89(13):1365-1372 (2017).
Zhang et al. "Recombinant adenovirus expressing adeno-associated virus cap and rep proteins supports production of hightiter recombinant adeno-associated virus" Gene Therapy, 8:704-712 (2001).
Zolotukhin et al. "Recombinant adeno-associated virus purification using novel methods improves infectious titer and yield" Gene Therapy, 6:973-985 (1999).
Extended European Search Report corresponding to European Patent Application No. 19899126.7 (11 pages) (dated Aug. 10, 2022).
Malin Parmar "Addgene: 1000.pCCLsin.cPPT.hPGK.Ascl1.WPRE" Addgene Website, pp. 1-4 (2014).
Rafi et al. "Long-term Improvements in Lifespan and Pathology in CNS and PNS After BMT Plus One Intravenous Injection of AAVrh10-GALC in Twitcher Mice" Molecular Therapy, 23(11):1681-1690 (2015).

FIG. 1

```
RATTUS  YELDDSDGLGLEFDGIGAVSGGGATSRLLVNYPEPYRSEILDYLFKPNFGASLHILKVEI
MUS     YVLDDSDGLGREFDGIGAVSGGGATSRLLVNYPEPYRSEILDYLFKPNFGASLHILKVEI
CANIS   YVLDDSDGLGREFDGVGAVSGGGATSRLLVNYPEPYRSQILDYLFKPNFGASLHILKVEI
hGALC   YVLDDSDGLGREFDGIGAVSGGGATSRLLVNYPEPYRSQILDYLFKPNFGASLHILKVEI
MACACA  YVLDDSDGLGREFDGIGAVSGGGATSRLLVNYPEPYRSQILDYLFKPNFGASLHILKVEI
        * ******** ****:*********************:**********************

RATTUS  GGDGQTTDGTEPSHMHYELDENYFRGYEWWLMKEAKKRNPNIILMGLPWSFPGWLGKGFS
MUS     GGDGQTTDGTEPSHMHYELDENYFRGYEWWLMKEAKKRNPDIILMGLPWSFPGWLGKGFS
CANIS   GGDGQTTDGTEPSHMHYALDENFFRGYEWWLMKEAKKRNPNIILMGLPWSFPGWIGKGFN
hGALC   GGDGQTTDGTEPSHMHYALDENYFRGYEWWLMKEAKKRNPNITLIGLPWSFPGWLGKGFD
MACACA  GGDGQTTDGTEPSHMHYALDENYFRGYEWWLMKEAKKRNPNITLIGLPWSFPGWLGKGFD
        ***************** **** :*****************:* *:**********:***.

RATTUS  WPYVNLQLTAFYIVRWILGAKHYHDLDIDYIGIWNERPFDANYIKELRKMLDYEGLQRVR
MUS     WPYVNLQLTAYYVVRWILGAKHYHDLDIDYIGIWNERPFDANYIKELRKMLDYQGLQRVR
CANIS   WPYVNLQLTAYYIMTWIVGAKHYHDLDIDYIGIWNERSFDINYIKVLRRMLNYQGLDRVK
hGALC   WPYVNLQLTAYYVVTWIVGAKRYHDLDIDYIGIWNERSYNANYIKILRKMLNYQGLQRVK
MACACA  WPYVNLQLTAYYVVTWIVGAKRYHDLDIDYIGIWNERSYNANYIKILRKMLNSQGLQRVK
        **********:*:: ** :****************  :: **** **.**: :**:**:

RATTUS  IIASDNLWEPISSSVLLDQELWKVVDVIGAHYPGTYTVWNAKMSGKKLWSSEDFSTVNSN
MUS     IIASDNLWEPISSSLLLDQELWKVVDVIGAHYPGTYTVWNAKMSGKKLWSSEDFSTINSN
CANIS   IIASDNLWEPISASMLLDSELLKVIDVIGAHYPGTHTVKDAKLTKKKLWSSEDFSTLNSD
hGALC   IIASDNLWESISASMLLDAELFKVVDVIGAHYPGTHSAKDAKLTGKKLWSSEDFSTLNSD
MACACA  IIASDNLWESISAAMLLDAELFKVVDVIGAHYPGTHSVKDARLTGKKLWSSEDFSTLNSD
        ********* **::::*** ** **:********** :.  :*: :: ***********:**:

RATTUS  VGAGCWGRILNQNYINGNMTATIAWNLVASYYEELPYGRSGLMTAQEPWSGHYVVASPIW
MUS     VGAGCWSRILNQNYINGNMTSTIAWNLVASYYEELPYGRSGLMTAQEPWSGHYVVASPIW
CANIS   VGAGCLGRILNQNYVNGYMTATIAWNLVASYYEQLPYGRCGLMTAQEPWSGHYVVESPIW
hGALC   MGAGCWGRILNQNYINGYMTSTIAWNLVASYYEQLPYGRCGLMTAQEPWSGHYVVESPVW
MACACA  TGAGCWGRILNQNYVNGYMTSTIAWNLVASYYEQLPYGRCGLMTAQEPWSGHYVVESPVW
         **** .********:** **:***********:*****.***********.****** **:*

RATTUS  VSAHTTQFTQPGWYYLKTVGHLEKGGSYVALTDGLGNFTIIVETMSRQHSMCIRPYLPYY
MUS     VSAHTTQFTQPGWYYLKTVGHLEKGGSYVALTDGLGNLTIIIETMSHQHSMCIRPYLPYY
CANIS   VSAHTTQFTQPGWYYLKTVGHLEKGGSYVALTDGLGNLTIIVETMSHKQSACIRPFLPYF
hGALC   VSAHTTQFTQPGWYYLKTVGHLEKGGSYVALTDGLGNLTIIIETMSHKHSKCIRPFLPYF
MACACA  VSAHTTQFTQPGWYYLKTVGHLEKGGSYVALTDGLGNLTIIIETMSHKHSKCIRPFLPYF
        ************************************:****:****::: * :****:***:

RATTUS  NVSRQLATFILKGSLKEIQELQVWYTKLGTTPEKLHFKQLETLWLLDGSGSFSLELEEDE
MUS     NVSHQLATFTLKGSLKEIQELQVWYTKLGTPQQRLHFKQLDTLWLLDGSGSFTLELEEDE
CANIS   NVSRQFATFVLKGSFSEIPELQVWYTKLGKPSERYLFKQLDSLWLLDSSSTFTLELQEDE
hGALC   NVSQQFATFVLKGSFSEIPELQVWYTKLGKTSERFLFKQLDSLWLLDSDGSFTLSLHEDE
MACACA  NVSQQFATFVLKGSFSEIPELQVWYTKLGKTSERFLFKQLDSLWLLDSNGSFTLKLQEDE
        ***:*:**** ****::**:********:    :: :****::******:....:**. :.*.***
```

FIG. 1 (cont.)

```
RATTUS  MFTLTTLTTGHKGSYRPPPKSQPFPTSYKDDFNVEYPLFSEAPNFADQTGVFEYYTNNED
MUS     IFTLTTLTTGRKGSYPPPPSSKPFPTNYKDDFNVEYPLFSEAPNFADQTGVFEYYMNNED
CANIS   IFTLTTLTVGSKGSYPLPPKSEPFPQIYEDDFDVDYPFFSEAPNFADQTGVFEYFTNIED
hGALC   LFTLTTLTTGRKGSYPLPPKSQPFPSTYKDDFNVDYPFFSEAPNFADQTGVFEYFTNIED
MACACA  LFTLTTLTTGRKGSYLPPPKSQRFPSTYKDDFNVDYPFFSEAPNFADQTGVFEYFTNMED
        :*******.* ****   **.*: **   *:***.*:**.******************: * **

RATTUS  -LEHRFTLRQVLNQRPITWAADASSTISVIGDHHWSNMTVQCDVYIETPRTGGVFIAGRV
MUS     -REHRFTLRQVLNQRPITWAADASSTISVIGDHHWTNMTVQCDVYIETPRSGGVFIAGRV
CANIS   PGEHRFTLRQVLNQRPITWAADAYNTISIIGDYKWSNLTVRCDVYIETPEKGGVFIAGRV
hGALC   PGEHHFTLRQVLNQRPITWAADASNTISIIGDYNWTNLTTKCDVYIETPDTGGVFIAGRV
MACACA  PGEHHFTLRQVLNQRPITWAADASNTISIIGDYNWTNLTIKCDVYIETPDTGGVFIAGRV
         **:***************** .***:***::*:*:* :******* .*********

RATTUS  NKGGILIRTASGVFFWIFANGSYRVTADLGGWITYASGHADVTAKRWYTLTLGIKGYLAS
MUS     NKGGILIRSATGVFFWIFANGSYRVTADLGGWITYASGHADVTAKRWYTLTLGIKGYFAF
CANIS   NKGGILIRSARGIFFWIFANGTYRVTGDLAGWVIYALGRVDVTAKKWYTLTLIIKGRLSS
hGALC   NKGGILIRSARGIFFWIFANGSYRVTGDLAGWIIYALGRVEVTAKKWYTLTLTIKGHFAS
MACACA  NKGGILIRSARGIFFWIFANGSYRVTGDLAGWIIYALGHVEVTAKTWYTLTLTIKGRFAS
        ********:* *:*********:****.**.**: ** *:..:**** ****** ***  ::

RATTUS  GMLNGKILWENVPVKYPGHGWAAIGTHTFEFAQFDNFHVEAAR 642
MUS     GMLNGTILWKNVRVKYPGHGWAAIGTHTFEFAQFDNFRVEAAR 642
CANIS   GMLNGKTVWKNIPVSFPKNGWAAIGTHSFEFAQFDNFHVEATR 643
hGALC   GMLNDKSLWTDIPVNFPKNGWAAIGTHSFEFAQFDNFLVEATR 643
MACACA  GMLNDKSLWTDIPVNFPKNGWAAIGTHSFEFAQFDNFHVEATR 643
        ****.. :*  ::  *..:* :***********:********  ***:*
```

OPTIMIZED GALC GENES AND EXPRESSION CASSETTES AND THEIR USE

STATEMENT OF PRIORITY

This patent application is a 35 U.S.C. § 371 national phase application of PCT Application PCT/US2019/067727 filed Dec. 20, 2019, which claims the benefit, under 35 U.S.C. § 119(e), of U.S. Provisional Application No. 62/783,856, filed on Dec. 21, 2018, the entire contents of each of which are incorporated by reference herein.

STATEMENT OF GOVERNMENT SUPPORT

This invention was made with government support under Grant Number NS096087 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-861_ST25.txt, 56,774 bytes in size, generated on Jun. 14, 2021 and filed via EFS-Web, is provided in lieu of a paper copy. This Sequence Listing is hereby incorporated herein by reference into the specification for its disclosures.

FIELD OF THE INVENTION

This invention relates to polynucleotides comprising optimized GALC open reading frame (ORF) sequences, vectors comprising the same, and methods of using the same for delivery of the ORF to a cell or a subject and to treat disorders associated with aberrant expression of a GALC gene or aberrant activity of a GALC gene product in the subject, such as Krabbe disease (KD) (i.e., globoid cell leukodystrophy (GLD)).

BACKGROUND OF THE INVENTION

Krabbe disease (KD), also known as Globoid Cell Leukodystrophy (GLD), is a rapidly progressive, terminal lysosomal storage disorder caused by mutations in the GALC gene, primarily affecting the myelination of the nervous system. The GALC gene encodes a 669-amino acid, 17-exon, lysosomal enzyme galactosylceramidase (galactocerebrosidase) that catabolizes galactosylceramide (galactocerebroside), the principal glycosphingolipid of the myelin in brain tissue (Chen et al. 1993 Hum. Mol. Genet. 2(11): 1841-1845). The GALC enzyme breaks down galactocerebroside to ceramide and galactose (Ferreira and Gahl 2017 Transl. Sci. Rare Dis. 2(12):1-71). GALC deficiency leads to accumulation of the substrate in the myelin sheath of the peripheral and central nervous system. Accumulated galactocerebroside in the white matter is catabolized via an alternative pathway, resulting in high-levels of psychosine that is toxic to oligodendrocytes and Schwann cells leading to apoptosis (reviewed by Ferreira and Gahl 2017; Bascou et al. 2018 Orphanet J. Rare Dis. 13(1):126). Galactocerebroside also accumulates in the cerebral microglial macrophages which fuse to form multinucleated globoid cells. Histopathology in the CNS is characterized by cerebral atrophy, loss of myelin, gliosis and globoid cells.

Classically, KD was categorized into four subgroups based on age at presentation: 1) Early Infantile (0-5 months), 2) Late-Infantile (6-36 months), 3) Juvenile (37 months-16 years), and 4) Adult (>16 years). However, recent natural history data supports a revised classification for the Infantile sub-groups into 1) Infantile (<1=12 months) and 2) Late-Infantile (>12 months). Patients presenting within the first 12 months of life demonstrated a similar clinical severity and rate of neurodegeneration compared to those classically described as Early-Infantile (<6 months). All patients with onset of symptoms prior to 9 months and the majority of patients presenting between 9-12 months were consistent with the most severe KD-phenotype based on symptom onset, disease progression, and correlation with potential biomarkers (genotype, GALC enzyme activity, neurodevelopmental assessments, neuroimaging, and neurophysiological studies).

Psychosine is a substrate for GALC enzyme that accumulates in body fluids and tissues in the disease, and is used as a biomarker for KD. Newborn screening where dried blood spot (DBS) testing was done showed elevated psychosine levels in infants that developed infantile KD, but not in some asymptomatic patients (Chuang et al. 2013 Clin. Chim. Acta. 419:73-76; Turgeon et al. 2015 J. Inherit. Metab. Dis. 38(5):923-929). The elevated psychosine levels correlated with the enzyme activity in the lymphocytes and severity of the Krabbe disease (Liao et al. 2017 Clin. Chem. 63(8):1363-1369). All the newborns that had concentration of psychosine over 3 nmol/L in the DBS developed infantile KD (Escolar et al. 2017 Mol. Genet. Metab. 121(3):271-278). Clinical manifestations in KD exclusively impact the neuronal system. The more common and rapidly progressive form is an infantile onset associated with hypertonicity, evidenced by hyperactive reflexes early on which subsequently develop into hypotonic flaccidity, irritability, stiffness and seizures. Infantile and juvenile disease onset is associated with loss of acquired developmental milestones, motor deficits, and visual and hearing capabilities, while adult onset disease is associated with abnormal gait, seizures and peripheral neuropathy. An abnormal increase in the T2 signal on magnetic resonance imaging (MRI) in the periventricular white matter, alterations in nerve conduction velocities and increased cerebrospinal fluid protein levels are seen following onset of symptoms. Regardless of subgroup, all clinical forms experience progressive central nervous system (CNS) dysfunction with significant psychomotor functional decline with progression of neurodegeneration and myelin destruction. Infantile-KD is the most clinically severe subgroup with presentation in the first year of life and rapid neurological decline. Most Infantile-KD patients present with axial hypotonia, irritability, and loss of acquired developmental milestones. Further neurologic deterioration is rapid after the onset of symptoms in this group. Most Infantile KD patients succumb to the disease by 2 years of age.

Treatment options for KD are currently limited to hematopoietic stem cell therapy (HSCT) (Escolar et al. 2005 N. Engl. J. Med. 352(20):2069-2081; Lim et al. 2008 Bone Marrow Transplant. 41(9):831-832; Escolar et al. 2006 CML: Lysosomal Storage Disease 6(3):72-79; Escolar et al. 2006 Pediatrics 118(3):e879-889; Krivit et al. 1998 N. Engl. J. Med. 338(16):1119-1126). While HSCT is associated with some functional improvements particularly in mobility, communication and feeding (Escolar et al. 2005 N. Engl. J. Med.; Allewelt et al. 2018 Biol. Blood Marrow Transplant. S1083-8791(18)30334-3; Shapiro et al. 1995 J. Inherit. Metab. Dis. 18(4):413-429; Kwon et al. 2018 Orphanet J. Rare Dis. 13(1):30), this treatment has substantial limitations. HSCT has only shown to be effective if performed within 30 days of birth prior to the onset of disease (Allewelt et al. 2018; Kwon et al. 2018). The timing of stem cell engraftment is approximately 2 months, which is not ideal in a rapidly progressive degenerative disease. HSCT procedure itself in pediatric populations is associated with a 20% risk of mortality (Shin et al. 2016 J. Neurosci. 36(6):1858-1870; Bonkowsky et al. 2018 J. Child Neurol. 33(14):882-887). Graft-versus-host disease (GVHD), another complication of HSCT, impacted about 10% of the pediatric transplant recipients with inherited metabolic disorders (Prasad et al. 2008 Blood. 112(7):2979-2989). Further, HSCT requires a prolonged hospitalization that contributes to poorer neurodevelopmental outcomes (Syed et al. 2016 Hematol. Oncol. Clin. North Am. 30(4):887-898). Based on a meta-analysis of HSCT for leukodystrophies, complications, cause of death, and poor outcomes appear to be underreported in the published literature (Musolino et al. 2014 Neuropediatrics 45(3):169-174). Further, it is not clear whether poor outcomes are related to disease progression or are inherent to the required myeloablative procedures, which are known to cause long-term neurologic dysfunction (Syed et al. 2016). Pre-symptomatic intervention with HSCT in KD results in increased survival, but quality of life remains poor with a progressive peripheral neuropathy that is ultimately fatal (Aldenhoven and Kurtzberg 2015 Cytotherapy 17(6):765-774). In a 15-year follow-up study of 18 Infantile KD patients treated with HSCT within the first 7 weeks of life, 5 died (3 peri-treatment, 1 due to disease progression, 1 unrelated), 17 required special education services, 2 required an augmentative assistive communication device, all had some degree of spasticity, and 7 required some type of assistive device for ambulation/mobility (Wright et al. 2017 Neurology 89(13):1365-1372). The New York State newborn screening identified five infants at high risk for infantile KD; one died without HSCT, two died of complications from the procedure, and the two alive have significant GVHD (Wenger et al. 2016 J. Neurosci. Res. 94(11): 982-989).

There remains a need in the art for an effective treatment that targets the cause of the disease, i.e., GALC gene mutations. The present invention overcomes shortcomings in the art by providing codon-optimized GALC genes, expression cassettes, and vectors capable of providing therapeutic levels of GALC expression for treating disorders associated with GALC expression such as KD.

SUMMARY OF THE INVENTION

The present invention is based, in part, on the development of optimized GALC genes, expression cassettes, and vectors capable of providing therapeutic levels of GALC expression for treating disorders associated with GALC expression such as Krabbe disease.

Thus, one aspect of the invention relates to a polynucleotide comprising a canine or human GALC open reading frame, wherein the canine or human GALC open reading frame has been codon-optimized for expression in canine or human cells.

A further aspect of the invention relates to an expression cassette comprising a polynucleotide comprising a canine or human GALC open reading frame and vectors, transformed cells, and transgenic animals comprising the polynucleotide of the invention.

Another aspect of the invention relates to a pharmaceutical formulation comprising the polynucleotide, expression cassette, vector, and/or transformed cell of the invention in a pharmaceutically acceptable carrier.

An additional aspect of the invention relates to a method of expressing a GALC open reading frame in a cell, comprising contacting the cell with the polynucleotide, expression cassette, and/or vector of the invention, thereby expressing the GALC open reading frame in the cell.

A further aspect of the invention relates to a method of expressing a GALC open reading frame in a subject, comprising delivering to the subject the polynucleotide, expression cassette, vector, and/or transformed cell of the invention, thereby expressing the GALC open reading frame in the subject.

An additional aspect of the invention relates to a method of treating a disorder associated with aberrant expression of an GALC gene or aberrant activity of an GALC gene product in a subject in need thereof, comprising administering to the subject a therapeutically effective amount of the polynucleotide, expression cassette, vector, and/or transformed cell of the invention, such that the GALC open reading frame is expressed in the subject.

A further aspect of the invention relates to a method of treating Krabbe disease in a subject in need thereof, comprising administering to the subject a therapeutically effective amount of the polynucleotide, expression cassette, vector, and/or transformed cell of the invention, such that the GALC open reading frame is expressed in the subject.

Another aspect of the invention relates to a polynucleotide, expression cassette, vector, and/or transformed cell of the invention for use in a method of treating a disorder associated with aberrant expression of a GALC gene or aberrant activity of a GALC gene product in a subject in need thereof.

These and other aspects of the invention are set forth in more detail in the description of the invention below.

BRIEF DESCRIPTION OF THE DRAWINGS

FIG. 1 shows similarities in GALC protein sequence between different species. Human (homo; optimized; SEQ ID NO:15) GALC protein mature sequence (no signal peptide) compared to the mouse (mus; SEQ ID NO:13; 83.49%), rat (rattus; SEQ ID NO:12; 82.55%), dog (canis; SEQ ID NO:14; 89.42%) and monkey (macaca; SEQ ID NO:16; 97.20%) retain high level of amino acid identity. The asterisk (*) annotates a fully conserved amino acid residue, colon (:) annotates strongly similar residues and period (.) annotates weakly similar residues. Amino acids that are not conserved are not annotated.

DETAILED DESCRIPTION OF THE INVENTION

Figure 2:
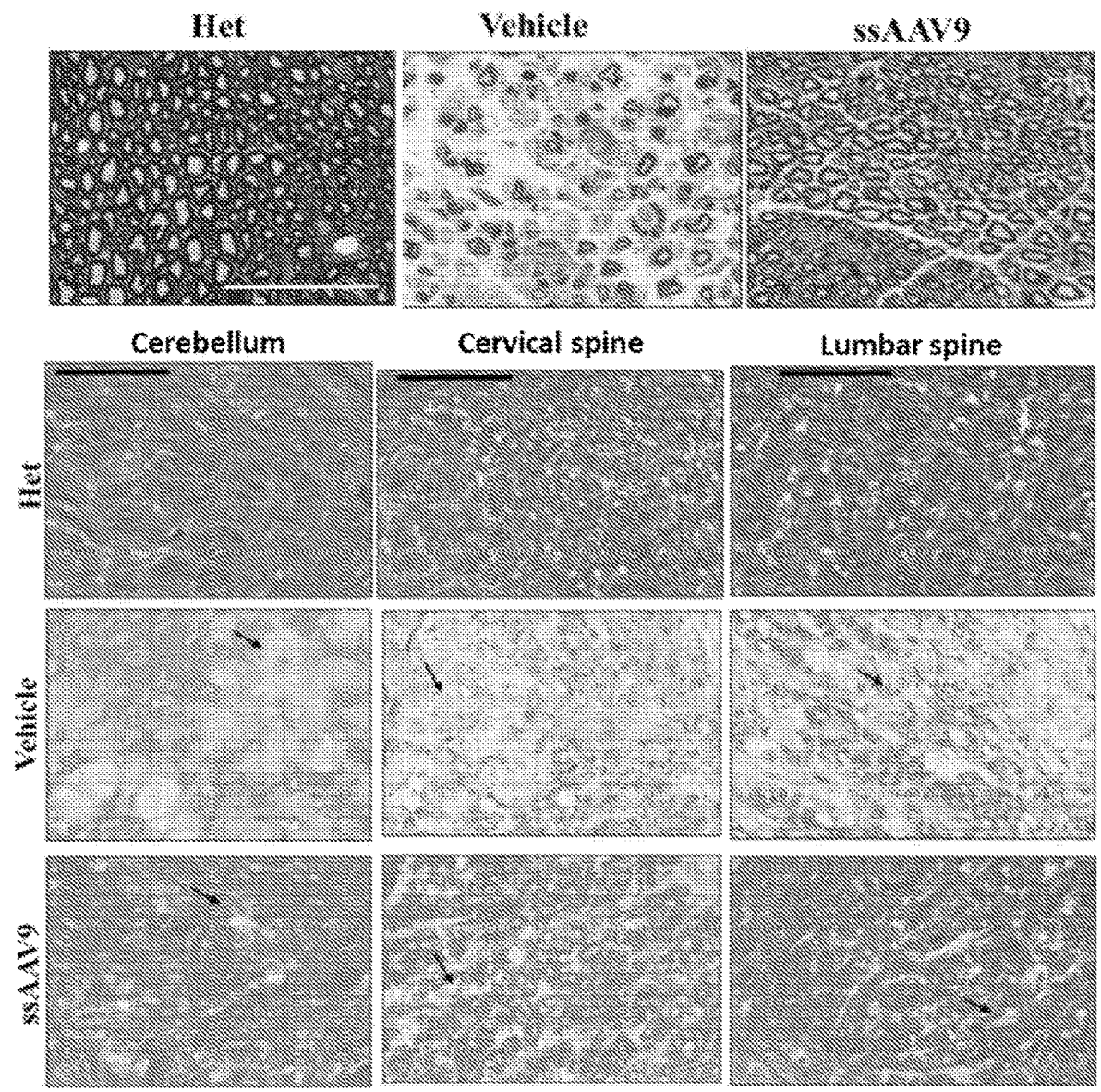
FIG. 2 shows that AAV9/mGALC prevents demyelination. Top panel: Sciatic nerves from PND35 age-matched mice treated at PND11 with vehicle or AAV9/mGALC. Sections stained with toluidine blue detects the preserved myelin around the axons in treated mice (ssAAV9) compared to loss in myelin around degenerating axons in untreated (vehicle). Bottom panel: Luxol fast blue staining of myelin in Cerebellum, cervical and lumbar regions of the CNS in untreated (vehicle) compared to treated mice (ssAAV9) demonstrates well-preserved myelin in mice that received the gene theraPy.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.
Definitions As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or less additional nucleotides or amino acids includes the total number of additional nucleotides or amino acids added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in biological activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera *Parvovirus, Erythrovirus, Densovirus, Iteravirus*, and *Contravirus*. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) *J. Virol.* 78:6381-6388 and Table 1), which are also encompassed by the term "AAV."

The parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73: 939; Chiorini et al., (1997) *J. Virol.* 71:6823; Chiorini et al., (1999) *J. Virol.* 73:1309; Gao et al., (2002) *Proc. Nat. Acad. Sci. USA* 99:11854; Moris et al., (2004) *Virol.* 33-:375-383; Mori et al., (2004) *Virol.* 330: 375; Muramatsu et al., (1996) *Virol.* 221:208; Ruffing et al., (1994) *J. Gen. Virol.* 75:3385; Rutledge et al., (1998) *J. Virol.* 72:309; Schmidt et al., (2008) *J. Virol.* 82:8911; Shade et al., (1986) *J. Virol.* 58:921; Srivastava et al., (1983) *J. Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

A "chimeric" AAV nucleic acid capsid coding sequence or AAV capsid protein is one that combines portions of two or more capsid sequences. A "chimeric" AAV virion or particle comprises a chimeric AAV capsid protein.

The term "tropism" as used herein refers to preferential entry of the virus into certain cell or tissue type(s) and/or preferential interaction with the cell surface that facilitates entry into certain cell or tissue types, optionally and preferably followed by expression (e.g., transcription and, optionally, translation) of sequences carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus and/or from a non-integrated episome, as well as any other form which the virus nucleic acid may take within the cell.

The term "tropism profile" refers to the pattern of transduction of one or more target cells, tissues and/or organs. Representative examples of chimeric AAV capsids have a tropism profile characterized by efficient transduction of cells of the central nervous system (CNS) with only low transduction of peripheral organs (see e.g., U.S. Pat. No. 9,636,370 McCown et al., and US patent publication 2017/0360960 Gray et al.).

The term "disorder associated with aberrant expression of a GALC gene" as used herein refers to a disease, disorder, syndrome, or condition that is caused by or a symptom of decreased or altered expression of the GALC gene in a subject relative to the expression level in a normal subject or in a population.

The term "disorder associated with aberrant activity of a GALC gene product" as used herein refers to a disease, disorder, syndrome, or condition that is caused by or a symptom of decreased or altered activity of the GALC gene product in a subject relative to the activity in a normal subject or in a population.

As used herein, "transduction" of a cell by a virus vector (e.g., an AAV vector) means entry of the vector into the cell and transfer of genetic material into the cell by the incorporation of nucleic acid into the virus vector and subsequent transfer into the cell via the virus vector.

Unless indicated otherwise, "efficient transduction" or "efficient tropism," or similar terms, can be determined by reference to a suitable positive or negative control (e.g., at least about 50%, 60%, 70%, 80%, 85%, 90%, 95% or more of the transduction or tropism, respectively, of a positive control or at least about 110%, 120%, 150%, 200%, 300%, 500%, 1000% or more of the transduction or tropism, respectively, of a negative control).

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism for) tissues outside the CNS, e.g., liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., CNS cells).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide," "nucleic acid," or "nucleotide sequence" may be of RNA, DNA or DNA-RNA hybrid sequences (including both naturally occurring and non-naturally occurring nucleotides), but is preferably either a single or double stranded DNA sequence.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. The region in a nucleic acid sequence or polynucleotide in which one or more regulatory elements are found may be referred to as a "regulatory region."

As used herein with respect to nucleic acids, the term "operably linked" refers to a functional linkage between two or more nucleic acids. For example, a promoter sequence may be described as being "operably linked" to a heterologous nucleic acid sequence because the promoter sequences initiates and/or mediates transcription of the heterologous nucleic acid sequence. In some embodiments, the operably linked nucleic acid sequences are contiguous and/or are in the same reading frame.

The term "open reading frame (ORF)," as used herein, refers to the portion of a polynucleotide, e.g., a gene, that encodes a polypeptide. The term "coding region" may be used interchangeably with open reading frame.

The term "codon-optimized," as used herein, refers to a gene coding sequence that has been optimized to increase expression by substituting one or more codons normally present in a coding sequence (for example, in a wild-type sequence, including, e.g., a coding sequence for GALC) with a codon for the same (synonymous) amino acid. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites, and/or adding or removing ribosomal entry sites, such as Kozak sequences. Desirably, a codon-optimized gene exhibits improved protein expression, for example, the protein encoded thereby is expressed at a detectably greater level in a cell compared with the level of expression of the protein provided by the wild-type gene in an otherwise similar cell.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

TABLE 1

| AAV Serotypes/Isolates | GenBank Accession Number |
|---|---|
| Clonal Isolates | |
| Avian AAV ATCC VR-865 | AY186198, AY629583, NC_004828 |
| Avian AAV strain DA-1 | NC_006263, AY629583 |
| Bovine AAV | NC_005889, AY388617 |
| AAV4 | NC_001829 |
| AAV5 | AY18065, AF085716 |
| Rh34 | AY243001 |
| Rh33 | AY243002 |
| Rh32 | AY243003 |
| AAV10 | AY631965 |
| AAV11 | AY631966 |
| AAV12 | DQ813647 |
| AAV13 | EU285562 |
| Clade A | |
| AAV1 | NC_002077, AF063497 |
| AAV6 | NC_001862 |
| Hu.48 | AY530611 |
| Hu 43 | AY530606 |

TABLE 1-continued

| AAV Serotypes/Isolates | GenBank Accession Number |
| --- | --- |
| Hu 44 | AY530607 |
| Hu 46 | AY530609 |
| Clade B | |
| Hu19 | AY530584 |
| Hu20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| AAV 3 | NC_001729 |
| AAV 3B | NC_001863 |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| AAV9 (Hu14) | AY530579 |
| Hu31 | AY530596 |
| Hu32 | AY530597 |

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" (or grammatical equivalents) a virus vector, it is meant that the virus vector is at least partially separated from at least some of the other components in the starting material.

By the term "treat," "treating," or "treatment of" (or grammatically equivalent terms) is meant to reduce or to at least partially improve or ameliorate the severity of the subject's condition and/or to alleviate, mitigate or decrease in at least one clinical symptom and/or to delay the progression of the condition.

As used herein, the term "prevent," "prevents," or "prevention" (and grammatical equivalents thereof) means to delay or inhibit the onset of a disease. The terms are not meant to require complete abolition of disease, and encompass any type of prophylactic treatment to reduce the incidence of the condition or delays the onset of the condition.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

A "heterologous nucleotide sequence" or "heterologous nucleic acid," with respect to a virus, is a sequence or nucleic acid, respectively, that is not naturally occurring in the virus. Generally, the heterologous nucleic acid or nucleotide sequence comprises an open reading frame that encodes a polypeptide and/or a nontranslated RNA.

A "vector" refers to a compound used as a vehicle to carry foreign genetic material into another cell, where it can be replicated and/or expressed. A cloning vector containing foreign nucleic acid is termed a recombinant vector. Examples of nucleic acid vectors are plasmids, viral vectors, cosmids, expression cassettes, and artificial chromosomes. Recombinant vectors typically contain an origin of replication, a multicloning site, and a selectable marker. The nucleic acid sequence typically consists of an insert (recombinant nucleic acid or transgene) and a larger sequence that serves as the "backbone" of the vector. The purpose of a vector which transfers genetic information to another cell is typically to isolate, multiply, or express the insert in the target cell. Expression vectors (expression constructs or expression cassettes) are for the expression of the exogenous gene in the target cell, and generally have a promoter sequence that drives expression of the exogenous gene/ORF. Insertion of a vector into the target cell is referred to transformation or transfection for bacterial and eukaryotic cells, although insertion of a viral vector is often called transduction. The term "vector" may also be used in general to describe items to that serve to carry foreign genetic material into another cell, such as, but not limited to, a transformed cell or a nanoparticle.

As used herein, the term "vector," "virus vector," "delivery vector" (and similar terms) in a specific embodiment generally refers to a virus particle that functions as a nucleic acid delivery vehicle, and which comprises the viral nucleic acid (i.e., the vector genome) packaged within the virion. Virus vectors according to the present invention comprise a chimeric AAV capsid according to the invention and can package an AAV or rAAV genome or any other nucleic acid including viral nucleic acids. Alternatively, in some contexts, the term "vector," "virus vector," "delivery vector" (and similar terms) may be used to refer to the vector genome (e.g., vDNA) in the absence of the virion and/or to a viral capsid that acts as a transporter to deliver molecules tethered to the capsid or packaged within the capsid.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged.

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) *Curr. Topics Microbiol. Immunol.* 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (ITR) (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The terms "rAAV particle" and "rAAV virion" are used interchangeably here. A "rAAV particle" or "rAAV virion" comprises a rAAV vector genome packaged within an AAV capsid.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids, including non-naturally occurring amino acids.

Naturally occurring, levorotatory (L-) amino acids are shown in Table 2.

TABLE 2

| | Abbreviation | |
|---|---|---|
| Amino Acid Residue | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

Further, the non-naturally occurring amino acid can be an "unnatural" amino acid as described by Wang et al., (2006) *Annu. Rev. Biophys. Biomol. Struct.* 35:225-49. These unnatural amino acids can advantageously be used to chemically link molecules of interest to the AAV capsid protein.

TABLE 3

Amino Acid Residue Derivatives

| Modified Amino Acid Residue | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

By "substantially retain" a property, it is meant that at least about 75%, 85%, 90%, 95%, 97%, 98%, 99% or 100% of the property (e.g., activity or other measurable characteristic) is retained.

GALC Expression Cassettes and Vectors

The present invention relates to the design of a GALC expression cassette to provide therapeutic levels of expression of galactocerebrosidase, the lysosomal enzyme encoded by the GALC gene, and the use of the expression cassette to achieve therapeutic levels of GALC in a subject.

Thus, one aspect of the invention relates to a polynucleotide comprising a mammalian GALC open reading frame (ORF), wherein the GALC open reading frame has been codon-optimized for expression in mammalian cells. The term "mammal" as used herein includes, but is not limited to, humans, primates, non-human primates (e.g., monkeys and baboons), cattle, sheep, goats, pigs, horses, cats, dogs, rabbits, rodents (e.g., rats, mice, hamsters, and the like), etc. The open reading frame is the portion of the GALC gene that encodes GALC. In some embodiments, the mammalian GALC open reading frame may be a human or a canine CALC open reading frame. As used herein, a mammalian GALC ORF refers to a nucleotide sequence that encodes mammalian GALC, e.g., a human or a canine CALC ORF refers to a nucleotide sequence that encodes a human or a canine GALC. Codon optimization is a technique well known in the art and optimal codons for expression in different species are known. The use of a codon-optimized GALC sequence allows one to distinguish expression of the transduced sequence from expression of the endogenous GALC sequence in a subject.

In some embodiments, the codon-optimized GALC open reading frame encodes a GALC enzyme that is modified from the wild-type sequence, e.g., comprises, consists essentially of, or consists of an amino acid sequence in which 1, 2, 3, 4, or 5 residues have been substituted, added, and/or deleted compared to the wild-type amino acid sequence.

In some embodiments, the codon-optimized GALC open reading frame comprises, consists essentially of, or consists of the nucleotide sequence of SEQ ID NO:1 or a sequence at least about 70% identical thereto, e.g., at least about 70, 75, 80, 85, 90, 91, 92, 93, 94, 95, 96, 97, 98, or 99% identical thereto.

```
Human codon-optimized GALC open reading frame
                                         SEQ ID NO: 1
ATGGCTGAGTGGCTCCTTAGCGCGAGCTGGCAGCGGAGAGCCAAGGCAATG

ACAGCGGCGGCGGGCTCCGCCGGACGCGCTGCCGTCCCTCTGTTGCTCTGT

GCGTTGCTGGCACCGGGTGGAGCGTATGTGCTTGATGATTCGGACGGACTC

GGTAGAGAATTTGACGGAATCGGAGCGGTCAGCGGTGGAGGAGCGACGAGC

CGCCTGCTCGTGAACTATCCCGAACCCTACCGATCCCAGATTCTGGACTAC

CTTTTCAAACCTAACTTCGGCGCAAGCCTTCACATCCTCAAGGTGGAGATC

GGTGGGGACGGTCAGACCACAGACGGTACGGAACCATCGCACATGCACTAT

GCGCTCGACGAAAACTACTTTAGAGGGTATGAGTGGTGGCTGATGAAAGAG

GCCAAAAAGCGGAATCCGAATATCACTCTCATTGGTTTGCCGTGGAGCTTC

CCCGGCTGGCTGGGGAAGGGGTTCGACTGGCCCTATGTGAACCTTCAACTG

ACAGCGTATTACGTGGTCACATGGATTGTCGGGGCGAAGAGGTATCATGAC

TTGGATATCGACTATATTGGTATCTGGAACGAGAGATCCTACAACGCAAAC

TACATCAAAATCCTTAGAAAGATGTTGAATTATCAGGGGCTGCAGAGAGTC

AAAATCATCGCATCCGACAATCTTTGGGAATCGATCTCAGCGTCAATGCTC

CTCGACGCGGAACTGTTTAAAGTGGTGGATGTCATTGGGCGCATTACCCG
```

-continued
```
GGAACACACTCGGCGAAAGACGCAAAGTTGACGGGGAAGAAATTGTGGTCG
AGCGAGGATTTTTCCACTCTTAATTCGGATATGGGGGCAGGGTGTTGGGGA
AGAATTCTGAACCAGAACTATATCAACGGGTATATGACCTCGACGATCGCC
TGGAATCTTGTGGCATCCTACTACGAGCAGCTGCCTTACGGGAGGTGCGGT
CTTATGACAGCGCAGGAGCCCTGGTCGGGACATTACGTCGTCGAGAGCCCC
GTATGGGTATCAGCCCACACGACCCAGTTTACACAGCCGGGCTGGTATTAC
CTTAAGACGGTGGGCCATCTTGAGAAGGGAGGTAGCTATGTCGCGCTGACG
GATGGCTTGGGTAATTTGACAATCATCATTGAAACTATGTCGCATAAACAC
TCAAAGTGCATTCGCCCTTTTCTGCCCTATTTCAACGTCAGCCAGCAATTT
GCGACGTTTGTGCTTAAGGGATCGTTTTCGGAGATTCCCGAACTTCAGGTC
TGGTACACGAAACTTGGAAAGACGTCAGAAAGGTTCCTTTTCAAGCAGTTG
GACTCGCTCTGGCTTTTGGATAGCGACGGATCGTTCACTCTGTCCTTGCAC
GAGGATGAGTTGTTCACGCTCACTACCCTCACCACTGGCAGAAAGGGCTCC
TACCCGTTGCCCCCGAAAAGCCAGCCGTTTCCTTCAACTTATAAGGATGAC
TTTAATGTCGATTACCCATTCTTCTCGGAGGCCCCGAATTTTGCCGACCAA
ACAGGAGTATTTGAATACTTCACGAACATCGAGGACCCGGGGGAGCACCAT
TTCACTCTGAGACAAGTGTTGAACCAAAGGCCGATTACTTGGGCAGCCGAT
GCCAGCAATACCATTTCGATTATCGGAGACTATAACTGGACAAACTTGACC
ATCAAATGCGATGTCTATATCGAAACGCCTGATACAGGGGGTGTGTTCATC
GCTGGTCGCGTAAACAAAGGGGGAATTTTGATCCGCTCAGCTAGAGGGATC
TTCTTTTGGATTTTCGCGAACGGAAGCTACCGCGTGACGGGAGACTTGGCG
GGATGGATCATCTACGCCCTGGGTCGCGTGGAGGTAACAGCGAAAAAGTGG
TACACGTTGACCTTGACAATTAAGGGGCACTTCACGTCCGGGATGCTGAAC
GACAAGAGCCTCTGGACGGACATCCCCGTGAATTTCCCCAAAAACGGGTGG
GCAGCAATTGGGACGCACTCCTTTGAATTTGCGCAATTCGACAACTTTTTG
GTAGAGGCTACGCGG.
```

In some embodiments, the codon-optimized GALC open reading frame comprises, consists essentially of, or consists of the nucleotide sequence of SEQ ID NO:2 or a sequence at least about 70% identical thereto, e.g., at least about 70, 75, 80, 85, 90, 91, 92, 93, 94, 95, 96, 97, 98, or 99% identical thereto.

```
Canine codon-optimized GALC open reading frame
                                        SEQ ID NO: 2
ATGACCGCAGCCGCAGGATCTGCAGGCCATGCTGCGGTGCCCCTGTTGTTG
TGTGCCCTTCTGGTCCCTGGCGGAGCTTACGTGCTGGACGACTCCGACGGT
TTGGGCCGGGAGTTCGACGGAGTGGGAGCTGTCTCCGGTGGTGGAGCGACC
AGCAGACTCCTCGTGAACTACCCGGAGCCGTACAGGTCACAGATCCTCGAC
TACCTGTTCAAGCCAAATTTCGGTGCCTCCCTTCATATCCTGAAAGTGGAA
ATCGGTGGAGATGGACAGACTACCGACGGAACGGAGCCCTCCCACATGCAT
TACGCCCTGGACGAAAATTTCTTCCGGGGCTACGAGTGGTGGCTGATGAAG
GAGGCCAAGAAGCGGAACCCGAACATCATCCTGATGGGACTCCCTTGGTCC
TTCCCCGGCTGGATCGGAAAGGGATTCAACTGGCCCTACGTGAACCTCCAG
CTTACCGCCTACTACATCATGACTTGGATTGTGGGCGCCAAGCATTACCAC
GACCTGGACATCGACTACATCGGCATTTGGAACGAGCGGTCCTTTGACATC
AACTACATTAAGGTGCTGAGGAGGATGCTGAATTATCAGGGACTCGACAGA
GTGAAGATTATTGCCTCGGACAACCTGTGGGAGCCGATCTCGGCGTCCATG
CTGCTTGATAGCGAGCTCCTCAAGGTCATCGACGTGATCGGAGCCCACTAC
CCTGGTACACACACCGTGAAGGACGCGAAGCTGACCAAGAAGAAGCTGTGG
TCCTCCGAGGACTTCTCCACCCTGAACAGCGATGTCGGAGCCGGATGCTTG
GGACGGATCCTGAACCAGAACTACGTGAACGGCTACATGACCGCCACCATT
GCCTGGAACCTGGTGGCGTCTTACTATGAGCAACTCCCTTACGGACGCTGT
GGGCTGATGACTGCCCAGGAACCATGGAGCGGCCACTACGTGGTGGAGTCC
CCTATCTGGGTCAGCGCCCACACCACCCAGTTTACCCAGCCGGGATGGTAC
TACCTCAAGACCGTGGGGCACCTTGAGAAGGGAGGATCCTACGTCGCTCTC
ACTGACGGGCTCGGCAACTTGACTATCATAGTGGAAACTATGTCCCACAAG
CAGTCCGCATGCATTCGGCCCTTCTTGCCGTACTTCAACGTGTCACCAGTT
CGCCACTTTCGTGCTGAAGGGTTCGTTCAGCGAGATCCCGGAGCTCCAAGT
CTGGTACACTAAGCTGGGAAAGCCTTCAGAACGCTACCTCTTCAAGCAGCT
GGACTCCCTGTGGCTGCTGGATTCATCATCGACCTTCACCCTGGAACTGCA
GGAAGATGAAATCTTCACCCTGACCACTCTGACTGTGGGCAGCAAGGGCTC
GTATCCGCTCCCGCCGAAGTCGGAGCCCTTTCCCCAAATCTACGAAGATGA
CTTCGACGTGGACTATCCCTTCTTCTCGGAAGCCCCAAACTTCGCTGATCA
AACCGGAGTGTTTGAGTATTTCACCAACATTGAGGACCCCGGAGAACACAG
ATTCACGCTGCGCCAAGTGCTCAACCAGCGCCCCATCACCTGGGCCGCTGA
TGCCTACAACACCATTTCCATCATTGGGGACTACAAATGGTCGAACCTGAC
CGTGCGCTGCGACGTGTACATCGAAACCCCCGAAAAGGGCGGCGTGTTCAT
CGCTGGCCGGGTCAACAAGGGGGGGATTCTTATTAGATCCGCGAGGGGGAT
CTTTTTCTGGATCTTCGCCAACGGGACTTACCGCGTGACCGGAGATCTGGC
CGGCTGGGTGATCTACGCCCTGGGTAGAGTGGACGTGACCGCGAAGAAATG
GTACACTCTGACCCTGATTATCAAAGGGCGGTTGAGCTCCGGCATGCTGAA
CGGGAAAACTGTCTGGAAAAACATCCCAGTGTCATTCCCTAAGAACGGATG
GGCCGCCATCGGAACTCACAGCTTTGAGTTCGCCCAGTTTGATAACTTTCA
TGTCGAAGCGACCCGC.
```

Another aspect of the invention relates to an expression cassette comprising a polynucleotide comprising a canine or human GALC open reading frame. In certain embodiments, the polynucleotide is a canine or human codon-optimized sequence, e.g., a polynucleotide comprising the nucleotide sequence of SEQ ID NO:1 or SEQ ID NO:2, or a sequence at least about 70% identical thereto, e.g., at least about 70, 75, 80, 85, 90, 91, 92, 93, 94, 95, 96, 97, 98, or 99% identical thereto.

The GALC open reading frame in the expression cassette may be operably linked to one or more expression elements that may enhance expression of GALC. In some embodiments, the polynucleotide is operably linked to a promoter, e.g., a chicken beta-actin promoter, e.g., a promoter comprising, consisting essentially of, or consisting of the nucleotide sequence of SEQ ID NO:3 or a sequence at least about 70% identical thereto, e.g., at least about 70, 75, 80, 85, 90, 91, 92, 93, 94, 95, 96, 97, 98, or 99% identical thereto.

Chicken beta-actin promoter
SEQ ID NO: 3
TACGTATTAGTCATCGCTATTACCATGGTCGAGGTGAGCCCCACGTTCTGC

TTCACTCTCCCCATCTCCCCCCCCTCCCCACCCCCAATTTTGTATTTATTT

ATTTTTTAATTATTTTGTGCAGCGATGGGGGCGGGGGGGGGGGGGGGCGC

GCGCCAGGCGGGGCGGGGCGGGGCGAGGGGCGGGGCGGGGCGAGGCGGAGA

GGTGCGGCGGCAGCCAATCAGAGCGGCGCGCTCCGAAAGTTTCCTTTTATG

GCGAGGCGGCGGCGGCGGCGGCCCTATAAAAAGCGAAGCGCGCGGCGGGC

G.

In some embodiments, the polynucleotide is operably linked to a promoter, e.g., a CAGGS promoter, e.g., a promoter comprising, consisting essentially of, or consisting of the nucleotide sequence of SEQ ID NO:4 or a sequence at least about 70% identical thereto, e.g., at least about 70, 75, 80, 85, 90, 91, 92, 93, 94, 95, 96, 97, 98, or 99% identical thereto.

CAGGS promoter 1.6 kb CMV enhancer, CBA promoter and partial 5' UTR
SEQ ID NO: 4
GATCTGAATTCGGATCTTCAATATTGGCCATTAGCCATATTATTCATTGGT

TATATAGCATAAATCAATATTGGATATTGGCCATTGCATACGTTGTATCTA

TATCATAATATGTACATTTATATTGGCTCATGTCCAATATGACCGCCATGT

TGGCATTGATTATTGACTAGTTATTAATAGTAATCAATTACGGGGTCATTA

GTTCATAGCCCATATATGGAGTTCCGCGTTACATAACTTACGGTAAATGGC

CCGCCTGGCTGACCGCCCAACGACCCCCGCCCATTGACGTCAATAATGACG

TATGTTCCCATAGTAACGCCAATAGGGACTTTCCATTGACGTCAATGGGTG

GAGTATTTACGGTAAACTGCCCACTTGGCAGTACATCAAGTGTATCATATG

CCAAGTCCGCCCCCTATTGACGTCAATGACGGTAAATGGCCCGCCTGGCAT

TATGCCCAGTACATGACCTTACGGGACTTTCCTACTTGGCAGTACATCTAC

GTATTAGTCATCGCTATTACCATGGTCGAGGTGAGCCCCACGTTCTGCTTC

ACTCTCCCCATCTCCCCCCCCTCCCCACCCCCAATTTTGTATTTATTTATT

TTTTAATTATTTTGTGCAGCGATGGGGCGGGGGGGGGGGGGGGCGCGCG

CCAGGCGGGCGGGGCGGGCGAGGGGCGGGCGGGGCGAGGCGGAGAGGT

GCGGCGGCAGCCAATCAGAGCGGCGCGCTCCGAAAGTTTCCTTTTATGGCG

AGGCGGCGGCGGCGGCGGCCCTATAAAAAGCGAAGCGCGCGGCGGGCGGGA

GTCGCTGCGACGCTGCCTTCGCCCCGTGCCCCGCTCCGCCGCCGCCTCGCG

CCGCCCGCCCCGGCTCTGACTGACCGCGTTACTCCCACAGGTGAGCGGGCG

GGACGGCCCTTCTCCTCCGGGCTGTAATTAGCGCTTGGTTTAATGACGGCT

TGTTTCTTTTCTGTGGCTGCGTGAAAGCCTTGAGGGGCTCCGGGAGGGCCC

TTTGTGCGGGGGGAGCGGCTCGGGGGTGCGTGCGTGTGTGTGCGTGG

GGAGCGCCGCGTGCGGCCCGCGCTGCCCGGCGGCTGTGAGCGCTGCGGGCG

CGGCGCGGGGCTTTGTGCGCTCCGCAGTGTGCGCGAGGGGAGCGCGGCCGG

GGGCGGTGCCCCGCGGTGCGGGGGGGGCTGCGAGGGGAACAAAGGCTGCGT

GCGGGGTGTGTGCGTGGGGGGGTGAGCAGGGGGTATGGGCGCGGCGGTCGG

GCTGTAACCCCCCCCTGCACCCCCCTCCCCGAGTTGCTGAGCACGGCCCGG

CTTCGGGTGCGGGGCTCCGTACGGGGCGTGGCGCGGGGCTCGCCGTGCCGG

GCGGGGGGTGGCGGCAGGTGGGGGTGCCGGGCGGGGCGGGGCCGCCTCGGG

CCGGGGAGGGCTCGGGGGAGGGGCGCGGCGGCCCCCGGAGCGCCGGCGGCT

GTCGAGGCGCGGCGAGCCGCAGCCATTGCCTTTTATGGTAATCGTGCGAGA

GGGCGCAGGGACTTACTTTGTCCCAAATCTGTGCGGAGCCGAAATCTGGGA

GGCGCCGCCGCACCCCCTCTAGCGGGCGCGGGGCGAAGCGGTGCGGCGCCG

GCAGGAAGGAAATGGGCGGGGAGGGCCTTCGTGCGTCGCCGCGCCGCCGTC

CCCTTCTCCCTCTCCAGCCTCGGGGCTGTCCGCGGGGGGACGGCTGCCTTC

GGGGGGGACGGGGCAGGGCGGGGTTCGGCTTCTGGCGTGTGACCGGCGGCT

CTAGAGCCTCTGCTAACCATGTTCATGCCTTCTTCTTTTTCCTACAGCTCC

TGGGCAACGTGCTGGTTATTGTGCTGTCTCATCATTTTGGCAAAG.

In some embodiments, the polynucleotide is operably linked to a promoter, e.g., a JeT promoter, e.g., a promoter comprising, consisting essentially of, or consisting of the nucleotide sequence of SEQ ID NO:5 or a sequence at least about 70% identical thereto, e.g., at least about 70, 75, 80, 85, 90, 91, 92, 93, 94, 95, 96, 97, 98, or 99% identical thereto.

JeT promoter
SEQ ID NO: 5
gggcggagttagggcggagccaatcagcgtgcgccgttccgaaagttgcct ttatggctgggcggagaatgggcggtgaacgccgatgattatataaggacg cgccgggtgtggcacagctagttccgtcgcagccgggatttgggtcgcggt tcttgtttgt.

In some embodiments, the GALC open reading frame is operably linked to a polyadenylation signal, e.g., a synthetic polyadenylation signal, e.g., a polyadenylation signal comprising, consisting essentially of, or consisting of the nucleotide sequence of SEQ ID NO:6 or a sequence at least about 70% identical thereto, e.g., at least about 70, 75, 80, 85, 90, 91, 92, 93, 94, 95, 96, 97, 98, or 99% identical thereto.

SEQ ID NO: 6:
Synthetic polyadenylation signal (SpA)
AATAAAGAGCTCAGATGCATCGATCAGAGTGTGTTGGTTTTTTGTGTG In some embodiments, the polynucleotide is operably linked to a polyadenylation signal, e.g., a simian virus 40 (SV40) polyadenylation signal, e.g., a polyadenylation signal comprising, consisting essentially of, or consisting of the nucleotide sequence of SEQ ID NO:7 or a sequence at least about 70% identical thereto, e.g., at least about 70, 75, 80, 85, 90, 91, 92, 93, 94, 95, 96, 97, 98, or 99% identical thereto.

SV40 polyadenylation signal (SV40pA)
SEQ ID NO: 7
AGACATGATAAGATACATTGATGAGTTTGGACAAACCACAACTAGAATGCA

```
-continued
GTGAAAAAAATGCTTTATTTGTGAAATTTGTGATGCTATTGCTTTATTTGT

AACCATTATAAGCTGCAATAAACAAGTTAACAACAACAATT.
```

Those skilled in the art will further appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements can be native to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be constitutive or inducible.

Inducible expression control elements are generally used in those applications in which it is desirable to provide regulation over expression of the heterologous nucleic acid sequence(s). Inducible promoters/enhancer elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the GALC open reading frame is transcribed and then translated in the target cells, specific initiation signals are generally employed for efficient translation of inserted protein coding sequences. These exogenous translational control sequences, which may include the ATG initiation codon and adjacent sequences, can be of a variety of origins, both natural and synthetic.

In certain embodiments, the expression cassette further comprises at least one adeno-associated virus (AAV) inverted terminal repeat (ITR), e.g., two AAV ITRs. The two ITRs may have the same nucleotide sequence or different nucleotide sequences. The AAV ITRs may be from any AAV serotype, e.g., AAV2, AAV9, AAVrh10, or any AAV serotype as listed in Table 1. In some embodiments, the AAV ITRs may be AAV2 ITRs. Each ITR independently may be the wild-type sequence or a modified sequence. In some embodiments, a modified ITR may have a D-element deletion (WO 01/92551). A D-element deletion is defined as the removal of that portion of the ITR known as the D-element. The D-element can be alternatively referred to or known as a D region, or D sequence, and/or the nucleotides of the ITR that do not form palindromic hairpin structures. In some embodiments, the expression cassette is an AAV genome, e.g., a self-complementary AAV genome.

In certain embodiments, the expression cassette comprises a promoter, a human or canine GALC open reading frame, and a polyadenylation site, optionally in the recited order. In certain embodiments, the expression cassette comprises an AAV ITR, a promoter, a human or canine GALC open reading frame, a polyadenylation site, and an AAV ITR, optionally in the recited order. In certain embodiments, the expression cassette comprises a chicken beta actin promoter, a human or canine GALC open reading frame, and an SV40 polyadenylation site, optionally in the recited order. In certain embodiments, the expression cassette comprises an AAV ITR, a chicken beta actin promoter, a human or canine GALC open reading frame, an SV40 polyadenylation site, and an AAV ITR, optionally in the recited order. In certain embodiments, the expression cassette comprises an AAV2 ITR, a chicken beta actin promoter, a human GALC open reading frame, an SV40 polyadenylation site, and an AAV2 ITR, optionally in the recited order. In certain embodiments, the expression cassette comprises an AAV2 ITR, a chicken beta actin promoter, a canine GALC open reading frame, an SV40 polyadenylation site, and an AAV2 ITR, optionally in the recited order. In certain embodiments, the expression cassette comprises an AAV9 ITR, a CAGGS promoter, a human GALC open reading frame, an SV40 polyadenylation site, and an AAV2 ITR, optionally in the recited order. In certain embodiments, the expression cassette comprises an AAV2 ITR, a CAGGS promoter, a canine GALC open reading frame, an SV40 polyadenylation site, and an AAV2 ITR, optionally in the recited order. In certain embodiments, the expression cassette comprises an AAV ITR, a JeT promoter, a human or canine GALC open reading frame, a synthetic polyadenylation site, and an AAV ITR, optionally in the recited order. In certain embodiments, the expression cassette comprises an AAV2 ITR, a JeT promoter, a human GALC open reading frame, a synthetic polyadenylation site, and an AAV2 ITR, optionally in the recited order. In certain embodiments, the expression cassette comprises an AAV2 ITR, a JeT promoter, a canine GALC open reading frame, a synthetic polyadenylation site, and an AAV2 ITR, optionally in the recited order. The aforementioned components are in operable linkage.

In some embodiments, the expression cassette comprise, consists essentially of, or consists of the nucleotide sequence of SEQ ID NO:8 or a sequence at least about 70% identical thereto, e.g., at least about 70, 75, 80, 85, 90, 91, 92, 93, 94, 95, 96, 97, 98, or 99% identical thereto.

```
Human GALC expression cassette with CAGGS/SV40polyA
                                          SEQ ID NO: 8
GGGGGGGGGGGGGGGGGTTGGCCACTCCCTCTCTGCGCGCTCGCTCGCTCA

CTGAGGCCGGGCGACCAAAGGTCGCCCGACGCCCGGGCTTTGCCCGGGCGG

CCTCAGTGAGCGAGCGAGCGCGCAGAGAGGGAGTGGCCAACTCCATCACTA

GGGGTTCCTAGATCTGAATTCGGATCTTCAATATTGGCCATTAGCCATATT

ATTCATTGGTTATATAGCATAAATCAATATTGGCTATTGGCCATTGCATAC

GTTGTATCTATATCATAATATGTACATTTATATTGGCTCATGTCCAATATG

ACCGCCATGTTGGCATTGATTATTGACTAGTTATTAATAGTAATCAATTAC

GGGGTCATTAGTTCATAGCCCATATATGGAGTTCCGCGTTACATAACTTAC

GGTAAATGGCCCGCCTGGCTGACCGCCCAACGACCCCCGCCCATTGACGTC

AATAATGACGTATGTTCCCATAGTAACGCCAATAGGGACTTTCCATTGACG
```

```
TCAATGGGTGGAGTATTTACGGTAAACTGCCCACTTGGCAGTACATCAAGT
GTATCATATGCCAAGTCCGCCCCCTATTGACGTCAATGACGGTAAATGGCC
CGCCTGGCATTATGCCCAGTACATGACCTTACGGGACTTTCCTACTTGGCA
GTACATCTACGTATTAGTCATCGCTATTACCATGGTCGAGGTGAGCCCCAC
GTTCTGCTTCACTCTCCCCATCTCCCCCCCCTCCCCACCCCCAATTTTGTA
TTTATTTATTTTTTAATTATTTTGTGCAGCGATGGGGGCGGGGGGGGGGGG
GGGGCGCGCGCCAGGCGGGGCGGGGCGGGGCGAGGGGCGGGGCGGGGCGAG
GCGGAGAGGTGCGGCGGCAGCCAATCAGAGCGGCGCGCTCCGAAAGTTTCC
TTTTATGGCGAGGCGGCGGCGGCGGCGCCCTATAAAAAGCGAAGCGCGCG
GCGGGCGGGAGTCGCTGCGACGCTGCCTTCGCCCCGTGCCCCGCTCCGCCG
CCGCCTCGCGCCGCCCGCCCCGGCTCTGACTGACCGCGTTACTCCCACAGG
TGAGCGGGCGGGACGGCCCTTCTCCTCCGGGCTGTAATTAGCGCTTGGTTT
AATGACGGCTTGTTTCTTTTCTGTGGCTGCGTGAAAGCCTTGAGGGGCTCC
GGGAGGGCCCTTTGTGCGGGGGGGAGCGGCTCGGGGGGTGCGTGCGTGTGT
GTGTGCGTGGGGAGCGCCGCGTGCGGCCCGCGCTGCCCGGCGGCTGTGAGC
GCTGCGGGCGCGGCGCGGGCTTTGTGCGCTCCGCAGTGTGCGCGAGGGGA
GCGCGGCCGGGGCGGTGCCCCGCGGTGCGGGGGGGCTGCGAGGGGAACA
AAGGCTGCGTGCGGGGTGTGTGCGTGGGGGGTGAGCAGGGGGTATGGGCG
CGGCGGTCGGGCTGTAACCCCCCCTGCACCCCCCTCCCCGAGTTGCTGAG
CACGGCCCGGCTTCGGGTGCGGGGCTCCGTACGGGGCGTGGCGCGGGGCTC
GCCGTGCCGGGCGGGGGTGGCGGCAGGTGGGGGTGCCGGGCGGGGCGGGG
CCGCCTCGGGCCGGGGAGGGCTCGGGGAGGGGCGCGGCGGCCCCCGGAGC
GCCGGCGGCTGTCGAGGCGCGGCGAGCCGCAGCCATTGCCTTTTATGGTAA
TCGTGCGAGAGGGCGCAGGGACTTCCTTTGTCCCAAATCTGTGCGGAGCCG
AAATCTGGGAGGCGCCGCCGCACCCCCTCTAGCGGGCGCGGGGCGAAGCGG
TGCGGCGCCGGCAGGAAGGAAATGGGCGGGAGGGCCTTCGTGCGTCGCCG
CGCCGCCGTCCCCTTCTCCCTCTCCAGCCTCGGGGCTGTCCGCGGGGGGAC
GGCTGCCTTCGGGGGGACGGGGCAGGGCGGGGTTCGGCTTCTGGCGTGTG
ACCGGCGGCTCTAGAGCCTCTGCTAACCATGTTCATGCCTTCTTCTTTTTC
CTACAGCTCCTGGGCAACGTGCTGGTTATTGTGCTGTCTCATCATTTTGGC
AAAGAATTCTAGAGGATCCGGTACTCGAGGAACTGAAAAACCAGAAAGTTA
ACTGGTAAGTTTAGTCTTTTTGTCTTTTATTTCAGGTCCCGGATCCGGTGG
TGGTGCAAATCAAAGAACTGCTCCTCAGTGGATGTTGCCTTTACTTCTAGG
CCTGTACGGAAGTGTTACTTCTGCTCTAAAAGCTGCGGAATTGTACCCGCG
GCCCGGGATCCACCGGTGCCACCATGGCTGAGTGGCTCCTTAGCGCGAGCT
GGCAGCGGAGAGCCAAGGCAATGACAGCGGCGGCGGGCTCCGCCGGACGCG
CTGCCGTCCCTCTGTTGCTCTGTGCGTTGCTGGCACCGGGTGGAGCGTATG
TGCTTGATGATTCGGACGGACTCGGTAGAGAATTTGACGAATCGGAGCGG
TCAGCGGTGGAGGAGCGACGAGCCGCCTGCTCGTGAACTATCCCGAACCCT
ACCGATCCCAGATTCTGGACTACCTTTTCAAACCTAACTTCGGCGCAAGCC
TTCACATCCTCAAGGTGGAGATCGGTGGGGACGGTCAGACCCACAGACGGTA
```

```
CGGAACCATCGCACATGCACTATGCGCTCGACGAAAACTACTTTAGAGGGT
ATGAGTGGTGGCTGATGAAAGAGGCCAAAAAGCGGAATCCGAATATCACTC
TCATTGGTTTGCCGTGGAGCTTCCCCGGCTGGCTGGGAAGGGGTTCGACT
GGCCCTATGTGAACCTTCAACTGACAGCGTATTACGTGGTCACATGGATTG
TCGGGGCGAAGAGGTATCATGACTTGGATATCGACTATATTGGTATCTGGA
ACGAGAGATCCTACAACGCAAACTACATCAAAATCCTTAGAAAGATGTTGA
ATTATCAGGGGCTGCAGAGAGTCAAAATCATCGCATCCGACAATCTTTGGG
AATCGATCTCAGCGTCAATGCTCCTCGACGCGGAACTGTTTAAAGTGGTGG
ATGTCATTGGGGCGCATTACCCGGGAACACACTCGGCGAAAGACGCAAAGT
TGACGGGAAGAAATTGTGGTCGAGCGAGGATTTTTCCACTCTTAATTCGG
ATATGGGGCAGGGTGTTGGGGAAGAATTCTGAACCAGAACTATATCAACG
GGTATATGACCTCGACGATCGCCTGGAATCTTGTGGCATCCTACTACGAGC
AGCTGCCTTACGGGAGGTGCGGTCTTATGACAGCGCAGGAGCCCTGGTCGG
GACATTACGTCGTCGAGAGCCCCGTATGGGTATCAGCCCACACGACCCAGT
TTACACAGCCGGGCTGGTATTACCTTAAGACGGTGGGCCATCTTGAGAAGG
GAGGTAGCTATGTCGCGCTGACGGATGGCTTGGGTAATTTGACAATCATCA
TTGAAACTATGTCGCATAAACACTCAAAGTGCATTCGCCCTTTTCTGCCCT
ATTTCAACGTCAGCCAGCAATTTGCGACGTTTGTGCTTAAGGGATCGTTTT
CGGAGATTCCCGAACTTCAGGTCTGGTACACGAAACTTGGAAAGACGTCAG
AAAGGTTCCTTTTCAAGCAGTTGGACTCGCTCTGGCTTTTGGATAGCGACG
GATCGTTCACTCTGTCCTTGCACGAGGATGAGTTGTTCACGCTCACTACCC
TCACCACTGGCAGAAAGGGCTCCTACCCGTTGCCCCGAAAAGCCAGCCGT
TTCCTTCAACTTATAAGGATGACTTTAATGTCGATTACCCATTCTTCTCGG
AGGCCCCGAATTTTGCCGACCAAACAGGAGTATTTGAATACTTCACGAACA
TCGAGGACCCGGGGGAGCACCATTTCACTCTGAGACAAGTGTTGAACCAAA
GGCCGATTACTTGGGCAGCCGATGCCAGCAATACCATTTCGATTATCGGAG
ACTATAACTGGACAAACTTGACCATCAAATGCGATGTCTATATCGAAACGC
CTGATACAGGGGGTGTGTTCATCGCTGGTCGCGTAAACAAAGGGGAATTT
TGATCCGCTCAGCTAGAGGGATCTTCTTTTGGATTTTCGCGAACGGAAGCT
ACCGCGTGACGGGAGACTTGGCGGGATGGATCATCTACGCCCTGGGTCGCG
TGGAGGTAACAGCGAAAAAGTGGTACACGTTGACCTTGACAATTAAGGGGC
ACTTCACGTCCGGGATGCTGAACGACAAGAGCCTCTGGACGGACATCCCCG
TGAATTTCCCCAAAAACGGGTGGGCAGCAATTGGGACGCACTCCTTTGAAT
TTGCGCAATTCGACAACTTTTTGGTAGAGGCTACGCGGTGATAGCCTAGGG
ATGGCCGCGCGGATCCAGACATGATAAGATACATTGATGAGTTTGGACAAA
CCACAACTAGAATGCAGTGAAAAAAATGCTTTATTTGTGAAATTTGTGATG
CTATTGCTTTATTTGTAACCATTATAAGCTGCAATAAACAAGTTAACAACA
ACAATTTAGCAGGCATGCTGGGGAGAGATCTAGGAACCCCTAGTGATGGAG
TTGGCCACTCCCTCTCTGCGCGCTCGCTCGCTCACTGAGGCCGCCCGGGCA
```

AAGCCCGGGCGTCGGGCGACCTTTGGTCGCCCGGCCTCAGTGAGCGAGCGA
GCGCGCAGAGAGGGAGTGGCCAACCCCCCCCCCCCCCCC.

In some embodiments, the expression cassette comprise, consists essentially of, or consists of the nucleotide sequence of SEQ ID NO:9 or a sequence at least about 70% identical thereto, e.g., at least about 70, 75, 80, 85, 90, 91, 92, 93, 94, 95, 96, 97, 98, or 99% identical thereto.

```
Canine GALC expression cassette with
CAGGS/SV40polyA
                                            SEQ ID NO: 9
GGGGGGGGGGGGGGGGGTTGGCCACTCCCTCTCTGCGCGCTCGCTCGCTCA
CTGAGGCCGGGCGACCAAAGGTCGCCCGACGCCCGGGCTTTGCCCGGGCGG
CCTCAGTGAGCGAGCGAGCGCGCAGAGAGGGAGTGGCCAACTCCATCACTA
GGGGTTCCTAGATCTGAATTCGGATCTTCAATATTGGCCATTAGCCATATT
ATTCATTGGTTATATAGCATAAATCAATATTGGATATTGGCCATTGCATAC
GTTGTATCTATATCATAATATGTACATTTATATTGGCTCATGTCCAATATG
ACCGCCATGTTGGCATTGATTATTGACTAGTTATTAATAGTAATCAATTAC
GGGGTCATTAGTTCATAGCCCATATATGGAGTTCCGCGTTACATAACTTAC
GGTAAATGGCCCGCCTGGCTGACCGCCCAACGACCCCCGCCCATTGACGTC
AATAATGACGTATGTTCCCATAGTAACGCCAATAGGGACTTTCCATTGACG
TCAATGGGTGGAGTATTTACGGTAAACTGCCCACTTGGCAGTACATCAAGT
GTATCATATGCCAAGTCCGCCCCCTATTGACGTCAATGACGGTAAATGGCC
CGCCTGGCATTATGCCCAGTACATGACCTTACGGGACTTTCCTACTTGGCA
GTACATCTACGTATTAGTCATCGCTATTACCATGGTCGAGGTGAGCCCCAC
GTTCTGCTTCACTCTCCCCATCTCCCCCCCCTCCCCACCCCCAATTTTGTA
TTTATTTATTTTTTAATTATTTTGTGCAGCGATGGGGGCGGGGGGGGGGG
GGGGCGCGCGCCAGGCGGGGCGGGGCGGGGCGAGGGGCGGGGCGGGGCGAG
GCGGAGAGGTGCGGCGGCAGCCAATCAGAGCGGCGCGCTCCGAAAGTTTCC
TTTTATGGCGAGGCGGCGGCGGCGGCGGCCCTATAAAAAGCGAAGCGCGCG
GCGGGCGGGAGTCGCTGCGACGCTGCCTTCGCCCCGTGCCCCGCTCCGCCG
CCGCCTCGCGCCGCCCGCCCCGGCTCTGACTGACCGCGTTACTCCCACAGG
TGAGCGGGCGGGACGGCCCTTCTCCTCCGGGCTGTAATTAGCGCTTGGTTT
AATGACGGCTTGTTTCTTTTCTGTGGCTGCGTGAAAGCCTTGAGGGGCTCC
GGGAGGGCCCTTTGTGCGGGGGGAGCGGCTCGGGGGGTGCGTGCGTGTGT
GTGTGCGTGGGGAGCGCCGCGTGCGGCCCGCGCTGCCCGGCGGCTGTGAGC
GCTGCGGGCGCGGCGCGGGGCTTTGTGCGCTCCGCAGTGTGCGCGAGGGGA
GCGCGGCCGGGGCGGTGCCCCGCGGTGCGGGGGGGCTGCGAGGGGAACA
AAGGCTGCGTGCGGGGTGTGTGCGTGGGGGGGTGAGCAGGGGGTATGGGCG
CGGCGGTCGGGCTGTAACCCCCCCCTGCACCCCCCTCCCCGAGTTGCTGAG
CACGGCCCGGCTTCGGGTGCGGGGCTCCGTACGGGGCGTGGCGCGGGGCTC
GCCGTGCCGGCGGGGGTGGCGGCAGGTGGGGGTGCCGGCGGGGCGGGG
CCGCCTCGGGCCGGGAGGGCTCGGGGGAGGGGCGCGGCGGCCCCGGAGC
GCCGGCGGCTGTCGAGGCGCGGCGAGCCGCAGCCATTGCCTTTTATGGTAA
TCGTGCGAGAGGGCGCAGGGACTTACTTTGTCCCAAATCTGTGCGGAGCCG
AAATCTGGGAGGCGCCGCCGCACCCCCTCTAGCGGGCGCGGGGCGAAGCGG
TGCGGCGCCGGCAGGAAGGAAATGGGCGGGGAGGGCCTTCGTGCGTCGCCG
CGCCGCCGTCCCCTTCTCCCTCTCCAGCCTCGGGGCTGTCCGCGGGGGGAC
GGCTGCCTTCGGGGGGACGGGGCAGGGCGGGGTTCGGCTTCTGGCGTGTG
ACCGGCGGCTCTAGAGCCTCTGCTAACCATGTTCATGCCTTCTTCTTTTTC
CTACAGCTCCTGGGCAACGTGCTGGTTATTGTGCTGTCTCATCATTTTGGC
AAAGAATTCTAGAGGATCCGGTACTCGAGGAACTGAAAAACCAGAAAGTTA
ACTGGTAAGTTTAGTCTTTTTGTCTTTTATTTCAGGTCCCGGATCCGGTGG
TGGTGCAAATCAAAGAACTGCTCCTCAGTGGATGTTGCCTTTACTTCTAGG
CCTGTACGGAAGTGTTACTTCTGCTCTAAAAGCTGCGGAATTGTACCCGCG
GCCCGGGATCCAACCGGTGCCACCATGACCGCAGCCGCAGGATCTGCAGGC
CATGCTGCGGTGCCCCTGTTGTTGTGTGCCCTTCTGGTCCCTGGCGGAGCT
TACGTGCTGGACGACTCCGACGGTTTGGGCCGGGAGTTCGACGGAGTGGGA
GCTGTCTCCGGTGGTGGAGCGACCAGCAGACTCCTCGTGAACTACCCGGAG
CCGTACAGGTCACAGATCCTCGACTACCTGTTCAAGCCAAATTTCGGTGCC
TCCCTTCATATCCTGAAAGTGGAAATCGGTGGAGATGGACAGACTACCGAC
GGAACGGAGCCCTCCCACATGCATTACGCCCTGGACGAAAATTTCTTCCGG
GGCTACGAGTGGTGGCTGATGAAGGAGGCCAAGAAGCGGAACCCGAACATC
ATCCTGATGGGACTCCCTTGGTCCTTCCCCGGCTGGATCGGAAAGGGATTC
AACTGGCCCTACGTGAACCTCCAGCTTACCGCCTACTACATCATGACTTGG
ATTGTGGGCGCCAAGCATTACCACGACCTGGACATCGACTACATCGGCATT
TGGAACGAGCGGTCCTTTGACATCAACTACATTAAGGTGCTGAGGAGGATG
CTGAATTATCAGGGACTCGACAGAGTGAAGATTATTGCCTCGGACAACCTG
TGGGAGCCGATCTCGGCGTCCATGCTGCTTGATAGCGAGCTCCTCAAGGTC
ATCGACGTGATCGGAGCCCACTACCCTGGTACACACACCGTGAAGGACGCG
AAGCTGACCAAGAAGAAGCTGTGGTCCTCCGAGGACTTCTCCACCCTGAAC
AGCGATGTCGGAGCCGGATGCTTGGGACGGATCCTGAACCAGAACTACGTG
AACGGCTACATGACCGCCACCATTGCCTGGAACCTGGTGGCGTCTTACTAT
GAGCAACTCCCTTACGGACGCTGTGGGCTGATGACTGCCCAGGAACCATGG
AGCGGCCACTACGTGGTGGAGTCCCCTATCTGGGTCAGCGCCCACACCACC
CAGTTTACCCAGCCGGGATGGTACTACCTCAAGACCGTGGGGCACCTTGAG
AAGGGAGGATCCTACGTCGCTCTCACTGACGGGCTCGGCAACTTGACTATC
ATAGTGGAAACTATGTCCCACAAGCAGTCCGCATGCATTCGGCCCTTCTTG
CCGTACTTCAACGTGTCACGCCAGTTCGCCACTTTCGTGCTGAAGGGTTCG
TTCAGCGAGATCCCGGAGCTCCAAGTCTGGTACACTAAGCTGGGAAAGCCT
TCAGAACGCTACCTCTTCAAGCAGCTGGACTCCCTGTGGCTGCTGGATTCA
TCATCGACCTTCACCCTGGAACTGCAGGAAGATGAAATCTTCACCCTGACC
ACTCTGACTGTGGGCAGCAAGGGCTCGTATCCGCTCCCGCCGAAGTCGGAG
CCCTTTCCCCAAATCTACGAAGATGACTTCGACGTGGACTATCCCTTCTTC
```

-continued

TCGGAAGCCCCAAACTTCGCTGATCAAACCGGAGTGTTTGAGTATTTCACC

AACATTGAGGACCCCGGAGAACACAGATTCACGCTGCGCCAAGTGCTCAAC

CAGCGCCCCATCACCTGGGCCGCTGATGCCTACAACACCATTTCCATCATT

GGGGACTACAAATGGTCGAACCTGACCGTGCGCTGCGACGTGTACATCGAA

ACCCCCGAAAAGGGCGGCGTGTTCATCGCTGGCCGGGTCAACAAGGGGGGG

ATTCTTATTAGATCCGCGAGGGGATCTTTTTCTGGATCTTCGCCAACGGG

ACTTACCGCGTGACCGGAGATCTGGCCGGCTGGGTGATCTACGCCCTGGGT

AGAGTGGACGTGACCGCGAAGAAATGGTACACTCTGACCCTGATTATCAAA

GGGCGGTTGAGCTCCGGCATGCTGAACGGGAAAACTGTCTGGAAAAACATC

CCAGTGTCATTCCCTAAGAACGGATGGGCCGCCATCGGAACTCACAGCTTT

GAGTTCGCCCAGTTTGATAACTTTCATGTCGAAGCGACCCGCTAATGACCT

AGGGATGGCCGCGGGGATCCAGACATGATAAGATACATTGATGAGTTTGGA

CAAACCACAACTAGAATGCAGTGAAAAAAATGCTTTATTTGTGAAATTTGT

GATGCTATTGCTTTATTTGTAACCATTATAAGCTGCAATAAACAAGTTAAC

AACAACAATTTAGCAGGCATGCTGGGGAGAGATCTAGGAACCCCTAGTGAT

GGAGTTGGCCACTCCCTCTCTGCGCGCTCGCTCGCTCACTGAGGCCGCCCG

GGCAAAGCCCGGGCGTCGGGCGACCTTTGGTCGCCCGGCCTCAGTGAGCGA

GCGAGCGCGCAGAGAGGGAGTGGCCAACCCCCCCCCCCCCCCC.

In some embodiments, the expression cassette comprise, consists essentially of, or consists of the nucleotide sequence of SEQ ID NO:10 or a sequence at least about 70% identical thereto, e.g., at least about 70, 75, 80, 85, 90, 91, 92, 93, 94, 95, 96, 97, 98, or 99% identical thereto.

```
Human GALC expression cassette with JeT/spA
                                    SEQ ID NO: 10
Gggcggagttagggcggagccaatcagcgtgcgccgttccgaaagttgcct tttatggctgggcggagaatgggcggtgaacgccgatgattatataaggac gcgccgggtgtggcacagctagttccgtcgcagccgggatttgggtcgcgg ttcttgtttgttccggaaagccaccATGGCTGAGTGGCTCCTTAGCGCGAG

CTGGCAGCGGAGAGCCAAGGCAATGACAGCGGCGGCGGGCTCCGCCGGACG

CGCTGCCGTCCCTCTGTTGCTCTGTGCGTTGCTGGCACCGGGTGGAGCGTA

TGTGCTTGATGATTCGGACGGACTCGGTAGAGAATTTGACGGAATCGGAGC

GGTCAGCGGTGGAGGAGCGACGAGCCGCCTGCTCGTGAACTATCCCGAACC

CTACCGATCCCAGATTCTGGACTACCTTTTCAAACCTAACTTCGGCGCAAG

CCTTCACATCCTCAAGGTGGAGATCGGTGGGGACGGTCAGACCACAGACGG

TACGGAACCATCGCACATGCACTATGCGCTCGACGAAAACTACTTTAGAGG

GTATGAGTGGTGGCTGATGAAAGAGGCCAAAAAGCGGAATCCGAATATCAC

TCTCATTGGTTTGCCGTGGAGCTTCCCCGGCTGGCTGGGGAAGGGGTTCGA

CTGGCCCTATGTGAACCTTCAACTGACAGCGTATTACGTGGTCACATGGAT

TGTCGGGGCGAAGAGGTATCATGACTTGGATATCGACTATATTGGTATCTG

GAACGAGAGATCCTACAACGCAAACTACATCAAAATCCTTAGAAAGATGTT

GAATTATCAGGGGCTGCAGAGAGTCAAAATCATCGCATCCGACAATCTTTG
```

GGAATCGATCTCAGCGTCAATGCTCCTCGACGCGGAACTGTTTAAAGTGGT

GGATGTCATTGGGCGCATTACCCGGGAACACACTCGGCGAAAGACGCAAA

GTTGACGGGGAAGAAATTGTGGTCGAGCGAGGATTTTTCCACTCTTAATTC

GGATATGGGGCAGGGTGTTGGGGAAGAATTCTGAACCAGAACTATATCAA

CGGGTATATGACCTCGACGATCGCCTGGAATCTTGTGGCATCCTACTACGA

GCAGCTGCCTTACGGGAGGTGCGGTCTTATGACAGCGCAGGAGCCCTGGTC

GGGACATTACGTCGTCGAGAGCCCCGTATGGGTATCAGCCCACACGACCCA

GTTTACACAGCCGGGCTGGTATTACCTTAAGACGGTGGGCCATCTTGAGAA

GGGAGGTAGCTATGTCGCGCTGACGGATGGCTTGGGTAATTTGACAATCAT

CATTGAAACATATGTCGCATAAACACTCAAAGTGCATTCGCCCTTTTCTGCC

CTATTTCAACGTCAGCCAGCAATTTGCGACGTTTGTGCTTAAGGGATCGTT

TTCGGAGATTCCCGAACTTCAGGTCTGGTACACGAAACTTGGAAAGACGTC

AGAAAGGTTCCTTTTCAAGCAGTTGGACTCGCTCTGGCTTTTGGATAGCGA

CGGATCGTTCACTCTGTCCTTGCACGAGGATGAGTTGTTCACGCTCACTAC

CCTCACCACTGGCAGAAAGGGCTCCTACCCGTTGCCCCCGAAAAGCCAGCC

GTTTCCTTCAACTTATAAGGATGACTTTAATGTCGATTACCCATTCTTCTC

GGAGGCCCCGAATTTTGCCGACCAAACAGGAGTATTTGAATACTTCACGAA

CATCGAGGACCCGGGGGAGCACCATTTCACTCTGAGACAAGTGTTGAACCA

AAGGCCGATTACTTGGGCAGCCGATGCCAGCAATACCATTTCGATTATCGG

AGACTATAACTGGACAAACTTGACCATCAAATGCGATGTCTATATCGAAAC

GCCTGATACAGGGGGTGTGTTCATCGCTGGTCGCGTAAACAAAGGGGGAAT

TTTGATCCGCTCAGCTAGAGGGATCTTCTTTTGGATTTTCGCGAACGGAAG

CTACCGCGTGACGGGAGACTTGGCGGGATGGATCATCTACGCCCTGGGTCG

CGTGGAGGTAACAGCGAAAAAGTGGTACACGTTGACCTTGACAATTAAGGG

GCACTTCACGTCCGGGATGCTGAACGACAAGAGCCTCTGGACGGACATCCC

CGTGAATTTCCCCAAAAACGGGTGGGCAGCAATTGGGACGCACTCCTTTGA

ATTTGCGCAATTCGACAACTTTTTGGTAGAGGCTACGCGGaggcctAATAA

AGAGCTCAGATGCATCGATCAGAGTGTGTTGGTTTTTTGTGTG.

In some embodiments, the expression cassette comprise, consists essentially of, or consists of the nucleotide sequence of SEQ ID NO:11 or a sequence at least about 70% identical thereto, e.g., at least about 70, 75, 80, 85, 90, 91, 92, 93, 94, 95, 96, 97, 98, or 99% identical thereto.

```
Canine GALC expression cassette with JeT/spA
                                    SEQ ID NO: 11
gggcggagttagggcggagccaatcagcgtgcgccgttccgaaagttgcct tttatggctgggcggagaatgggcggtgaacgccgatgattatataaggac gcgccgggtgtggcacagctagttccgtcgcagccgggatttgggtcgcgg ttcttgtttgttccggaaagccaccATGACCGCAGCCGCAGGATCTGCAGG

CCATGCTGCGGTGCCCCTGTTGTTGTGTGCCCTTCTGGTCCCTGGCGGAGC

TTACGTGCTGGACGACTCCGACGGTTTGGGCCGGGAGTTCGACGGAGTGGG

AGCTGTCTCCGGTGGTGGAGCGACCAGCAGACTCCTCGTGAACTACCCGGA
```

-continued

```
GCCGTACAGGTCACAGATCCTCGACTACCTGTTCAAGCCAAATTTCGGTGC

CTCCCTTCATATCCTGAAAGTGGAAATCGGTGGAGATGGACAGACTACCGA

CGGAACGGAGCCCTCCCACATGCATTACGCCCTGGACGAAAATTTCTTCCG

GGGCTACGAGTGGTGGCTGATGAAGGAGGCCAAGAAGCGGAACCCGAACAT

CATCCTGATGGGACTCCCTTGGTCCTTCCCCGGCTGGATCGGAAAGGGATT

CAACTGGCCCTACGTGAACCTCCAGCTTACCGCCTACTACATCATGACTTG

GATTGTGGGCGCCAAGCATTACCACGACCTGGACATCGACTACATCGGCAT

TTGGAACGAGCGGTCCTTTGACATCAACTACATTAAGGTGCTGAGGAGGAT

GCTGAATTATCAGGGACTCGACAGAGTGAAGATTATTGCCTCGGACAACCT

GTGGGAGCCGATCTCGGCGTCCATGCTGCTTGATAGCGAGCTCCTCAAGGT

CATCGACGTGATCGGAGCCCACTACCCTGGTACACACACCGTGAAGGACGC

GAAGCTGACCAAGAAGAAGCTGTGGTCCTCCGAGGACTTCTCCACCCTGAA

CAGCGATGTCGGAGCCGGATGCTTGGGACGGATCCTGAACCAGAACTACGT

GAACGGCTACATGACCGCCACCATTGCCTGGAACCTGGTGGCGTCTTACTA

TGAGCAACTCCCTTACGGACGCTGTGGGCTGATGACTGCCCAGGAACCATG

GAGCGGCCACTACGTGGTGGAGTCCCCTATCTGGGTCAGCGCCCACACCAC

CCAGTTTACCCAGCCGGGATGGTACTACCTCAAGACCGTGGGGCACCTTGA

GAAGGGAGGATCCTACGTCGCTCTCACTGACGGGCTCGGCAACTTGACTAT

CATAGTGGAAACTATGTCCCACAAGCAGTCCGCATGCATTCGGCCCTTCTT

GCCGTACTTCAACGTGTCACGCCAGTTCGCCACTTTCGTGCTGAAGGGTTC

GTTCAGCGAGATCCCGGAGCTCCAAGTCTGGTACACTAAGCTGGGAAAGCC

TTCAGAACGCTACCTCTTCAAGCAGCTGGACTCCCTGTGGCTGCTGGATTC

ATCATCGACCTTCACCCTGGAACTGCAGGAAGATGAAATCTTCACCCTGAC

CACTCTGACTGTGGGCAGCAAGGGCTCGTATCCGCTCCCGCCGAAGTCGGA

GCCCTTTCCCCAAATCTACGAAGATGACTTCGACGTGGACTATCCCTTCTT

CTCGGAAGCCCCAAACTTCGCTGATCAAACCGGAGTGTTTGAGTATTTCAC

CAACATTGAGGACCCCGGAGAACACAGATTCACGCTGCGCCAAGTGCTCAA

CCAGCGCCCCATCACCTGGGCCGCTGATGCCTACAACACCATTTCCATCAT

TGGGGACTACAAATGGTCGAACCTGACCGTGCGCTGCGACGTGTACATCGA

AACCCCCGAAAAGGGCGGCGTGTTCATCGCTGGCCGGGTCAACAAGGGGGG

GATTCTTATTAGATCCGCGAGGGGATCTTTTTCTGGATCTTCGCCAACGG

GACTTACCGCGTGACCGGAGATCTGGCCGGCTGGGTGATCTACGCCCTGGG

TAGAGTGGACGTGACCGCGAAGAAATGGTACACTCTGACCCTGATTATCAA

AGGGCGGTTGAGCTCCGGCATGCTGAACGGGAAAACTGTCTGGAAAAACAT

CCCAGTGTCATTCCCTAAGAACGGATGGGCCGCCATCGGAACTCACAGCTT

TGAGTTCGCCCAGTTTGATAACTTTCATGTCGAAGCGACCCGCaggcctAA

TAAAGAGCTCAGATGCATCGATCAGAGTGTGTTGGTTTTTTGTGTG.
```

A further aspect of the invention relates to a vector comprising the polynucleotide or the expression cassette of the invention. Suitable vectors include, but are not limited to, a plasmid, phage, viral vector (e.g., an AAV vector, an adenovirus vector, a herpesvirus vector, an alphavirus vector, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat). In some embodiments, the vector is a delivery vehicle such as a particle (e.g., a microparticle or nanoparticle) or a liposome to which the expression cassette is attached or in which the expression cassette is embedded. The vector may be any delivery vehicle suitable to carry the expression cassette into a cell.

In some embodiments, the vector is a viral vector, e.g., an AAV vector. The AAV vector may be any AAV serotype, e.g., AAV9, AAVrh10, AAVOlig001, or any AAV serotype as listed in Table 1. In some embodiments, the AAV vector may comprise wild-type capsid proteins. In other embodiments, the AAV vector may comprise a modified capsid protein with altered tropism compared to a wild-type capsid protein, e.g., a modified capsid protein is liver-detargeted or has enhanced tropism for particular cells.

In some embodiments, the vector is a single-stranded AAV (ssAAV) vector. In some embodiments, the vector is a self-complementary or duplexed AAV (scAAV) vector. scAAV vectors are described in international patent publication WO 01/92551 (the disclosure of which is incorporated herein by reference in its entirety). Use of scAAV to express the GALC ORF may provide an increase in the number of cells transduced, the copy number per transduced cell, or both.

An additional aspect of the invention relates to a transformed cell comprising the polynucleotide, expression cassette, and/or vector of the invention. In some embodiments, the polynucleotide, expression cassette, and/or vector is stably incorporated into the cell genome. The cell may be an in vitro, ex vivo, or in vivo cell.

Another aspect of the invention relates to a transgenic animal comprising the polynucleotide, expression cassette, vector, and/or the transformed cell of the invention. In some embodiments, the animal is a laboratory animal, e.g., a mouse, rat, rabbit, dog, monkey, or non-human primate.

A further aspect of the invention relates to a pharmaceutical formulation comprising the polynucleotide, expression cassette, vector, and/or transformed cell of the invention in a pharmaceutically acceptable carrier.

In a specific embodiment, the polynucleotide, expression cassette, vector, and/or transformed cell of the invention is isolated.

In another specific embodiment, the polynucleotide, expression cassette, vector, and/or transformed cell of the invention is purified.

Methods of Producing Virus Vectors

The present invention further provides methods of producing virus vectors. In one particular embodiment, the present invention provides a method of producing a recombinant AAV particle, comprising providing to a cell permissive for AAV replication: (a) a recombinant AAV template comprising (i) the polynucleotide or expression cassette of the invention, and (ii) an ITR; (b) a polynucleotide comprising Rep coding sequences and Cap coding sequences; under conditions sufficient for the replication and packaging of the recombinant AAV template; whereby recombinant AAV particles are produced in the cell. Conditions sufficient for the replication and packaging of the recombinant AAV template can be, e.g., the presence of AAV sequences sufficient for replication of the AAV template and encapsidation into AAV capsids (e.g., AAV rep sequences and AAV cap sequences) and helper sequences from adenovirus and/or herpesvirus. In particular embodiments, the AAV template comprises two AAV ITR sequences, which are located 5' and 3' to the polynucleotide of the invention, although they need not be directly contiguous thereto.

In some embodiments, the recombinant AAV template comprises an ITR that is not resolved by Rep to make duplexed AAV vectors as described in international patent publication WO 01/92551.

The AAV template and AAV rep and cap sequences are provided under conditions such that virus vector comprising the AAV template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell (e.g., a primate, canine, or human cell). As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) Curr. Top. Microbiol. Immun. 158:67).

As a further alternative, the rep/cap sequences may be stably incorporated into a cell.

Typically the AAV rep/cap sequences will not be flanked by the TRs, to prevent rescue and/or packaging of these sequences.

The AAV template can be provided to the cell using any method known in the art. For example, the template can be supplied by a non-viral (e.g., plasmid) or viral vector. In particular embodiments, the AAV template is supplied by a herpesvirus or adenovirus vector (e.g., inserted into the E1a or E3 regions of a deleted adenovirus). As another illustration, Palombo et al., (1998) J. Virology 72:5025, describes a baculovirus vector carrying a reporter gene flanked by the AAV TRs. EBV vectors may also be employed to deliver the template, as described above with respect to the rep/cap genes.

In another representative embodiment, the AAV template is provided by a replicating rAAV virus. In still other embodiments, an AAV provirus comprising the AAV template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus mini-plasmid that carries all of the helper genes that promote efficient AAV production as described by Ferrari et al., (1997) Nature Med. 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the AAV template. The AAV rep/cap sequences and/or the AAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the AAV template can be provided as a plasmid template.

In another illustrative embodiment, the AAV rep/cap sequences and adenovirus helper sequences are provided by a single adenovirus helper vector, and the AAV template is integrated into the cell as a provirus. Alternatively, the AAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The AAV template can be provided as a separate replicating viral vector. For example, the AAV template can be provided by an AAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by ITRs so that these sequences are not packaged into the AAV virions.

Zhang et al., ((2001) Gene Ther. 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) Gene Ther. 6:986 and WO 00/17377).

As a further alternative, the virus vectors of the invention can be produced in insect cells using baculovirus vectors to deliver the rep/cap genes and AAV template as described, for example, by Urabe et al., (2002) Human Gene Ther. 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV. Adenovirus mutants defective for late gene expression are known in the art (e.g., t100K and ts149 adenovirus mutants).

Methods of Using GALC Vectors

The present invention also relates to methods for delivering a GALC ORF to a cell or a subject to increase production of GALC, e.g., for therapeutic or research purposes in vitro, ex vivo, or in vivo. Thus, one aspect of the invention relates to a method of expressing a GALC open reading frame in a cell, comprising contacting the cell with the polynucleotide, expression cassette, and/or the vector of the invention, thereby expressing the GALC open reading frame in the cell. In some embodiments, the cell is an in vitro cell, an ex vivo cell, or an in vivo cell.

Another aspect of the invention relates to a method of expressing a GALC open reading frame in a subject, comprising delivering to the subject the polynucleotide, expression cassette, vector, and/or transformed cell of the invention, thereby expressing the GALC open reading frame in the subject. In some embodiments, the subject is an animal model of a disorder associated with aberrant GALC gene expression.

The invention further provides a method of treating a disorder associated with aberrant expression of a GALC gene or aberrant activity of a GALC gene product in a subject in need thereof, comprising delivering to the subject a therapeutically effective amount of the polynucleotide, expression cassette, vector, and/or transformed cell of the invention, thereby treating the disorder associated with aberrant expression of the GALC gene or aberrant activity of a GALC gene product in the subject. The invention provides a method of treating a disorder associated with aberrant expression of a GALC gene or aberrant activity of a GALC gene product in a subject in need thereof, comprising administering to the subject a therapeutically effective amount of the polynucleotide, the expression cassette, vector, and/or transformed cell of the invention, such that the GALC open reading frame is expressed in the subject. In some embodiments, the disorder associated with expression of the GALC gene or gene product is Krabbe disease (L e., globoid cell leukodystrophy).

The invention further provides a method of treating Krabbe disease (i.e., globoid cell leukodystrophy) in a subject in need thereof, comprising administering to the subject a therapeutically effective amount of the polynucleotide, the expression cassette, vector, and/or transformed cell of the invention, such that the GALC open reading frame is expressed in the subject.

In some embodiments, the methods of the present invention further comprise administering to the subject a bone marrow transplant (BMT), e.g., prior to administering the effective amount of a polynucleotide, expression cassette, vector, and/or transformed cell of the present invention. Techniques for performing BMT (referred to interchangeably as a hematopoietic stem cell transplant (HSCT)) are well known to those of skill in the art, and are routine for clinicians in the treatment of subjects (e.g., patients, e.g., canine and/or human patients) in need thereof. The skilled clinician can readily determine the proper regimen to be used for performing BMT based on factors including the age and condition of the subject, type of disease being treated, stage of the disease, patient size, and the like.

In certain embodiments, the polynucleotide, expression cassette, vector, and/or transformed cell is delivered to the subject, e.g., systemically (e.g., intravenously) or directly to the central nervous system (e.g., to the cerebrospinal fluid by intrathecal or intraventricular injection) of the subject. In some embodiments, the polynucleotide, expression cassette, vector, and/or transformed cell is delivered intravenously. In some embodiments, the polynucleotide, expression cassette, vector, and/or transformed cell is delivered intracerebroventricularly.

Recombinant virus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, primates, non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a polynucleotide including those described herein. As a further option, the subject can be a laboratory animal and/or an animal model of disease. Preferably, the subject is a canine or human.

In certain embodiments, the polynucleotide of the invention is administered to a subject in need thereof as early as possible in the life of the subject, e.g., as soon as the subject is diagnosed with aberrant GALC expression or activity or any of the above-mentioned diseases or disorders. In some embodiments, the polynucleotide is administered to a newborn subject, e.g., after newborn screening has identified aberrant GALC expression or activity. In some embodiments, the polynucleotide is administered to a fetus in utero, e.g., after prenatal screening has identified aberrant GALC expression or activity or the presence of one of the above-mentioned diseases or disorders. In some embodiments, the polynucleotide is administered to a subject as soon as the subject develops symptoms associated with aberrant GALC expression or activity or is suspected or diagnosed as having aberrant GALC expression or activity or one of the above-mentioned diseases or disorders. In some embodiments, the polynucleotide is administered to a subject before the subject develops symptoms associated with aberrant GALC expression or activity or disease/disorder, e.g., a subject that is suspected or diagnosed as having aberrant GALC expression or activity or one of the above-mentioned diseases or disorders but has not started to exhibit symptoms.

In particular embodiments, the present invention provides a pharmaceutical composition comprising a polynucleotide, expression cassette, vector, and/or transformed cell of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a GALC ORF to a cell in vitro. The polynucleotide, expression cassette, and/or vector of the invention may be introduced to the cells in the appropriate amount. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The cell(s) into which the polynucleotide, expression cassette, and/or vector of the invention, e.g., virus vector, can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). As still a further alternative, the cell may be a cancer or tumor cell. Moreover, the cells can be from any species of origin, as indicated above.

The polynucleotide, expression cassette, and/or vector of the invention, e.g., virus vector, may be introduced to cells in vitro for the purpose of administering the modified cell to a subject. In particular embodiments, the cells have been removed from a subject, the polynucleotide, expression cassette, and/or vector of the invention, e.g., virus vector, is introduced therein, and the cells are then replaced back into the subject. Methods of removing cells from subject for treatment ex vivo, followed by introduction back into the subject are known in the art (see, e.g., U.S. Pat. No. 5,399,346). Alternatively, the polynucleotide, expression cassette, and/or vector of the invention, e.g., virus vector, is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector ex vivo are administered to the subject in an effective amount in combination with a pharmaceutical carrier.

A further aspect of the invention is a method of administering the polynucleotide, expression cassette, and/or vector of the invention, e.g., virus vector, to a subject. In particular embodiments, the method comprises a method of delivering a GALC ORF to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$ transducing units or more, e.g., about $10^7$, $10^8$, $10^9$, $10^{10}$, $10^{11}$, $10^{12}$, $10^{13}$, $10^{14}$, or $10^{15}$ transducing units, yet more preferably about $10^{10}$, $10^{11}$, $10^{12}$, $10^{13}$, $10^{14}$, or $10^{15}$ transducing units. In some embodiments, the dose of total virus may be in the range of about $1\times10^{10}$, $1.5\times10^{10}$, $2\times10^{10}$, $2.5\times10^{10}$, $3\times10^{10}$, $3.5\times10^{10}$, $4\times10^{10}$, $4.5\times10^{10}$, $5\times10^{10}$, $5.5\times10^{10}$, $6\times10^{10}$, $6.5\times10^{10}$, $7\times10^{10}$, $7.5\times10^{10}$, $8\times10^{10}$, $8.5\times10^{10}$, $9\times10^{10}$, $9.5\times10^{10}$, $1\times10^{11}$, $1.5\times10^{11}$, $2\times10^{11}$, $2.5\times10^{11}$, $3\times10^{11}$, $3.5\times10^{11}$, $4\times10^{11}$, $4.5\times10^{11}$, $5\times10^{11}$, $5.5\times10^{11}$, $6\times10^{11}$, $6.5\times10^{11}$, $7\times10^{11}$, $7.5\times10^{11}$, $8\times10^{11}$, $8.5\times10^{11}$, $9\times10^{11}$, $9.5\times10^{11}$, $1\times10^{12}$, $1.5\times10^{12}$, $2\times10^{12}$, $2.5\times10^{12}$, $3\times10^{12}$, $3.5\times10^{12}$, $4\times10^{12}$, $4.5\times10^{12}$, $5\times10^{12}$, $5.5\times10^{12}$, $6\times10^{12}$, $6.5\times10^{12}$, $7\times10^{12}$, $7.5\times10^{12}$, $8\times10^{12}$, $8.5\times10^{12}$, $9\times10^{12}$, $9.5\times10^{12}$, $1\times10^{13}$, $1.5\times10^{13}$, $2\times10^{13}$, $2.5\times10^{13}$, $3\times10^{13}$, $3.5\times10^{13}$, $4\times10^{13}$, $4.5\times10^{13}$, $5\times10^{13}$, $5.5\times10^{13}$, $6\times10^{13}$, $6.5\times10^{13}$, $7\times10^{13}$, $7.5\times10^{13}$, $8\times10^{13}$, $8.5\times10^{13}$, $9\times10^{13}$, $9.5\times10^{13}$, $1\times10^{14}$, $1.5\times10^{14}$, $2\times10^{14}$, $2.5\times10^{14}$, $3\times10^{14}$, $3.5\times10^{14}$, $4\times10^{14}$, $4.5\times10^{14}$, $5\times10^{14}$, $5.5\times10^{14}$, $6\times10^{14}$, $6.5\times10^{14}$, $7\times10^{14}$, $7.5\times10^{14}$, $8\times10^{14}$, $8.5\times10^{14}$, $9\times10^{14}$, $9.5\times10^{14}$, $1\times10^{15}$, $1.5\times10^{15}$, $2\times10^{15}$, $2.5\times10^{15}$, $3\times10^{15}$, $3.5\times10^{15}$, $4\times10^{15}$, $4.5\times10^{15}$, $5\times10^{15}$, $5.5\times10^{15}$, $6\times10^{15}$, $6.5\times10^{15}$, $7\times10^{15}$, $7.5\times10^{15}$, $8\times10^{15}$, $8.5\times10^{15}$, $9\times10^{15}$, $9.5\times10^{15}$, $1\times10^{16}$, $1.5\times10^{16}$, $2\times10^{16}$, $2.5\times10^{16}$, $3\times10^{16}$, $3.5\times10^{16}$, $4\times10^{16}$, $4.5\times10^{16}$, $5\times10^{16}$, $5.5\times10^{16}$, $6\times10^{16}$, $6.5\times10^{16}$, $7\times10^{16}$, $7.5\times10^{16}$, $8\times10^{16}$, $8.5\times10^{16}$, $9\times10^{16}$, $9.5\times10^{16}$, or any value or range therein. In some embodiments, the dose of total virus may be in the range of about $2\times10^{11}$ to about $7.7\times10^{13}$. In some embodiments, the dose of total virus may be in the range of about $6.6\times10^{11}$ to about $3.5\times10^{12}$. In some embodiments, the dose of total virus may be in the range of about $1.4\times10^{10}$ to about $3.4\times10^{16}$. In some embodiments, the dose of virus per gram of actual or estimated brain weight may be in the range of about $1\times10^{10}$, $1.5\times10^{10}$, $2\times10^{10}$, $2.5\times10^{10}$, $3\times10^{10}$, $3.5\times10^{10}$, $4\times10^{10}$, $4.5\times10^{10}$, $5\times10^{10}$, $5.5\times10^{10}$, $6\times10^{10}$, $6.5\times10^{10}$, $7\times10^{10}$, $7.5\times10^{10}$, $8\times10^{10}$, $8.5\times10^{10}$, $9\times10^{10}$, $9.5\times10^{10}$, $1\times10^{11}$, $1.5\times10^{11}$, $2\times10^{11}$, $2.5\times10^{11}$, $3\times10^{11}$, $3.5\times10^{11}$, $4\times10^{11}$, $4.5\times10^{11}$, $5\times10^{11}$, $5.5\times10^{11}$, $6\times10^{11}$, $6.5\times10^{11}$, $7\times10^{11}$, $7.5\times10^{11}$, $8\times10^{11}$, $8.5\times10^{11}$, $9\times10^{11}$, $9.5\times10^{11}$, $1\times10^{12}$, $1.5\times10^{12}$, $2\times10^{12}$, $2.5\times10^{12}$, $3\times10^{12}$, $3.5\times10^{12}$, $4\times10^{12}$, $4.5\times10^{12}$, $5\times10^{12}$, $5.5\times10^{12}$, $6\times10^{12}$, $6.5\times10^{12}$, $7\times10^{12}$, $7.5\times10^{12}$, $8\times10^{12}$, $8.5\times10^{12}$, $9\times10^{12}$, $9.5\times10^{12}$, $1\times10^{13}$, $1.5\times10^{13}$, $2\times10^{13}$, $2.5\times10^{13}$, $3\times10^{13}$, $3.5\times10^{13}$, $4\times10^{13}$, $4.5\times10^{13}$, $5\times10^{13}$, $5.5\times10^{13}$, $6\times10^{13}$, $6.5\times10^{13}$, $7\times10^{13}$, $7.5\times10^{13}$, $8\times10^{13}$, $8.5\times10^{13}$, $9\times10^{13}$, $9.5\times10^{13}$, $1\times10^{14}$, $1.5\times10^{14}$, $2\times10^{14}$, $2.5\times10^{14}$, $3\times10^{14}$, $3.5\times10^{14}$, $4\times10^{14}$, $4.5\times10^{14}$, $5\times10^{14}$, $5.5\times10^{14}$, $6\times10^{14}$, $6.5\times10^{14}$, $7\times10^{14}$, $7.5\times10^{14}$, $8\times10^{14}$, $8.5\times10^{14}$, $9 \times 10^{14}$, $9.5 \times 10^{14}$, $1 \times 10^{15}$, $1.5 \times 10^{15}$, $2 \times 10^{15}$, $2.5 \times 10^{15}$, $3 \times 10^{15}$, $3.5 \times 10^{15}$, $4 \times 10^{15}$, $4.5 \times 10^{15}$, $5 \times 10^{15}$, $5.5 \times 10^{15}$, $6 \times 10^{15}$, $6.5 \times 10^{15}$, $7 \times 10^{15}$, $7.5 \times 10^{15}$, $8 \times 10^{15}$, $8.5 \times 10^{15}$, $9 \times 10^{15}$, $9.5 \times 10^{15}$, $1 \times 10^{16}$, $1.5 \times 10^{16}$, $2 \times 10^{16}$, $2.5 \times 10^{16}$, $3 \times 10^{16}$, $3.5 \times 10^{16}$, $4 \times 10^{16}$, $4.5 \times 10^{16}$, $5 \times 10^{16}$, $5.5 \times 10^{16}$, $6 \times 10^{16}$, $6.5 \times 10^{16}$, $7 \times 10^{16}$, $7.5 \times 10^{16}$, $8 \times 10^{16}$, $8.5 \times 10^{16}$, $9 \times 10^{16}$, $9.5 \times 10^{16}$, or any value or range therein. In some embodiments, the dose of virus per actual or estimated brain weight may be in the range of about $2 \times 10^{11}$ to about $7.7 \times 10^{13}$. In some embodiments, the dose of virus per actual or estimated brain weight may be in the range of about $6.6 \times 10^{11}$ to about $3.5 \times 10^{12}$. In some embodiments, the dose of virus per actual or estimated brain weight may be in the range of about $1.4 \times 10^{10}$ to about $3.4 \times 10^{16}$. Doses and virus titer transducing units may be calculated as vector or viral genomes (vg).

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or a near a tumor or a lymph node). The most suitable route in any given case will depend on the nature and severity of the condition being treated and on the nature of the particular vector that is being used.

In some embodiments, the viral vector is administered to the CNS, the peripheral nervous system, or both.

In some embodiments, the viral vector is administered directly to the CNS, e.g., the brain or the spinal cord. Direct administration can result in high specificity of transduction of CNS cells, e.g., wherein at least 80%, 85%, 90%, 95% or more of the transduced cells are CNS cells. Any method known in the art to administer vectors directly to the CNS can be used. The vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The vector may also be administered to different regions of the eye such as the retina, cornea or optic nerve. The vector may be delivered into the cerebrospinal fluid (e.g., by lumbar puncture) for more disperse administration of the vector.

The delivery vector may be administered to the desired region(s) of the CNS by any route known in the art, including but not limited to, intrathecal, intracerebral, intraventricular, intranasal, intra-aural, intra-ocular (e.g., intravitreous, sub-retinal, anterior chamber) and peri-ocular (e.g., sub-Tenon's region) delivery or any combination thereof.

The delivery vector may be administered in a manner that produces a more widespread, diffuse transduction of tissues, including the CNS, the peripheral nervous system, and/or other tissues.

Typically, the viral vector will be administered in a liquid formulation by direct injection (e.g., stereotactic injection) to the desired region or compartment in the CNS and/or other tissues. In some embodiments, the vector can be delivered via a reservoir and/or pump. In other embodiments, the vector may be provided by topical application to the desired region or by intra-nasal administration of an aerosol formulation. Administration to the eye or into the ear may be by topical application of liquid droplets. As a further alternative, the vector may be administered as a solid, slow-release formulation. Controlled release of parvovirus and AAV vectors is described by international patent publication WO 01/91803.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 μg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharm. Res.* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

EXAMPLES

Example 1: Similarities Between Rodent, Macaque, Canine, and Human GALC

Gene therapy intervention for infantile Krabbe disease is proposed with the following advantages: the procedure is relatively safer and requires a shorter hospitalization, provides GALC enzyme to the tissue faster, sustained gene expression that lasts for a longer duration, provides better tissue distribution with potentially improved clinical benefits to the patients and thus expected to be more effective than HSCT in improving the quality of life and event-free survival. Treatment can be performed, e.g., with AAV9/GALC, with a codon-optimized GALC ORF for use in mice, rats, dogs, and humans. Similarities between the optimized human hGALCopt and wildtype GALC sequences in rodents, macaques, and dogs are shown in FIG. 1.

AAV9/GALC is a recombinant serotype 9 adeno-associated virus (AAV) encoding a human GALC transgene (hGALCopt). The codons are optimized to improve expression without any changes to the amino acid sequence. The final product consists of AAV9 capsids that are packaged with the single-stranded AAV genome comprising an AAV2 inverted terminal repeat (ITR), the "CAGGS" version of the "CBA" promoter (1.6 kb total CMV enhancer, chicken beta actin promoter and partial 5' untranslated region), codon-optimized human GALC DNA coding sequence, SV40 polyadenylation signal, and WT AAV2 ITR. Codon-optimization improves expression of the protein, but does not change the amino acid sequence.

Example 2: GALC Delivery in Neonatal Mice Improved Survival

A spontaneous autosomal recessive mutation observed in a mouse colony at the Jackson Laboratory was characterized and identified as twitcher (twi) displaying ataxia (twitching). Further studies in these mice established them as a relevant model of the human disorder (Kobayashi et al. 1980 Brain Res. 202:479-483; Moser 2006 Neurology 67(2):201-202). The twitcher mice have a complete loss of GALC activity and an accompanying accumulation of psychosine. On a pure C57B1/6 background the reported median survival of twitcher mice is around 42 days.

In this study, neonatal (P0-P1) $GALC^{-/-}$ "twitcher" mice received the murine AAV9/mGALC via multiple routes of administration simultaneously (intracranial, intrathecal, and intravenous) at a total dose of $4.2\times10^{11}$ vg per mouse. Treated mice had a median survival of 263 days (maximum 484 days) compared to untreated $GALC^{-/-}$ cohort that had a median survival of 44 days (maximum 47 days) (Marshall et al. 2018 Mol. Ther. 26(3):874-889). Analysis done at P40 evaluated the therapy compared to untreated mice. Since all the untreated mice died by P47 all analyses done in treated mice that aged beyond that point were compared to wild type mice. The treated $GALC^{-/-}$ cohort had improved clinical scoring, body weight, motor function, endurance and general locomotion compared to untreated cohorts at P40 testing. On some of the functional assays the performance of the treated GALC$^{-/-}$ mice was comparable to wild type cohorts during P100-P200 time points. Gene therapy significantly improved GALC activity and concurrently reduced the psychosine accumulation in the brain, spinal cord and sciatic nerve at P40. This trend was maintained in treated mice until they aged to humane endpoint of either limb paralysis or predetermined rate of weight loss.

Example 3: GALC Delivery in PND11 Mice Improved Histology and Survival

GALC$^{-/-}$ "twitcher" mice received a single intrathecal injection of AAV9/mGALC into the lumbar cistern at PND11, and then they were monitored for survival and biochemical/histological improvement relative to untreated control mice (Karumuthil-Melethil et al. 2016 J. Neurosci. Res. 94(11):1138-1151). Survival of the treated mice was extended 79 days when receiving a dose of $2 \times 10^{11}$ vg total where untreated controls were dead by 40 days. Death in these cohorts was a predefined humane endpoint set to a loss in 20% body weight. A separate group of mice were sacrificed at PND35 for investigation of vector biodistribution, GALC activity, psychosine levels, and histological myelination improvements (FIG. 2). These data were all performed at the dose of $2 \times 10^{11}$ vg (Karumuthil-Melethil et al. 2016). The low dose ($2 \times 10^{11}$) in PND11 mice by the IT-L route improved the pathology and reduced psychosine levels, but did not restore them to baseline levels.

A long-term follow-up study was conducted separately to evaluate $8 \times 310^{11}$ vg dose (4× higher than above) of AAV9/mGALC in twitcher mice by IT-L administration. Seven treated twitcher mice were followed in this study, only weight and survival were assessed in these mice Death in these cohorts was a predefined humane endpoint set to a loss in 20% body weight. Compared to the cohort at $2 \times 10^{11}$ vg, the treated mice had an extended median lifespan (40 days for untreated, 79 days at $2 \times 10^{11}$ vg, and 140 days at $8 \times 10^{11}$ vg). The improved survival of the mice receiving $8 \times 10^{11}$ vg was statistically significant compared to untreated mice or mice receiving $2 \times 10^{11}$ vg (P<0.0001 for each, Mantel-Cox Logrank). The high dose of $8 \times 10^{11}$ correlates to a dose of approximately $2.7 \times 10^{12}$ vg per gram brain weight, which would extrapolate to a dose of $7.7 \times 10^{13}$ vg in a PND14 Krabbe dog and $1.1 \times 10^{15}$ vg in a newborn human.

Example 4: GALC Delivery in Krabbe Dogs Improved Survival and Clinical Disease

Krabbe/GLD in dogs is a relevant model for evaluation of safety, efficacy and is amenable to the clinical route of AAV9/GALC administration. Krabbe is hereditary in dogs and the disease progression closely recapitulates human manifestation (Victoria et al. 1996 Genomics 33(3):457-462). Dogs are the only naturally occurring disease model that results from a missense mutation in the GALC gene, (c.473A>C, p.158Y>S), which is inherited as an autosomal recessive trait. Transient transfection of COS-1 cells with the mutant canine GALC cDNA results in no GALC activity in transfected cells, indicating that mutant protein is not functional (Victoria et al 1996). Signs in impacted dogs begin at 4 weeks of age with pelvic limb weakness, thoracic limb dysmetria, and head tremor. Disease then progresses to include ataxia, pelvic limb paresis, urinary incontinence, and loss of hearing by 12 weeks of age. Pelvic limb paralysis warrants euthanasia at 16 weeks (Bradbury et al. 2016 J. Neurosci. Res. 94(11):1007-1017).

In dogs with Krabbe, demyelination reduces motor and sensory conduction velocities in peripheral nerves and can be assayed via nerve conduction studies (Bradbury et al. 2016 J. Neurosci. Res.; McGowan et al. 2000 J. Comput. Assist. Tomogr. 24(2):316-321). Brain stem auditory evoked response (BAER) measurements show increased conduction time. Magnetic resonance imaging (MRI) of the brain shows T2-weighted bilaterally symmetrical increases in signal intensity of the corona radiata, corpus callosum, centrum semiovale, internal capsule and cerebellar white matter compared to a normal, age-matched control dogs. Cerebral ventricles are dilated and sulci are widened indicating cerebral atrophy in Krabbe dogs. Magnetic resonance spectroscopy (MRS) reveals a decrease in N-acetylaspartate indicative of neuronal loss, and increases in choline indicative of abnormal myelin turnover (Vite and Cross 2011 Vet. Radiol. Ultrasound. 52(1 Supp11):S23-31). Diffusion tensor imaging (DTI) of the canine Krabbe brain shows substantial decreases in fractional anisotropy, increases in radial diffusivity, and increases in apparent diffusion coefficient in the internal capsule, corona radiata, and corpus callosum when compared to normal dog (Bradbury et al. 2016 Neuroradiol. J. 29(6):417-424; Li et al. 2018 Neuroradiol. J. 31(2):168-176)). Consistent with imaging findings, histologic evaluation shows severe loss of myelin, globoid cell accumulation, and neuroinflammation in the white matter (Bradbury et al. 2016 J. Neurosci. Res.; Bradbury et al. 2018 Hum. Gene Ther. 29(7):785-801).

Brain biochemistry reveals decreased GALC activity and elevated psychosine levels (Bradbury et al. 2016 J. Neurosci. Res.; Wenger et al. 1999 J. Hered. 90(1):138-142). Psychosine is significantly elevated in the serum and CSF at 2 and 4 weeks of age, respectively, and increases steadily over their lifetime in Krabbe dogs. Importantly, psychosine concentration strongly correlates with disease severity. Galactosylceramide, glucosylceramide, and lactosylceramide are also found to be elevated in the CSF of Krabbe dogs and increase with age. The combination of longitudinal electrodiagnostic (nerve conduction velocity and BAER), neuroimaging, and biochemical markers of disease now serve as strong predictive outcome measures in preclinical studies utilizing the canine Krabbe model.

In this study, presymptomatic and symptomatic dogs were administered a single dose of AAV9/cGALC into intrathecal CSF via the cisterna magna injection. Canine Krabbe is the closest in pathology, clinical presentation and progression to replicating Krabbe in humans. The dogs received an immunosuppression regimen, being administered with oral prednisolone for 4 months with a 2 week taper. The study cohort assignment, numbers, age and dose levels tested are listed in Table 4.

TABLE 4

Treatment cohorts in Krabbe dogs

| GALC genotype | Dosing age (weeks) | Dosing route | No. of Dogs Male | No. of Dogs Female | Dose ($\times 10^{14}$ vg) Preclinical | Dose ($\times 10^{14}$ vg) Volume (mL) |
|---|---|---|---|---|---|---|
| -/- | 2 | — | 2 | 2 | — | — |
| -/- | 2 | IT-CM | 4* | 6* | 1 | 1 |
| -/- | 2 | IT-CM | 3 | 1 | 0.2 | 1 |
| -/- | 6 | IT-CM | 2 | 2 | 1 | 1 |

TABLE 4-continued

Treatment cohorts in Krabbe dogs

| GALC genotype | Dosing age (weeks) | Dosing route | No. of Dogs Male | No. of Dogs Female | Dose (×10¹⁴ vg) Preclinical | Volume (mL) |
|---|---|---|---|---|---|---|
| −/− | 6 | IT-CM | 2 | 2 | 0.2 | 1 |
| −/− | 3 | IT-L | 2 | 2 | 1 | 1 |

All dogs received oral prednisolone for immunosuppression.

Dogs received AAV9/cGALC at two dose levels (Table 4). For an interim analysis, 4 treated dogs were euthanized at 16 weeks of age (untreated dog lifespan), to evaluate histopathology, enzyme activity and psychosine accumulation. The remaining dogs will be monitored for the therapeutic efficacy and safety long-term.

The Krabbe dogs receiving immunosuppression regimen alone had a disease course indistinguishable from untreated dogs. They reached a humane endpoint at 11 to 16 weeks of age. Krabbe dogs that received the high dose at 2 weeks of age had no clinical evidence of disease at 16 weeks of age based on physical and neurological evaluation. The rest of the dogs being followed long-term in this cohort are currently 13-57 weeks of age with no clinical evidence of disease. Of the dogs that received a lower dose at 2 weeks, 2 of the 3 that were dosed are showing signs of mild to moderate ataxia. Of the dogs that were administered a higher dose at 6 weeks age following the onset of symptoms, 2 of the 3 are showing signs of mild to moderate pelvic limb ataxia.

Figure 3A:
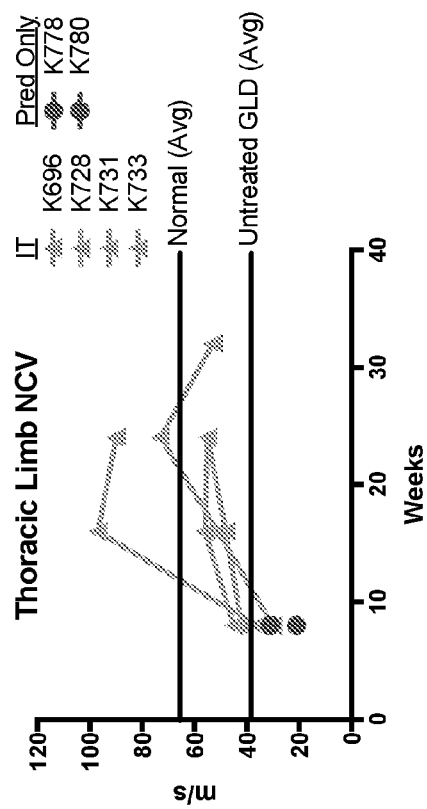
FIGS. 3A-3C show that nerve conduction velocity (NCV) is retained in AAV9/cGALC treated Krabbe dogs. Dogs received a single IT-CM AAV9/cGALC per the group assignment, untreated dogs were not dosed. NCV testing was repeated every 8 weeks following dose administration. Conduction was evaluated in pelvic limb (FIG. 3A), thoracic limb (FIG. 3B) and sensory nerve (FIG. 3C). Untreated (circles; n=2) or those administered high-dose at 2 weeks age (triangles; n=4) are plotted on the graph. Average NCV in wild type (Normal) and untreated dogs is indicated by black lines in the figure. Note: Untreated dogs only had one session as they reached humane endpoint and did not survive until the next session.
Figure 3C:
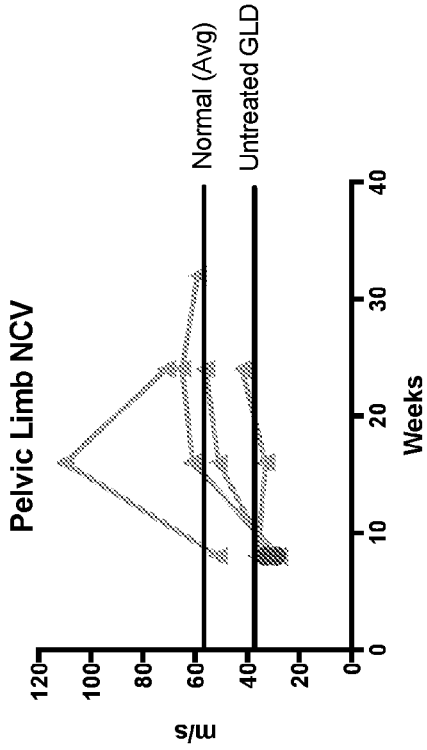
Figure 3B:
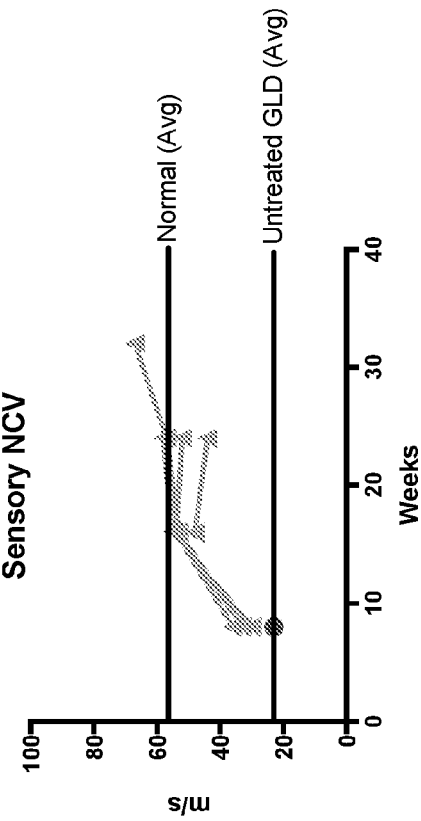

Clinical severity of the disease correlates well with the severity of demyelination in Krabbe and impacts the nerve conduction velocity (NCV) in humans and animals (Siddiqi et al. 2006 Neurology 67:263-267; Weimer et al. 2005 Muscle & Nerve 32:185-190). IT-CM delivery of AAV9/cGALC resulted in improved and sustained peripheral and sensory NCV. Peripheral NCV testing was performed on untreated Krabbe dogs at humane endpoint (14-19 weeks of age, n=6), normal age-matched control dogs (14-21 weeks, n=9), and AAV9-treated Krabbe dogs every 8 weeks. Motor NCVs were significantly decreased in untreated Krabbe dogs, indicative of demyelination, when compared to age-matched normal control dogs as measured in tibial (p=0.0093), sciatic (p=0.0021) and ulnar nerves (p=0.0134). Sensory NCV of the superficial radial nerve was also significantly reduced (p=0.0033) in untreated Krabbe dogs when compared to normal control dogs. Treated dogs improved their NCVs following AAV9/cGALC therapy treading toward the values seen in age matched controls and in some cases performing better (FIGS. 3A-3C). These findings suggest gene therapy improved myelination and thus the function in these nerves.

Figure 4:
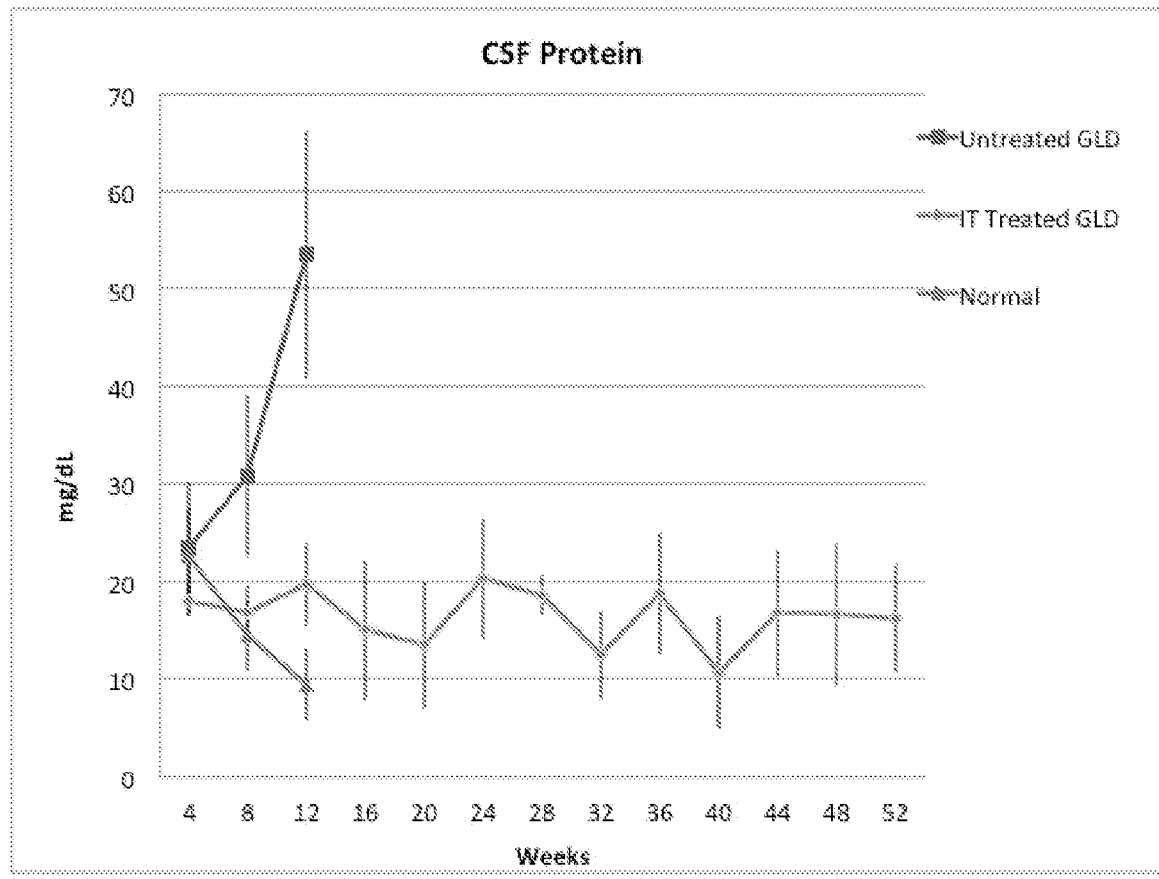
FIG. 4 shows AAV9/cGALC reduces CSF protein concentration in Krabbe dogs.

Protein concentration in the CSF is elevated in infants with Krabbe disease within the first weeks of life. A similar increase in CSF protein is seen with disease progression in untreated Krabbe dogs compared to normal age-matched control dogs. Recent evaluation of Krabbe dog CSF by two dimensional difference gel electrophoresis revealed that the source of elevation is likely due to inflammatory activity in the microglia and/or astrocytes. CNS disease progression in the ongoing IT-CM treated dogs was monitored by measuring CSF protein levels monthly. Compared to untreated Krabbe dogs, IT-CM treatment reduced levels of CSF protein (FIG. 4).

Figure 5:
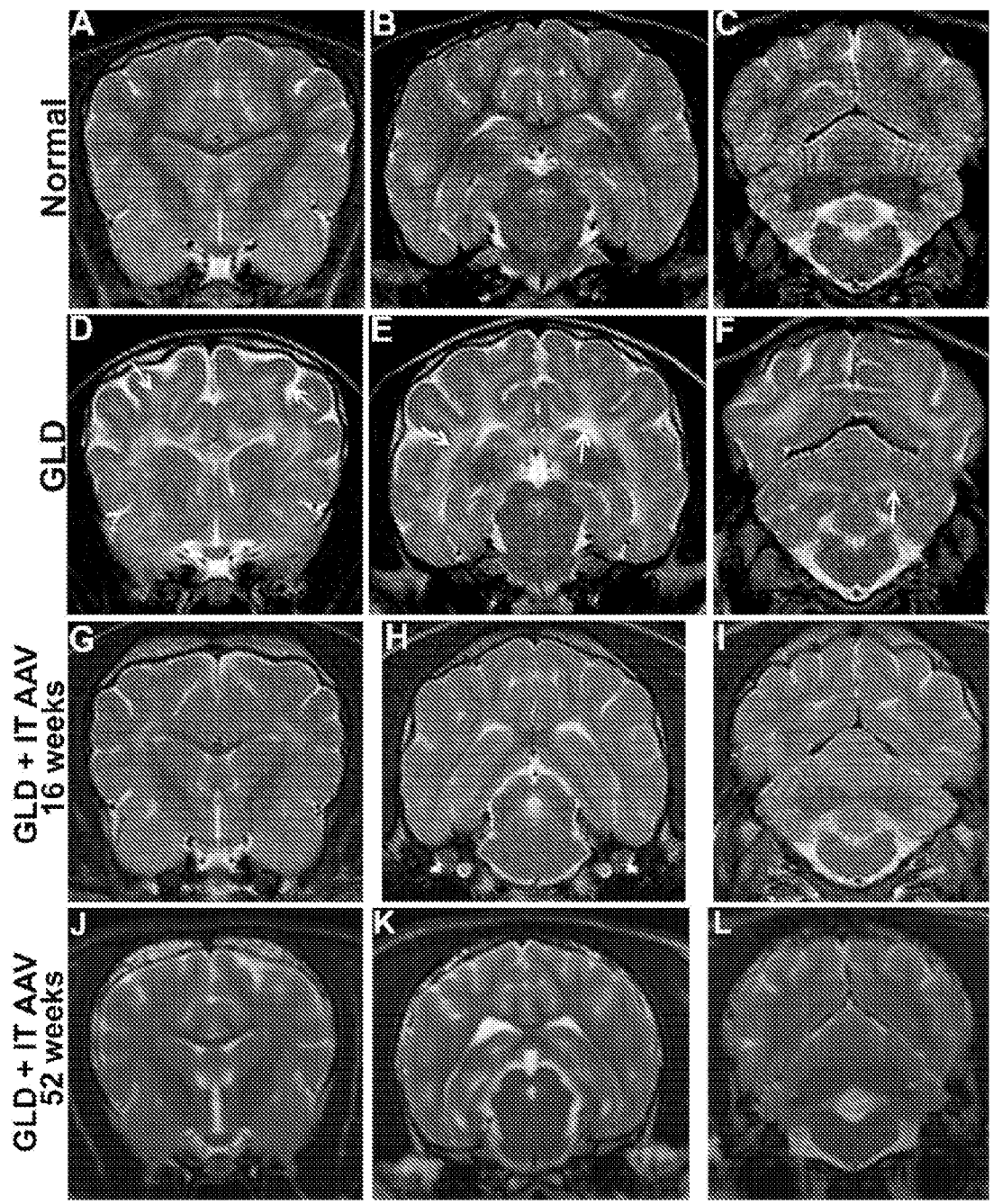
FIG. 5 shows that gene therapy preserves cerebral white matter. Brain MRIs are representative T2-weighed scans from one animal from each cohort. The brain of a Krabbe affected dogs shows T2-weighted bilaterally symmetrical increases in signal intensity of the corona radiata (FIG. 5 panel D, arrow), corpus callosum, centrum semiovale, internal capsule (FIG. 5 panel E, arrow), and cerebellar white matter (FIG. 5 panel F, arrow) when compared to a normal, age-matched control dogs (FIG. 5 panels A-C). Cerebral ventricles are dilated (FIG. 5 panel E, arrow) and sulci are widened (FIG. 5 panel D, arrow) indicating cerebral atrophy in Krabbe dogs. In contrast, 16 weeks after IT-CM delivery of AAV9-cGALC white matter signal remains normal at the corpus callosum and internal capsule, although isointensity is noted at the corona radiata and centrum semiovale. Cerebellar white matter is preserved. Ventricles and sulci remain within normal limits indicating attenuation of brain atrophy. Notably, stabilization of MRI changes is seen at 52 weeks of age (FIG. 5 panels J-L).

Magnetic Resonance Imaging (MRI) analysis in symptomatic infantile Krabbe patients showed abnormalities in T2 signal intensity of the cerebral white matter in periventricular/centrum semiovale, the dentate, cerebellar white matter, thalamus, and parietal-occipital (Abdelhalim et al. 2014 Pediatric Neurology 50:127-134). In canine models of Krabbe, there are areas of demyelination that are detected by MRI (McGowan et al. 2000). The brain of a Krabbe affected dogs shows T2-weighted bilaterally symmetrical increases in signal intensity of the corona radiata (FIG. 5 panel D, arrow), corpus callosum, centrum semiovale, internal capsule (FIG. 5 panel E, arrow), and cerebellar white matter (FIG. 5 panel F, arrow) when compared to a normal, age-matched control dogs (FIG. 5 panels A-C). Cerebral ventricles are dilated (FIG. 5 panel E, arrow) and sulci are widened (FIG. 5 panel D, arrow) indicating cerebral atrophy in Krabbe dogs. In contrast, 16 weeks after IT-CM delivery of AAV9-cGALC white matter signal remains normal at the corpus callosum and internal capsule, although isointensity is noted at the corona radiata and centrum semiovale. Cerebellar white matter is preserved. Ventricles and sulci remain within normal limits indicating attenuation of brain atrophy. Notably, stabilization of MRI changes is seen at 52 weeks of age (FIG. 5 panels J-L).

All references cited herein are incorporated herein by reference in their entireties and for all purposes to the same extent as if each individual publication or patent or patent application was specifically and individually indicated to be incorporated by reference in its entirety for all purposes.

The foregoing examples are illustrative of the present invention, and are not to be construed as limiting thereof. Although the invention has been described in detail with reference to preferred embodiments, variations and modifications exist within the scope and spirit of the invention as described and defined in the following claims.

What is claimed is:

1. A polynucleotide comprising a canine or human GALC open reading frame, wherein the GALC open reading frame is codon-optimized for expression in a canine or human cell, wherein said canine or human GALC open reading frame comprises the nucleotide sequence of SEQ ID NO:1 or SEQ ID NO:2, or a nucleotide sequence having at least about 90% identity thereto.

2. An expression cassette comprising the polynucleotide of claim 1.

3. The expression cassette of claim 2, wherein the canine or human GALC open reading frame is operably linked to a promoter and/or a polyadenylation signal.

4. The expression cassette of claim 3, wherein the promoter is a chicken beta actin promoter or a JeT promoter, and wherein the polyadenylation signal is a synthetic polyadenylation signal or an SV40 polyadenylation signal.

5. The expression cassette of claim 2, further comprising at least one adeno-associated virus (AAV) inverted terminal repeat (ITR).

6. The expression cassette of claim 5, wherein the expression cassette comprises two AAV ITRs.

7. The expression cassette of claim 2, wherein the expression cassette is a self-complementary AAV genome.

8. The expression cassette of claim 2, wherein the expression cassette comprises a promoter, the canine or human GALC open reading frame, and a polyadenylation site.

9. The expression cassette of claim 8, wherein the expression cassette comprises an AAV ITR, a promoter, the canine or human GALC open reading frame, a polyadenylation site, and an AAV ITR.

10. The expression cassette of claim 9, wherein the expression cassette comprises an AAV2 ITR, a CAGGS promoter, a canine GALC open reading frame, an SV40 polyadenylation site, and an AAV2 ITR.

11. The expression cassette of claim 9, wherein the expression cassette comprises an AAV2 ITR, a JeT promoter, a human GALC open reading frame, a synthetic polyadenylation site, and an AAV2 ITR.

12. The expression cassette of claim 9, wherein the expression cassette comprises an AAV2 ITR, a JeT promoter, a canine GALC open reading frame, a synthetic polyadenylation site, and an AAV2 ITR.

13. The expression cassette of claim 9, wherein the expression cassette comprises an AAV2 ITR, a CAGGS promoter, a human GALC open reading frame, an SV40 polyadenylation site, and an AAV2 ITR.

14. The expression cassette of claim 13, comprising the nucleotide sequence of one of SEQ ID NOs:8-11 or a sequence at least about 90% identical thereto.

15. A vector comprising the polynucleotide of claim 1.

16. The vector of claim 15, wherein the vector is an AAV vector.

17. The vector of claim 15, wherein the AAV vector is an AAV9, AAVrh10, AAVOlig001 vector.

18. A pharmaceutical composition comprising the vector of claim 15 in a pharmaceutically acceptable carrier.

19. A method of treating a disorder associated with aberrant expression of a GALC gene or aberrant activity of a GALC gene product in a subject in need thereof, comprising administering to the subject a therapeutically effective amount of the pharmaceutical composition of claim 18, such that the GALC open reading frame is expressed in the subject.

20. A method of treating Krabbe disease in a subject in need thereof, comprising administering to the subject a therapeutically effective amount of the pharmaceutical composition of claim 18, such that the GALC open reading frame is expressed in the subject.

21. The method of claim 20, further comprising:
administering to the subject a bone marrow transplant (BMT) prior to administering the effective amount of the pharmaceutical composition.

22. The method of claim 20, wherein the subject is a human.

23. The method of claim 20, wherein the subject is a dog.

24. The method of claim 20, wherein the pharmaceutical composition is delivered or administered to the nervous system of the subject.

25. The method of claim 24, wherein the pharmaceutical composition is delivered or administered by intrathecal, intracerebral, intracerebroventricular, intranasal, intra-aural, intra-ocular, or peri-ocular delivery, or any combination thereof.

26. A method of expressing a GALC open reading frame in a cell, comprising contacting the cell with the polynucleotide of claim 1, thereby expressing the GALC open reading frame in the cell.

* * * * *

UNITED STATES PATENT AND TRADEMARK OFFICE
CERTIFICATE OF CORRECTION

| | |
|---|---|
| PATENT NO. | : 12,359,181 B2 |
| APPLICATION NO. | : 17/416559 |
| DATED | : July 15, 2025 |
| INVENTOR(S) | : Gray et al. |

It is certified that error appears in the above-identified patent and that said Letters Patent is hereby corrected as shown below:

In the Specification

Column 2, Line 4: Please correct "(<1=12 months)" to read --(</=12 months)--

Column 4, Line 58: Please correct "theraPy" to read --therapy--

Column 18, Line 18: Please correct "CALC" to read --GALC--

Column 18, Line 20: Please correct "CALC" to read --GALC--

Column 33, Line 21: Please correct "Ela" to read --E1a--

Column 42, Line 54: Please correct "C57B1/6" to read --C57Bl/6--

Column 43, Line 44: Please correct "8×10''" to read --8×10$^{11}$--

Column 44, Line 20: Please correct "(1 Suppl1)" to read --(1 Suppl1)--

Column 45, Lines 33-34: Please remove the paragraph break between "in" and "Krabbe"

Signed and Sealed this
Twenty-first Day of October, 2025

John A. Squires
*Director of the United States Patent and Trademark Office*

SEQUENCE LISTING

<160> NUMBER OF SEQ ID NOS: 16

<210> SEQ ID NO 1
<211> LENGTH: 2055
<212> TYPE: DNA
<213> ORGANISM: Artificial
<220> FEATURE:
<223> OTHER INFORMATION: Human codon-optimized GALC open reading frame

<400> SEQUENCE: 1

```
atggctgagt ggctccttag cgcgagctgg cagcggagag ccaaggcaat gacagcggcg      60
gcgggctccg ccggacgcgc tgccgtccct ctgttgctct gtgcgttgct ggcaccgggt     120
```

```
ggagcgtatg tgcttgatga ttcggacgga ctcggtagag aatttgacgg aatcggagcg      180
gtcagcggtg gaggagcgac gagccgcctg ctcgtgaact atcccgaacc ctaccgatcc      240
cagattctgg actaccttt caaacctaac ttcggcgcaa gccttcacat cctcaaggtg       300
gagatcggtg gggacggtca gaccacagac ggtacggaac catcgcacat gcactatgcg      360
ctcgacgaaa actactttag agggtatgag tggtggctga tgaaagaggc caaaaagcgg      420
aatccgaata tcactctcat tggtttgccg tggagcttcc ccggctggct ggggaagggg      480
ttcgactggc cctatgtgaa ccttcaactg acagcgtatt acgtggtcac atggattgtc      540
ggggcgaaga ggtatcatga cttggatatc gactatattg gtatctggaa cgagagatcc      600
tacaacgcaa actacatcaa aatccttaga aagatgttga attatcaggg gctgcagaga      660
gtcaaaatca tcgcatccga caatctttgg aatcgatct cagcgtcaat gctcctcgac        720
gcggaactgt ttaaagtggt ggatgtcatt ggggcgcatt acccgggaac acactcggcg      780
aaagacgcaa agttgacggg gaagaaattg tggtcgagcg aggattttc cactcttaat       840 tcggatatgg gggcagggtg ttggggaaga attctgaacc agaactatat caacgggtat      900
atgacctcga cgatcgcctg gaatcttgtg gcatcctact acgagcagct gccttacggg      960
aggtgcggtc ttatgacagc gcaggagccc tggtcgggac attcgtcgt cgagagcccc     1020 gtatgggtat cagcccacac gacccagttt acacagccgg gctggtatta ccttaagacg     1080
gtgggccatc ttgagaaggg aggtagctat gtcgcgctga cggatggctt gggtaatttg     1140
acaatcatca ttgaaactat gtcgcataaa cactcaaagt gcattcgccc ttttctgccc    1200
tatttcaacg tcagccagca atttgcgacg tttgtgctta agggatcgtt ttcggagatt    1260
cccgaacttc aggtctggta cacgaaactt ggaaagacgt cagaaaggtt ccttttcaag     1320
cagttggact cgctctggct tttggatagc gacggatcgt tcactctgtc cttgcacgag     1380
gatgagttgt tcacgctcac tacctcacc actggcagaa agggctccta cccgttgccc     1440
ccgaaaagcc agccgtttcc ttcaacttat aaggatgact taatgtcga ttacccattc      1500 ttctcggagg ccccgaattt tgccgaccaa acaggagtat ttgaatactt cacgaacatc     1560
gaggacccgg gggagcacca tttcactctg agacaagtgt tgaaccaaag gccgattact     1620
tgggcagccg atgccagcaa taccatttcg attatcggag actataactg gacaaacttg      1680
accatcaaat gcgatgtcta tatcgaaacg cctgatacag ggggtgtgtt catcgctggt     1740
cgcgtaaaca aggggggaat tttgatccgc tcagctagag ggatcttctt ttggattttc     1800
gcgaacggaa gctaccgcgt gacgggagac ttggcgggat ggatcatcta cgccctgggt     1860
cgcgtggagg taacagcgaa aaagtggtac acgttgacct tgacaattaa gggcacttc      1920 acgtccggga tgctgaacga caagagcctc tggacggaca tccccgtgaa tttccccaaa     1980
aacgggtggg cagcaattgg gacgcactcc tttgaatttg cgcaattcga caacttttg      2040 gtagaggcta cgcgg                                                       2055
```

<210> SEQ ID NO 2
<211> LENGTH: 2007
<212> TYPE: DNA
<213> ORGANISM: Artificial
<220> FEATURE:
<223> OTHER INFORMATION: Canine codon-optimized GALC open reading frame

<400> SEQUENCE: 2

```
atgaccgcag ccgcaggatc tgcaggccat gctgcggtgc cctgttgtt gtgtgccctt       60
```

-continued

```
ctggtccctg gcggagctta cgtgctggac gactccgacg gtttgggccg ggagttcgac      120
ggagtgggag ctgtctccgg tggtggagcg accagcagac tcctcgtgaa ctacccggag      180
ccgtacaggt cacagatcct cgactacctg ttcaagccaa atttcggtgc ctcccttcat      240
atcctgaaag tggaaatcgg tggagatgga cagactaccg acggaacgga gccctcccac      300
atgcattacg ccctggacga aaatttcttc cggggctacg agtggtggct gatgaaggag      360
gccaagaagc ggaacccgaa catcatcctg atgggactcc cttggtcctt ccccggctgg      420
atcggaaagg gattcaactg cccctacgtg aacctccagc ttaccgccta ctacatcatg      480
acttggattg tgggcgccaa gcattaccac gacctggaca tcgactacat cggcatttgg      540
aacgagcggt cctttgacat caactacatt aaggtgctga ggaggatgct gaattatcag      600
ggactcgaca gagtgaagat tattgcctcg gacaacctgt gggagccgat ctcggcgtcc      660
atgctgcttg atagcgagct cctcaaggtc atcgacgtga tcggagccca ctaccctggt      720
acacacaccg tgaaggacgc gaagctgacc aagaagaagc tgtggtcctc cgaggacttc      780
tccaccctga acagcgatgt cggagccgga tgcttggac ggatcctgaa ccagaactac      840
gtgaacggct acatgaccgc caccattgcc tggaacctgg tggcgtctta ctatgagcaa      900
ctcccttacg gacgctgtgg gctgatgact gcccaggaac catggagcgg ccactacgtg      960
gtggagtccc ctatctgggt cagcgcccac accacccagt ttacccagcc gggatggtac     1020
tacctcaaga ccgtggggca ccttgagaag ggaggatcct acgtcgctct cactgacggg     1080
ctcggcaact tgactatcat agtggaaact atgtcccaca agcagtccgc atgcattcgg     1140 ccccttcttgc cgtacttcaa cgtgtcacgc cagttcgcca cttttcgtgct gaagggttcg     1200 ttcagcgaga tcccggagct ccaagtctgg tacactaagc tgggaaagcc ttcagaacgc     1260
tacctcttca gcagctgga ctccctgtgg ctgctggatt catcatcgac cttcaccctg     1320
gaactgcagg aagatgaaat cttcaccctg accactctga ctgtgggcag caagggctcg     1380
tatccgctcc cgccgaagtc ggagcccttt ccccaaatct acgaagatga cttcgacgtg     1440
gactatccct tcttctcgga agccccaaac ttcgctgatc aaaccggagt gtttgagtat     1500
ttcaccaaca ttgaggaccc cggagaacac agattcacgc tgcgccaagt gctcaaccag     1560
cgccccatca cctgggccgc tgatgcctac aacaccattt ccatcattgg ggactacaaa     1620
tggtcgaacc tgaccgtgcg ctgcgacgtg tacatcgaaa ccccgaaaa gggcggcgtg     1680 ttcatcgctg gccgggtcaa caagggggg attcttatta gatccgcgag ggggatcttt     1740
ttctggatct tcgccaacgg gacttaccgc gtgaccggag atctggccgg ctgggtgatc     1800
tacgccctgg gtagagtgga cgtgaccgcg aagaaatggt acactctgac cctgattatc     1860
aaagggcggt tgagctccgg catgctgaac gggaaaactg tctggaaaaa catcccagtg     1920
tcattcccta agaacggatg ggccgccatc ggaactcaca gctttgagtt cgcccagttt     1980
gataactttc atgtcgaagc gacccgc                                          2007
```

<210> SEQ ID NO 3
<211> LENGTH: 306
<212> TYPE: DNA
<213> ORGANISM: Artificial
<220> FEATURE:
<223> OTHER INFORMATION: Chicken beta-actin promoter

<400> SEQUENCE: 3

```
tacgtattag tcatcgctat taccatggtc gaggtgagcc ccacgttctg cttcactctc       60
cccatctccc cccccctcccc acccccaatt ttgtatttat ttatttttta attattttgt     120
```

| | | |
|---|---|---|
| gcagcgatgg gggcggggg ggggggggg cgcgcgccag gcgggcggg gcggggcgag | 180 |
| gggcggggcg gggcgaggcg gagaggtgcg gcggcagcca atcagagcgg cgcgctccga | 240 |
| aagtttcctt ttatggcgag gcggcggcgg cggcggccct ataaaaagcg aagcgcgcgg | 300 |
| cgggcg | 306 |

<210> SEQ ID NO 4
<211> LENGTH: 1881
<212> TYPE: DNA
<213> ORGANISM: Artificial
<220> FEATURE:
<223> OTHER INFORMATION: CAGGS promoter 1.6kb CMV enhancer, CBA promoter and partial 5' UTR

<400> SEQUENCE: 4

| | | |
|---|---|---|
| gatctgaatt cggatcttca atattggcca ttagccatat tattcattgg ttatatagca | 60 |
| taaatcaata ttggatattg gccattgcat acgttgtatc tatatcataa tatgtacatt | 120 |
| tatattggct catgtccaat atgaccgcca tgttggcatt gattattgac tagttattaa | 180 |
| tagtaatcaa ttacggggtc attagttcat agcccatata tggagttccg cgttacataa | 240 |
| cttacggtaa atggcccgcc tggctgaccg cccaacgacc cccgcccatt gacgtcaata | 300 |
| atgacgtatg ttcccatagt aacgccaata gggactttcc attgacgtca atgggtggag | 360 |
| tatttacggt aaactgccca cttggcagta catcaagtgt atcatatgcc aagtccgccc | 420 |
| cctattgacg tcaatgacgg taaatggccc gcctggcatt atgcccagta catgacctta | 480 |
| cgggactttc ctacttggca gtacatctac gtattagtca tcgctattac catggtcgag | 540 |
| gtgagcccca cgttctgctt cactctcccc atctccccc cctccccacc cccaattttg | 600 |
| tatttattta ttttttaatt attttgtgca gcgatgggg cggggggg ggggggcgc | 660 |
| gcgccaggcg gggcggggcg gggcgagggg cggggcgggg cgaggcggag aggtgcggcg | 720 |
| gcagccaatc agagcggcgc gctccgaaag tttcctttta tggcgaggcg gcggcggcgg | 780 |
| cggccctata aaagcgaag cgcgcggcgg gcgggagtcg ctgcgacgct gccttcgccc | 840 |
| cgtgccccgc tccgccgccg cctcgcgccg cccgccccgg ctctgactga ccgcgttact | 900 |
| cccacaggtg agcgggcggg acggcccttc tcctccgggc tgtaattagc gcttggttta | 960 |
| atgacggctt gtttcttttc tgtggctgcg tgaaagcctt gaggggctcc gggagggccc | 1020 |
| tttgtgcggg gggagcggc tcggggggtg cgtgcgtgtg tgtgtgcgtg gggagcgccg | 1080 |
| cgtgcggccc gcgctgcccg gcggctgtga gcgctgcggg cgcggcgcgg gctttgtgc | 1140 |
| gctccgcagt gtgcgcgagg ggagcgcggc cgggggcggt gccccgcggt gcggggggg | 1200 |
| ctgcgagggg aacaaaggct gcgtgcgggg tgtgtgcgtg ggggggtgag caggggggtat | 1260 |
| gggcgcggcg gtcgggctgt aaccccccc tgcacccccc tccccgagtt gctgagcacg | 1320 |
| gcccggcttc gggtgcgggg ctccgtacgg ggcgtggcgc ggggctcgcc gtgccgggcg | 1380 |
| gggggtggcg gcaggtgggg gtgccggggcg gggcggggcc gcctcgggcc gggagggct | 1440 |
| cgggggaggg gcgcggcggc ccccggagcg ccggcggctg tcgaggcgcg gcgagccgca | 1500 |
| gccattgcct tttatggtaa tcgtgcgaga gggcgcaggg acttactttg tcccaaatct | 1560 |
| gtgcggagcc gaaatctggg aggcgccgcc gcaccccctc tagcgggcgc ggggcgaagc | 1620 |
| ggtgcggcgc cggcaggaag gaaatgggcg ggagggcct tcgtgcgtcg ccgcgccgcc | 1680 |
| gtccccttct ccctctccag cctcggggct gtccgcgggg gacggctgc cttcgggggg | 1740 |
| gacggggcag ggcggggttc ggcttctggc gtgtgaccgg cggctctaga gcctctgcta | 1800 |

```
accatgttca tgccttcttc tttttcctac agctcctggg caacgtgctg gttattgtgc    1860
tgtctcatca ttttggcaaa g                                              1881

<210> SEQ ID NO 5
<211> LENGTH: 164
<212> TYPE: DNA
<213> ORGANISM: Artificial
<220> FEATURE:
<223> OTHER INFORMATION: JeT promoter

<400> SEQUENCE: 5
gggcggagtt agggcggagc caatcagcgt gcgccgttcc gaaagttgcc ttttatggct      60
gggcggagaa tgggcggtga acgccgatga ttatataagg acgcgccggg tgtggcacag    120
ctagttccgt cgcagccggg atttgggtcg cggttcttgt ttgt                     164

<210> SEQ ID NO 6
<211> LENGTH: 48
<212> TYPE: DNA
<213> ORGANISM: Artificial
<220> FEATURE:
<223> OTHER INFORMATION: Synthetic polyadenylation signal (SpA)

<400> SEQUENCE: 6
aataaagagc tcagatgcat cgatcagagt gtgttggttt tttgtgtg                  48

<210> SEQ ID NO 7
<211> LENGTH: 143
<212> TYPE: DNA
<213> ORGANISM: Artificial
<220> FEATURE:
<223> OTHER INFORMATION: SV40 polyadenylation signal (SV40pA)

<400> SEQUENCE: 7
agacatgata agatacattg atgagtttgg acaaaccaca actagaatgc agtgaaaaaa     60
atgctttatt tgtgaaattt gtgatgctat tgctttattt gtaaccatta taagctgcaa    120
taaacaagtt aacaacaaca att                                            143

<210> SEQ ID NO 8
<211> LENGTH: 4681
<212> TYPE: DNA
<213> ORGANISM: Artificial
<220> FEATURE:
<223> OTHER INFORMATION: Human GALC expression cassette with
      CAGGS/SV40polyA

<400> SEQUENCE: 8
gggggggggg ggggggggttg gccactccct ctctgcgcgc tcgctcgctc actgaggccg     60
ggcgaccaaa ggtcgcccga cgcccgggct tgcccgggc ggcctcagtg agcgagcgag    120
cgcgcagaga gggagtggcc aactccatca ctagggttc ctagatctga attcggatct    180
tcaatattgg ccattagcca tattattcat tggttatata gcataaatca atattggcta    240
ttggccattg catacgttgt atctatatca taatatgtac atttatattg gctcatgtcc    300
aatatgaccg ccatgttggc attgattatt gactagttat taatagtaat caattacggg    360
gtcattagtt catagcccat atatggagtt ccgcgttaca taacttacgg taaatggccc    420
gcctggctga ccgcccaacg accccgccc attgacgtca ataatgacgt atgttcccat    480
agtaacgcca atagggactt tccattgacg tcaatgggtg gagtatttac ggtaaactgc    540
ccacttggca gtacatcaag tgtatcatat gccaagtccg cccccctattg acgtcaatga    600
```

-continued

```
cggtaaatgg cccgcctggc attatgccca gtacatgacc ttacgggact ttcctacttg    660
gcagtacatc tacgtattag tcatcgctat taccatggtc gaggtgagcc ccacgttctg    720
cttcactctc cccatctccc cccctcccc accccaatt ttgtatttat ttatttttta    780
attattttgt gcagcgatgg gggcggggg gggggggggg cgcgcgccag gcggggcggg    840
gcggggcgag gggcggggcg gggcgaggcg gagaggtgcg gcggcagcca atcagagcgg    900
cgcgctccga aagtttcctt ttatggcgag gcggcggcgg cggcggccct ataaaaagcg    960
aagcgcgcgg cgggcgggag tcgctgcgac gctgccttcg ccccgtgccc cgctccgccg   1020
ccgcctcgcg ccgcccgccc cggctctgac tgaccgcgtt actcccacag gtgagcgggc   1080
gggacggccc ttctcctccg ggctgtaatt agcgcttggt ttaatgacgg cttgtttctt   1140
ttctgtggct gcgtgaaagc cttgaggggc tccgggaggg ccctttgtgc gggggggagc   1200
ggctcggggg gtgcgtgcgt gtgtgtgtgc gtggggagcg ccgcgtgcgg cccgcgctgc   1260
ccggcggctg tgagcgctgc gggcgcgcg cggggctttg tgcgctccgc agtgtgcgcg   1320
aggggagcgc ggccggggc ggtgccccgc ggtgcggggg gggctgcgag gggaacaaag   1380
gctgcgtgcg gggtgtgtgc gtggggggt gagcaggggg tatgggcgcg gcggtcgggc   1440
tgtaaccccc ccctgcaccc ccctccccga gttgctgagc acggcccggc ttcgggtgcg   1500
gggctccgta cggggcgtgg cgcggggctc gccgtgccgg gcggggggtg gcggcaggtg   1560
ggggtgccgg gcggggcggg gccgcctcgg gccggggagg gctcggggga ggggcgcggc   1620
ggcccccgga gcgccggcgg ctgtcgaggc gcggcgagcc gcagccattg cctttatgg   1680 taatcgtgcg agagggcgca gggacttcct ttgtcccaaa tctgtgcgga gccgaaatct   1740
gggaggcgcc gccgcacccc ctctagcggg cgcggggcga agcggtgcgg cgccggcagg   1800
aaggaaatgg gcgggaggg ccttcgtgcg tcgccgcgcc gccgtcccct tctccctctc   1860
cagcctcggg gctgtccgcg gggggacggc tgccttcggg gggacgggg cagggcgggg   1920 ttcggcttct ggcgtgtgac cggcggctct agagcctctg ctaaccatgt tcatgccttc   1980
ttctttttcc tacagctcct gggcaacgtg ctggttattg tgctgtctca tcattttggc   2040
aaagaattct agaggatccg gtactcgagg aactgaaaaa ccagaaagtt aactggtaag   2100
tttagtcttt ttgtcttta tttcaggtcc cggatccggt ggtggtgcaa atcaaagaac   2160
tgctcctcag tggatgttgc cttacttct aggcctgtac ggaagtgtta cttctgctct   2220
aaaagctgcg gaattgtacc cgcggcccgg gatccaccgg tgccaccatg gctgagtggc   2280
tccttagcgc gagctggcag cggagagcca aggcaatgac agcggcggcg ggctccgccg   2340
gacgcgctgc cgtccctctg ttgctctgtg cgttgctggc accgggtgga gcgtatgtgc   2400
ttgatgattc ggacggactc ggtagagaat ttgacggaat cggagcggtc agcggtggag   2460
gagcgacgag ccgcctgctc gtgaactatc ccgaacccta ccgatcccag attctggact   2520 acctttcaa acctaacttc ggcgcaagcc ttcacatcct caaggtggag atcggtgggg   2580
acggtcagac cacagacggt acggaaccat cgcacatgca ctatgcgctc gacgaaaact   2640
actttagagg gtatgagtgg tggctgatga aagaggccaa aaagcggaat ccgaatatca   2700
ctctcattgg tttgccgtgg agcttcccg gctggctggg gaaggggttc gactggccct   2760
atgtgaacct tcaactgaca gcgtattacg tggtcacatg gattgtcggg gcgaagaggt   2820
atcatgactt ggatatcgac tatattggta tctggaacga gagatcctac aacgcaaact   2880
acatcaaaat ccttagaaag atgttgaatt atcagggct gcagagagtc aaaatcatcg   2940
```

-continued

```
catccgacaa tctttgggaa tcgatctcag cgtcaatgct cctcgacgcg gaactgttta    3000
aagtggtgga tgtcattggg gcgcattacc cgggaacaca ctcggcgaaa gacgcaaagt    3060
tgacggggaa gaaattgtgg tcgagcgagg attttttccac tcttaattcg gatatggggg   3120
cagggtgttg gggaagaatt ctgaaccaga actatatcaa cgggtatatg acctcgacga    3180
tcgcctggaa tcttgtggca tcctactacg agcagctgcc ttacgggagg tgcggtctta    3240
tgacagcgca ggagccctgg tcgggacatt acgtcgtcga gagccccgta tgggtatcag    3300
cccacacgac ccagtttaca cagccgggct ggtattacct taagacggtg gccatcttg     3360 agaagggagg tagctatgtc gcgctgacgg atggcttggg taatttgaca atcatcattg    3420
aaactatgtc gcataaacac tcaaagtgca ttcgcccttt tctgccctat ttcaacgtca    3480
gccagcaatt tgcgacgttt gtgcttaagg gatcgttttc ggagattccc gaacttcagg    3540
tctggtacac gaaacttgga aagacgtcag aaaggttcct tttcaagcag ttggactcgc    3600
tctggctttt ggatagcgac ggatcgttca ctctgtcctt gcacgaggat gagttgttca    3660
cgctcactac cctcaccact ggcagaaagg gctcctaccc gttgccccg aaaagccagc     3720 cgtttccttc aacttataag gatgacttta atgtcgatta cccattcttc tcggaggccc    3780
cgaattttgc cgaccaaaca ggagtatttg aatacttcac gaacatcgag gacccggggg   3840
agcaccattt cactctgaga caagtgttga accaaaggcc gattacttgg gcagccgatg    3900
ccagcaatac catttcgatt atcggagact ataactggaa aaacttgacc atcaaatgcg    3960
atgtctatat cgaaacgcct gatacagggg gtgtgttcat cgctggtcgc gtaaacaaag    4020 ggggaattt gatccgctca gctagaggga tcttcttttg gattttcgcg aacggaagct     4080
accgcgtgac gggagacttg gcgggatgga tcatctacgc cctgggtcgc gtggaggtaa    4140
cagcgaaaaa gtggtacacg ttgaccttga caattaaggg gcacttcacg tccgggatgc    4200
tgaacgacaa gagcctctgg acggacatcc ccgtgaattt ccccaaaaac gggtgggcag    4260
caattgggac gcactccttt gaatttgcgc aattcgacaa cttttttggta gaggctacgc   4320 ggtgatagcc tagggatggc cgcgcggatc cagacatgat aagatacatt gatgagtttg    4380
gacaaaccac aactagaatg cagtgaaaaa aatgctttat ttgtgaaatt tgtgatgcta    4440
ttgctttatt tgtaaccatt ataagctgca ataaacaagt taacaacaac aatttagcag    4500
gcatgctggg gagagatcta ggaaccccta gtgatggagt tggccactcc ctctctgcgc    4560
gctcgctcgc tcactgaggc cgcccgggca aagcccgggc gtcgggcgac ctttggtcgc    4620
ccggcctcag tgagcgagcg agcgcgcaga gagggagtgg ccaaccccc ccccccccc      4680 c                                                                   4681
```

<210> SEQ ID NO 9
<211> LENGTH: 4634
<212> TYPE: DNA
<213> ORGANISM: Artificial
<220> FEATURE:
<223> OTHER INFORMATION: Canine GALC expression cassette with
      CAGGS/SV40polyA

<400> SEQUENCE: 9

```
gggggggggg ggggggggttg ccactccct ctctgcgcgc tcgctcgctc actgaggccg     60
ggcgaccaaa ggtcgcccga cgcccgggct tgcccgggc ggcctcagtg agcgagcgag      120
cgcgcagaga gggagtggcc aactccatca ctaggggttc ctagatctga attcggatct    180
tcaatattgg ccattagcca tattattcat tggttatata gcataaatca atattggata    240
```

-continued

```
ttggccattg catacgttgt atctatatca taatatgtac atttatattg gctcatgtcc    300
aatatgaccg ccatgttggc attgattatt gactagttat taatagtaat caattacggg    360
gtcattagtt catagcccat atatggagtt ccgcgttaca taacttacgg taaatggccc    420
gcctggctga ccgcccaacg accccgcccc attgacgtca ataatgacgt atgttcccat    480
agtaacgcca atagggactt tccattgacg tcaatgggtg gagtatttac ggtaaactgc    540
ccacttggca gtacatcaag tgtatcatat gccaagtccg cccctattg acgtcaatga    600 cggtaaatgg cccgcctggc attatgccca gtacatgacc ttacgggact ttcctacttg    660
gcagtacatc tacgtattag tcatcgctat taccatggtc gaggtgagcc ccacgttctg    720
cttcactctc cccatctccc cccctcccc accccaatt ttgtatttat ttatttttta    780
attattttgt gcagcgatgg gggcgggggg gggggggggg cgcgcgccag gcggggcggg    840
gcggggcgag gggcggggcg gggcgaggcg gagaggtgcg cggcagcca atcagagcgg    900 cgcgctccga aagtttcctt ttatggcgag gcggcggcgg cggcggccct ataaaaagcg    960
aagcgcgcgc cgggcgggag tcgctgcgac gctgccttcg ccccgtgccc cgctccgccg   1020
ccgcctcgcg ccgcccgccc cggctctgac tgaccgcgtt actcccacag gtgagcgggc   1080
gggacggccc ttctcctccg ggctgtaatt agcgcttggt ttaatgacgg cttgtttctt   1140
ttctgtggct gcgtgaaagc cttgaggggc tccgggaggg cccttttgtgc ggggggagc   1200 ggctcggggg gtgcgtgcgt gtgtgtgtgc gtggggagcg ccgcgtgcgg cccgcgctgc   1260
ccggcggctg tgagcgctgc gggcgcggcg cggggctttg tgcgctccgc agtgtgcgcg   1320
aggggagcgc ggccgggggc ggtgccccgc ggtgcggggg gggctgcgag gggaacaaag   1380
gctgcgtgcg gggtgtgtgc gtggggggggt gagcaggggg tatgggcgcg gcggtcgggc   1440
tgtaaccccc ccctgcaccc ccctccccga gttgctgagc acggcccggc ttcgggtgcg   1500
gggctccgta cggggcgtgg cgcggggctc gccgtgccgg gcggggggtg gcggcaggtg   1560
ggggtgccgg gcggggcggg gccgcctcgg gccggggagg gctcggggga ggggcgcggc   1620
ggcccccgga gcgccggcgg ctgtcgaggc gcggcgagcc gcagccattg ccttttatgg   1680
taatcgtgcg agagggcgca gggacttact ttgtcccaaa tctgtgcgga gccgaaatct   1740
gggaggcgcc gccgcacccc ctctagcggg cgcggggcga agcggtgcgg cgccggcagg   1800
aaggaaatgg gcggggaggg ccttcgtgcg tcgccgcgcc gccgtcccct tctccctctc   1860
cagcctcggg gctgtccgcg gggggacggc tgccttcggg ggggacgggg cagggcgggg   1920
ttcggcttct ggcgtgtgac cggcggctct agagcctctg ctaaccatgt tcatgccttc   1980 ttcttttttcc tacagctcct gggcaacgtg ctggttattg tgctgtctca tcattttggc   2040
aaagaattct agaggatccg gtactcgagg aactgaaaaa ccagaaagtt aactggtaag   2100 tttagtctttt ttgtctttta tttcaggtcc cggatccggt ggtggtgcaa atcaaagaac   2160
tgctcctcag tggatgttgc ctttacttct aggcctgtac ggaagtgtta cttctgctct   2220
aaaagctgcg gaattgtacc cgcggcccgg gatccaaccg gtgccaccat gaccgcagcc   2280
gcaggatctg caggccatgc tgcggtgccc ctgttgttgt gtgcccttct ggtccctggc   2340
ggagcttacg tgctggacga ctccgacggt ttgggccggg agttcgacgg agtgggagct   2400
gtctccggtg gtgagcgac cagcagactc ctcgtgaact accggagcc gtacaggtca   2460 cagatcctcg actacctgtt caagccaaat ttcggtgcct cccttcatat cctgaaagtg   2520
gaaatcggtg gagatggaca gactaccgac ggaacggagc cctcccacat gcattacgcc   2580
ctggacgaaa atttcttccg gggctacgag tggtggctga tgaaggaggc caagaagcgg   2640
```

```
aacccgaaca tcatcctgat gggactccct tggtccttcc ccggctggat cggaaaggga    2700
ttcaactggc cctacgtgaa cctccagctt accgcctact acatcatgac ttggattgtg    2760
ggcgccaagc attaccacga cctggacatc gactacatcg gcatttggaa cgagcggtcc    2820
tttgacatca actacattaa ggtgctgagg aggatgctga attatcaggg actcgacaga    2880
gtgaagatta ttgcctcgga caacctgtgg gagccgatct cggcgtccat gctgcttgat    2940
agcgagctcc tcaaggtcat cgacgtgatc ggagcccact accctggtac acacaccgtg    3000
aaggacgcga agctgaccaa gaagaagctg tggtcctccg aggacttctc caccctgaac    3060
agcgatgtcg gagccggatg cttgggacgg atcctgaacc agaactacgt gaacggctac    3120
atgaccgcca ccattgcctg gaacctggtg gcgtcttact atgagcaact cccttacgga    3180
cgctgtgggc tgatgactgc ccaggaacca tggagcggcc actacgtggt ggagtcccct    3240
atctgggtca gcgcccacac cacccagttt acccagccgg gatggtacta cctcaagacc    3300
gtggggcacc ttgagaaggg aggatcctac gtcgctctca ctgacgggct cggcaacttg    3360
actatcatag tggaaactat gtcccacaag cagtccgcat gcattcggcc cttcttgccg    3420
tacttcaacg tgtcacgcca gttcgccact ttcgtgctga agggttcgtt cagcgagatc    3480
ccggagctcc aagtctggta cactaagctg ggaaagcctt cagaacgcta cctcttcaag    3540
cagctggact ccctgtggct gctggattca tcatcgacct tcaccctgga actgcaggaa    3600
gatgaaatct tcaccctgac cactctgact gtgggcagca agggctcgta tccgctcccg    3660
ccgaagtcgg agccctttcc ccaaatctac gaagatgact tcgacgtgga ctatcccttc    3720
ttctcggaag ccccaaactt cgctgatcaa accggagtgt ttgagtattt caccaacatt    3780
gaggaccccg gagaacacag attcacgctg cgccaagtgc tcaaccagcg ccccatcacc    3840
tgggccgctg atgcctacaa caccatttcc atcattgggg actacaaatg gtcgaacctg    3900
accgtgcgct cgacgtgta catcgaaacc cccgaaaagg gcggcgtgtt catcgctggc    3960
cgggtcaaca aggggggat tcttattaga tccgcgaggg ggatcttttt ctggatcttc    4020
gccaacggga cttaccgcgt gaccggagat ctggccggct gggtgatcta cgccctgggt    4080
agagtggacg tgaccgcgaa gaaatggtac actctgaccc tgattatcaa agggcggttg    4140
agctccggca tgctgaacgg gaaaactgtc tggaaaaaca tcccagtgtc attccctaag    4200
aacggatggg ccgccatcgg aactcacagc tttgagttcg cccagtttga taactttcat    4260
gtcgaagcga cccgctaatg acctagggat ggccgcgggg atccagacat gataagatac    4320
attgatgagt ttggacaaac cacaactaga atgcagtgaa aaaatgctt tatttgtgaa    4380
atttgtgatg ctattgcttt atttgtaacc attataagct gcaataaaca agttaacaac    4440
aacaatttag caggcatgct ggggagagat ctaggaaccc ctagtgatgg agttggccac    4500
tccctctctg cgcgctcgct cgctcactga ggccgcccgg gcaaagcccg ggcgtcgggc    4560
gacctttggt cgcccggcct cagtgagcga gcgagcgcgc agagagggag tggccaaccc    4620
cccccccccc cccc                                                    4634
```

<210> SEQ ID NO 10
<211> LENGTH: 2287
<212> TYPE: DNA
<213> ORGANISM: Artificial
<220> FEATURE:
<223> OTHER INFORMATION: Human GALC expression cassette with JeT/spA

<400> SEQUENCE: 10

```
gggcggagtt agggcggagc caatcagcgt gcgccgttcc gaaagttgcc ttttatggct    60
gggcggagaa tgggcggtga acgccgatga ttatataagg acgcgccggg tgtggcacag   120
ctagttccgt cgcagccggg atttgggtcg cggttcttgt ttgttccgga aagccaccat   180
ggctgagtgg ctccttagcg cgagctggca gcggagagcc aaggcaatga cagcggcggc   240
gggctccgcc ggacgcgctg ccgtccctct gttgctctgt gcgttgctgg caccgggtgg   300
agcgtatgtg cttgatgatt cggacggact cggtagagaa tttgacggaa tcggagcggt   360
cagcggtgga ggagcgacga gccgcctgct cgtgaactat cccgaaccct accgatccca   420
gattctggac tacctttttca aacctaactt cggcgcaagc cttcacatcc tcaaggtgga   480
gatcggtggg gacggtcaga ccacagacgg tacggaacca tcgcacatgc actatgcgct   540
cgacgaaaac tactttagag ggtatgagtg gtggctgatg aaagaggcca aaaagcggaa   600
tccgaatatc actctcattg gtttgccgtg gagcttcccc ggctggctgg ggaaggggtt   660
cgactggccc tatgtgaacc ttcaactgac agcgtattac gtggtcacat ggattgtcgg   720
ggcgaagagg tatcatgact tggatatcga ctatattggt atctggaacg agagatccta   780
caacgcaaac tacatcaaaa tccttagaaa gatgttgaat tatcaggggc tgcagagagt   840
caaaatcatc gcatccgaca atctttggga atcgatctca gcgtcaatgc tcctcgacgc   900
ggaactgttt aaagtggtgg atgtcattgg ggcgcattac ccgggaacac actcggcgaa   960
agacgcaaag ttgacgggga agaaattgtg gtcgagcgag gattttttcca ctcttaattc  1020
ggatatgggg gcagggtgtt ggggaagaat tctgaaccag aactatatca acgggtatat  1080
gacctcgacg atcgcctgga atcttgtggc atcctactac gagcagctgc cttacgggag  1140
gtgcggtctt atgacagcgc aggagccctg gtcgggacat tacgtcgtcg agagcccgt  1200
atgggtatca gcccacacga cccagtttac acagccgggc tggtattacc ttaagacggt  1260
gggccatctt gagaagggag gtagctatgt cgcgctgacg gatggcttgg gtaatttgac  1320
aatcatcatt gaaactatgt cgcataaaca ctcaaagtgc attcgccctt ttctgcccta  1380
tttcaacgtc agccagcaat ttgcgacgtt tgtgcttaag ggatcgtttt cggagattcc  1440
cgaacttcag gtctggtaca cgaaacttgg aaagacgtca gaaaggttcc ttttcaagca  1500
gttggactcg ctctggcttt tggatagcga cggatcgttc actctgtcct tgcacgagga  1560
tgagttgttc acgctcacta ccctcaccac tggcagaaag gctcctacc cgttgccccc   1620
gaaaagccag ccgtttcctt caacttataa ggatgacttt aatgtcgatt acccattctt   1680
ctcggaggcc ccgaattttg ccgaccaaac aggagtattt gaatacttca cgaacatcga   1740
ggacccgggg gagcaccatt tcactctgag acaagtgttg aaccaaaggc cgattacttg   1800
ggcagccgat gccagcaata ccatttcgat tatcggagac tataactgga caaacttgac   1860
catcaaatgc gatgtctata tcgaaacgcc tgatacaggg ggtgtgttca tcgctggtcg   1920
cgtaaacaaa gggggaattt tgatccgctc agctagaggg atcttctttt ggattttcgc   1980
gaacggaagc taccgcgtga cgggagactt ggcgggatga tcatctacg ccctgggtcg   2040
cgtggaggta acagcgaaaa agtggtacac gttgaccttg acaattaagg ggcacttcac   2100
gtccgggatg ctgaacgaca agagcctctg gacggacatc cccgtgaatt tccccaaaaa   2160
cgggtgggca gcaattggga cgcactcctt tgaatttgcg caattcgaca acttttttggt   2220
agaggctacg cggaggccta ataaagagct cagatgcatc gatcagagtg tgttggtttt   2280
ttgtgtg                                                              2287
```

<210> SEQ ID NO 11
<211> LENGTH: 2239
<212> TYPE: DNA
<213> ORGANISM: Artificial
<220> FEATURE:
<223> OTHER INFORMATION: Canine GALC expression cassette with JeT/spA

<400> SEQUENCE: 11

| | | | | | |
|---|---|---|---|---|---|
| gggcggagtt | agggcggagc | caatcagcgt | gcgccgttcc | gaaagttgcc | ttttatggct | 60 |
| gggcggagaa | tgggcggtga | acgccgatga | ttatataagg | acgcgccggg | tgtggcacag | 120 |
| ctagttccgt | cgcagccggg | atttgggtcg | cggttcttgt | tgttccgga | aagccaccat | 180 |
| gaccgcagcc | gcaggatctg | caggccatgc | tgcgtgccc | ctgttgttgt | gtgcccttct | 240 |
| ggtccctggc | ggagcttacg | tgctggacga | ctccgacggt | ttgggccggg | agttcgacgg | 300 |
| agtgggagct | gtctccggtg | gtggagcgac | cagcagactc | ctcgtgaact | acccggagcc | 360 |
| gtacaggtca | cagatcctcg | actacctgtt | caagccaaat | ttcggtgcct | cccttcatat | 420 |
| cctgaaagtg | gaaatcggtg | gagatggaca | gactaccgac | ggaacggagc | cctcccacat | 480 |
| gcattacgcc | ctggacgaaa | atttcttccg | gggctacgag | tggtggctga | tgaaggaggc | 540 |
| caagaagcgg | aacccgaaca | tcatcctgat | gggactccct | tggtccttcc | ccggctggat | 600 |
| cggaaaggga | ttcaactggc | cctacgtgaa | cctccagctt | accgcctact | acatcatgac | 660 |
| ttggattgtg | ggcgccaagc | attaccacga | cctggacatc | gactacatcg | gcatttggaa | 720 |
| cgagcggtcc | tttgacatca | actacattaa | ggtgctgagg | aggatgctga | attatcaggg | 780 |
| actcgacaga | gtgaagatta | ttgcctcgga | caacctgtgg | gagccgatct | cggcgtccat | 840 |
| gctgcttgat | agcgagctcc | tcaaggtcat | cgacgtgatc | ggagcccact | accctggtac | 900 |
| acacaccgtg | aaggacgcga | agctgaccaa | gaagaagctg | tggtcctccg | aggacttctc | 960 |
| caccctgaac | agcgatgtcg | agccggatg | cttgggacgg | atcctgaacc | agaactacgt | 1020 |
| gaacggctac | atgaccgcca | ccattgcctg | gaacctggtg | gcgtcttact | atgagcaact | 1080 |
| cccttacgga | cgctgtgggc | tgatgactgc | ccaggaacca | tggagcggcc | actacgtggt | 1140 |
| ggagtcccct | atctgggtca | gcgcccacac | cacccagttt | acccagccgg | atggtacta | 1200 |
| cctcaagacc | gtggggcacc | ttgagaaggg | aggatcctac | gtcgctctca | ctgacgggct | 1260 |
| cggcaacttg | actatcatag | tggaaactat | gtcccacaag | cagtccgcat | gcattcggcc | 1320 |
| cttcttgccg | tacttcaacg | tgtcacgcca | gttcgccact | ttcgtgctga | gggttcgtt | 1380 |
| cagcgagatc | ccggagctcc | aagtctggta | cactaagctg | ggaaagcctt | cagaacgcta | 1440 |
| cctcttcaag | cagctggact | ccctgtggct | gctggattca | tcatcgacct | tcaccctgga | 1500 |
| actgcaggaa | gatgaaatct | tcaccctgac | cactctgact | gtgggcagca | agggctcgta | 1560 |
| tccgctcccg | ccgaagtcgg | agcccttccc | ccaaatctac | gaagatgact | cgacgtgga | 1620 |
| ctatcccttc | ttctcggaag | ccccaaactt | cgctgatcaa | accggagtgt | tgagtattt | 1680 |
| caccaacatt | gaggaccccg | gagaacacag | attcacgctg | cgccaagtgc | tcaaccagcg | 1740 |
| ccccatcacc | tgggccgctg | atgcctacaa | caccattcc | atcattgggg | actacaaatg | 1800 |
| gtcgaacctg | accgtgcgct | gcgacgtgta | catcgaaacc | cccgaaaagg | gcggcgtgtt | 1860 |
| catcgctggc | cgggtcaaca | aggggggat | tcttattaga | tccgcgaggg | ggatcttttt | 1920 |
| ctggatcttc | gccaacggga | cttaccgcgt | gaccggagat | ctggccggct | gggtgatcta | 1980 |
| cgccctgggt | agagtggacg | tgaccgcgaa | gaaatggtac | actctgaccc | tgattatcaa | 2040 |
| agggcggttg | agctccggca | tgctgaacgg | gaaaactgtc | tggaaaaaca | tcccagtgtc | 2100 |

```
attccctaag aacggatggg ccgccatcgg aactcacagc tttgagttcg cccagtttga   2160
taactttcat gtcgaagcga cccgcaggcc taataaagag ctcagatgca tcgatcagag   2220
tgtgttggtt ttttgtgtg                                                2239
```

<210> SEQ ID NO 12
<211> LENGTH: 642
<212> TYPE: PRT
<213> ORGANISM: Rattus norvegicus

<400> SEQUENCE: 12

```
Tyr Glu Leu Asp Asp Ser Asp Gly Leu Gly Leu Glu Phe Asp Gly Ile
1               5                   10                  15

Gly Ala Val Ser Gly Gly Ala Thr Ser Arg Leu Leu Val Asn Tyr
                20                  25                  30

Pro Glu Pro Tyr Arg Ser Glu Ile Leu Asp Tyr Leu Phe Lys Pro Asn
            35                  40                  45

Phe Gly Ala Ser Leu His Ile Leu Lys Val Glu Ile Gly Gly Asp Gly
        50                  55                  60

Gln Thr Thr Asp Gly Thr Glu Pro Ser His Met His Tyr Glu Leu Asp
65                  70                  75                  80

Glu Asn Tyr Phe Arg Gly Tyr Glu Trp Trp Leu Met Lys Glu Ala Lys
                85                  90                  95

Lys Arg Asn Pro Asn Ile Ile Leu Met Gly Leu Pro Trp Ser Phe Pro
            100                 105                 110

Gly Trp Leu Gly Lys Gly Phe Ser Trp Pro Tyr Val Asn Leu Gln Leu
        115                 120                 125

Thr Ala Phe Tyr Ile Val Arg Trp Ile Leu Gly Ala Lys His Tyr His
    130                 135                 140

Asp Leu Asp Ile Asp Tyr Ile Gly Ile Trp Asn Glu Arg Pro Phe Asp
145                 150                 155                 160

Ala Asn Tyr Ile Lys Glu Leu Arg Lys Met Leu Asp Tyr Glu Gly Leu
                165                 170                 175

Gln Arg Val Arg Ile Ile Ala Ser Asp Asn Leu Trp Glu Pro Ile Ser
            180                 185                 190

Ser Ser Val Leu Leu Asp Gln Glu Leu Trp Lys Val Asp Val Ile
        195                 200                 205

Gly Ala His Tyr Pro Gly Thr Tyr Thr Val Trp Asn Ala Lys Met Ser
    210                 215                 220

Gly Lys Lys Leu Trp Ser Ser Glu Asp Phe Ser Thr Val Asn Ser Asn
225                 230                 235                 240

Val Gly Ala Gly Cys Trp Gly Arg Ile Leu Asn Gln Asn Tyr Ile Asn
                245                 250                 255

Gly Asn Met Thr Ala Thr Ile Ala Trp Asn Leu Val Ala Ser Tyr Tyr
            260                 265                 270

Glu Glu Leu Pro Tyr Gly Arg Ser Gly Leu Met Thr Ala Gln Glu Pro
        275                 280                 285

Trp Ser Gly His Tyr Val Val Ala Ser Pro Ile Trp Val Ser Ala His
    290                 295                 300

Thr Thr Gln Phe Thr Gln Pro Gly Trp Tyr Tyr Leu Lys Thr Val Gly
305                 310                 315                 320

His Leu Glu Lys Gly Gly Ser Tyr Val Ala Leu Thr Asp Gly Leu Gly
                325                 330                 335

Asn Phe Thr Ile Ile Val Glu Thr Met Ser Arg Gln His Ser Met Cys
            340                 345                 350
```

-continued

Ile Arg Pro Tyr Leu Pro Tyr Tyr Asn Val Ser Arg Gln Leu Ala Thr
            355                 360                 365

Phe Ile Leu Lys Gly Ser Leu Lys Glu Ile Gln Glu Leu Gln Val Trp
370                 375                 380

Tyr Thr Lys Leu Gly Thr Thr Pro Glu Lys Leu His Phe Lys Gln Leu
385                 390                 395                 400

Glu Thr Leu Trp Leu Leu Asp Gly Ser Gly Ser Phe Ser Leu Glu Leu
                405                 410                 415

Glu Glu Asp Glu Met Phe Thr Leu Thr Thr Leu Thr Thr Gly His Lys
            420                 425                 430

Gly Ser Tyr Arg Pro Pro Lys Ser Gln Pro Phe Pro Thr Ser Tyr
        435                 440                 445

Lys Asp Asp Phe Asn Val Glu Tyr Pro Leu Phe Ser Glu Ala Pro Asn
    450                 455                 460

Phe Ala Asp Gln Thr Gly Val Phe Glu Tyr Tyr Thr Asn Asn Glu Asp
465                 470                 475                 480

Leu Glu His Arg Phe Thr Leu Arg Gln Val Leu Asn Gln Arg Pro Ile
                485                 490                 495

Thr Trp Ala Ala Asp Ala Ser Ser Thr Ile Ser Val Ile Gly Asp His
            500                 505                 510

His Trp Ser Asn Met Thr Val Gln Cys Asp Val Tyr Ile Glu Thr Pro
        515                 520                 525

Arg Thr Gly Gly Val Phe Ile Ala Gly Arg Val Asn Lys Gly Gly Ile
    530                 535                 540

Leu Ile Arg Thr Ala Ser Gly Val Phe Phe Trp Ile Phe Ala Asn Gly
545                 550                 555                 560

Ser Tyr Arg Val Thr Ala Asp Leu Gly Gly Trp Ile Thr Tyr Ala Ser
                565                 570                 575

Gly His Ala Asp Val Thr Ala Lys Arg Trp Tyr Thr Leu Thr Leu Gly
            580                 585                 590

Ile Lys Gly Tyr Leu Ala Ser Gly Met Leu Asn Gly Lys Ile Leu Trp
        595                 600                 605

Glu Asn Val Pro Val Lys Tyr Pro Gly His Gly Trp Ala Ala Ile Gly
    610                 615                 620

Thr His Thr Phe Glu Phe Ala Gln Phe Asp Asn Phe His Val Glu Ala
625                 630                 635                 640

Ala Arg

<210> SEQ ID NO 13
<211> LENGTH: 642
<212> TYPE: PRT
<213> ORGANISM: Mus musculus

<400> SEQUENCE: 13

Tyr Val Leu Asp Asp Ser Asp Gly Leu Gly Arg Glu Phe Asp Gly Ile
1               5                   10                  15

Gly Ala Val Ser Gly Gly Gly Ala Thr Ser Arg Leu Leu Val Asn Tyr
            20                  25                  30

Pro Glu Pro Tyr Arg Ser Glu Ile Leu Asp Tyr Leu Phe Lys Pro Asn
        35                  40                  45

Phe Gly Ala Ser Leu His Ile Leu Lys Val Glu Ile Gly Gly Asp Gly
    50                  55                  60

Gln Thr Thr Asp Gly Thr Glu Pro Ser His Met His Tyr Glu Leu Asp
65                  70                  75                  80

```
Glu Asn Tyr Phe Arg Gly Tyr Glu Trp Trp Leu Met Lys Glu Ala Lys
                85                  90                  95
Lys Arg Asn Pro Asp Ile Ile Leu Met Gly Leu Pro Trp Ser Phe Pro
                100                 105                 110
Gly Trp Leu Gly Lys Gly Phe Ser Trp Pro Tyr Val Asn Leu Gln Leu
                115                 120                 125
Thr Ala Tyr Tyr Val Val Arg Trp Ile Leu Gly Ala Lys His Tyr His
                130                 135                 140
Asp Leu Asp Ile Asp Tyr Ile Gly Ile Trp Asn Glu Arg Pro Phe Asp
145                 150                 155                 160
Ala Asn Tyr Ile Lys Glu Leu Arg Lys Met Leu Asp Tyr Gln Gly Leu
                165                 170                 175
Gln Arg Val Arg Ile Ile Ala Ser Asp Asn Leu Trp Glu Pro Ile Ser
                180                 185                 190
Ser Ser Leu Leu Leu Asp Gln Glu Leu Trp Lys Val Val Asp Val Ile
                195                 200                 205
Gly Ala His Tyr Pro Gly Thr Tyr Thr Val Trp Asn Ala Lys Met Ser
                210                 215                 220
Gly Lys Lys Leu Trp Ser Ser Glu Asp Phe Ser Thr Ile Asn Ser Asn
225                 230                 235                 240
Val Gly Ala Gly Cys Trp Ser Arg Ile Leu Asn Gln Asn Tyr Ile Asn
                245                 250                 255
Gly Asn Met Thr Ser Thr Ile Ala Trp Asn Leu Val Ala Ser Tyr Tyr
                260                 265                 270
Glu Glu Leu Pro Tyr Gly Arg Ser Gly Leu Met Thr Ala Gln Glu Pro
                275                 280                 285
Trp Ser Gly His Tyr Val Val Ala Ser Pro Ile Trp Val Ser Ala His
                290                 295                 300
Thr Thr Gln Phe Thr Gln Pro Gly Trp Tyr Tyr Leu Lys Thr Val Gly
305                 310                 315                 320
His Leu Glu Lys Gly Gly Ser Tyr Val Ala Leu Thr Asp Gly Leu Gly
                325                 330                 335
Asn Leu Thr Ile Ile Ile Glu Thr Met Ser His Gln His Ser Met Cys
                340                 345                 350
Ile Arg Pro Tyr Leu Pro Tyr Tyr Asn Val Ser His Gln Leu Ala Thr
                355                 360                 365
Phe Thr Leu Lys Gly Ser Leu Arg Glu Ile Gln Glu Leu Gln Val Trp
                370                 375                 380
Tyr Thr Lys Leu Gly Thr Pro Gln Gln Arg Leu His Phe Lys Gln Leu
385                 390                 395                 400
Asp Thr Leu Trp Leu Leu Asp Gly Ser Gly Ser Phe Thr Leu Glu Leu
                405                 410                 415
Glu Glu Asp Glu Ile Phe Thr Leu Thr Thr Leu Thr Thr Gly Arg Lys
                420                 425                 430
Gly Ser Tyr Pro Pro Pro Ser Lys Pro Phe Pro Thr Asn Tyr
                435                 440                 445
Lys Asp Asp Phe Asn Val Glu Tyr Pro Leu Phe Ser Glu Ala Pro Asn
450                 455                 460
Phe Ala Asp Gln Thr Gly Val Phe Glu Tyr Tyr Met Asn Asn Glu Asp
465                 470                 475                 480
Arg Glu His Arg Phe Thr Leu Arg Gln Val Leu Asn Gln Arg Pro Ile
                485                 490                 495
```

```
Thr Trp Ala Ala Asp Ala Ser Ser Thr Ile Ser Val Ile Gly Asp His
            500                 505                 510

His Trp Thr Asn Met Thr Val Gln Cys Asp Val Tyr Ile Glu Thr Pro
        515                 520                 525

Arg Ser Gly Gly Val Phe Ile Ala Gly Arg Val Asn Lys Gly Ile
    530                 535                 540

Leu Ile Arg Ser Ala Thr Gly Val Phe Phe Trp Ile Phe Ala Asn Gly
545                 550                 555                 560

Ser Tyr Arg Val Thr Ala Asp Leu Gly Gly Trp Ile Thr Tyr Ala Ser
                565                 570                 575

Gly His Ala Asp Val Thr Ala Lys Arg Trp Tyr Thr Leu Thr Leu Gly
                580                 585                 590

Ile Lys Gly Tyr Phe Ala Phe Gly Met Leu Asn Gly Thr Ile Leu Trp
            595                 600                 605

Lys Asn Val Arg Val Lys Tyr Pro Gly His Gly Trp Ala Ala Ile Gly
610                 615                 620

Thr His Thr Phe Glu Phe Ala Gln Phe Asp Asn Phe Arg Val Glu Ala
625                 630                 635                 640

Ala Arg

<210> SEQ ID NO 14
<211> LENGTH: 643
<212> TYPE: PRT
<213> ORGANISM: Canis familiaris

<400> SEQUENCE: 14

Tyr Val Leu Asp Asp Ser Asp Gly Leu Gly Arg Glu Phe Asp Gly Val
1               5                   10                  15

Gly Ala Val Ser Gly Gly Gly Ala Thr Ser Arg Leu Leu Val Asn Tyr
            20                  25                  30

Pro Glu Pro Tyr Arg Ser Gln Ile Leu Asp Tyr Leu Phe Lys Pro Asn
        35                  40                  45

Phe Gly Ala Ser Leu His Ile Leu Lys Val Glu Ile Gly Gly Asp Gly
    50                  55                  60

Gln Thr Thr Asp Gly Thr Glu Pro Ser His Met His Tyr Ala Leu Asp
65                  70                  75                  80

Glu Asn Phe Phe Arg Gly Tyr Glu Trp Trp Leu Met Lys Glu Ala Lys
                85                  90                  95

Lys Arg Asn Pro Asn Ile Ile Leu Met Gly Leu Pro Trp Ser Phe Pro
            100                 105                 110

Gly Trp Ile Gly Lys Gly Phe Asn Trp Pro Tyr Val Asn Leu Gln Leu
        115                 120                 125

Thr Ala Tyr Tyr Ile Met Thr Trp Ile Val Gly Ala Lys His Tyr His
    130                 135                 140

Asp Leu Asp Ile Asp Tyr Ile Gly Ile Trp Asn Glu Arg Ser Phe Asp
145                 150                 155                 160

Ile Asn Tyr Ile Lys Val Leu Arg Arg Met Leu Asn Tyr Gln Gly Leu
                165                 170                 175

Asp Arg Val Lys Ile Ile Ala Ser Asp Asn Leu Trp Glu Pro Ile Ser
            180                 185                 190

Ala Ser Met Leu Leu Asp Ser Glu Leu Leu Lys Val Ile Asp Val Ile
        195                 200                 205

Gly Ala His Tyr Pro Gly Thr His Thr Val Lys Asp Ala Lys Leu Thr
    210                 215                 220
```

```
Lys Lys Lys Leu Trp Ser Ser Glu Asp Phe Ser Thr Leu Asn Ser Asp
225                 230                 235                 240

Val Gly Ala Gly Cys Leu Gly Arg Ile Leu Asn Gln Asn Tyr Val Asn
            245                 250                 255

Gly Tyr Met Thr Ala Thr Ile Ala Trp Asn Leu Val Ala Ser Tyr Tyr
                260                 265                 270

Glu Gln Leu Pro Tyr Gly Arg Cys Gly Leu Met Thr Ala Gln Glu Pro
        275                 280                 285

Trp Ser Gly His Tyr Val Val Glu Ser Pro Ile Trp Val Ser Ala His
    290                 295                 300

Thr Thr Gln Phe Thr Gln Pro Gly Trp Tyr Tyr Leu Lys Thr Val Gly
305                 310                 315                 320

His Leu Glu Lys Gly Gly Ser Tyr Val Ala Leu Thr Asp Gly Leu Gly
                325                 330                 335

Asn Leu Thr Ile Ile Val Glu Thr Met Ser His Lys Gln Ser Ala Cys
                340                 345                 350

Ile Arg Pro Phe Leu Pro Tyr Phe Asn Val Ser Arg Gln Phe Ala Thr
        355                 360                 365

Phe Val Leu Lys Gly Ser Phe Ser Glu Ile Pro Glu Leu Gln Val Trp
370                 375                 380

Tyr Thr Lys Leu Gly Lys Pro Ser Glu Arg Tyr Leu Phe Lys Gln Leu
385                 390                 395                 400

Asp Ser Leu Trp Leu Leu Asp Ser Ser Ser Thr Phe Thr Leu Glu Leu
                405                 410                 415

Gln Glu Asp Glu Ile Phe Thr Leu Thr Thr Leu Thr Val Gly Ser Lys
                420                 425                 430

Gly Ser Tyr Pro Leu Pro Pro Lys Ser Glu Pro Phe Pro Gln Ile Tyr
            435                 440                 445

Glu Asp Asp Phe Asp Val Asp Tyr Pro Phe Phe Ser Glu Ala Pro Asn
450                 455                 460

Phe Ala Asp Gln Thr Gly Val Phe Glu Tyr Phe Thr Asn Ile Glu Asp
465                 470                 475                 480

Pro Gly Glu His Arg Phe Thr Leu Arg Gln Val Leu Asn Gln Arg Pro
                485                 490                 495

Ile Thr Trp Ala Ala Asp Ala Tyr Asn Thr Ile Ser Ile Ile Gly Asp
            500                 505                 510

Tyr Lys Trp Ser Asn Leu Thr Val Arg Cys Asp Val Tyr Ile Glu Thr
        515                 520                 525

Pro Glu Lys Gly Val Phe Ile Ala Gly Arg Val Asn Lys Gly Gly
    530                 535                 540

Ile Leu Ile Arg Ser Ala Arg Gly Ile Phe Phe Trp Ile Phe Ala Asn
545                 550                 555                 560

Gly Thr Tyr Arg Val Thr Gly Asp Leu Ala Gly Trp Val Ile Tyr Ala
                565                 570                 575

Leu Gly Arg Val Asp Val Thr Ala Lys Lys Trp Tyr Thr Leu Thr Leu
            580                 585                 590

Ile Ile Lys Gly Arg Leu Ser Ser Gly Met Leu Asn Gly Lys Thr Val
        595                 600                 605

Trp Lys Asn Ile Pro Val Ser Phe Pro Lys Asn Gly Trp Ala Ala Ile
    610                 615                 620

Gly Thr His Ser Phe Glu Phe Ala Gln Phe Asp Asn Phe His Val Glu
625                 630                 635                 640

Ala Thr Arg
```

<210> SEQ ID NO 15
<211> LENGTH: 643
<212> TYPE: PRT
<213> ORGANISM: Artificial
<220> FEATURE:
<223> OTHER INFORMATION: hGALC

<400> SEQUENCE: 15

```
Tyr Val Leu Asp Asp Ser Asp Gly Leu Gly Arg Glu Phe Asp Gly Ile
 1               5                  10                  15

Gly Ala Val Ser Gly Gly Ala Thr Ser Arg Leu Leu Val Asn Tyr
             20                  25                  30

Pro Glu Pro Tyr Arg Ser Gln Ile Leu Asp Tyr Leu Phe Lys Pro Asn
             35                  40                  45

Phe Gly Ala Ser Leu His Ile Leu Lys Val Glu Ile Gly Gly Asp Gly
         50                  55                  60

Gln Thr Thr Asp Gly Thr Glu Pro Ser His Met His Tyr Ala Leu Asp
 65                  70                  75                  80

Glu Asn Tyr Phe Arg Gly Tyr Glu Trp Trp Leu Met Lys Glu Ala Lys
                 85                  90                  95

Lys Arg Asn Pro Asn Ile Thr Leu Ile Gly Leu Pro Trp Ser Phe Pro
            100                 105                 110

Gly Trp Leu Gly Lys Gly Phe Asp Trp Pro Tyr Val Asn Leu Gln Leu
        115                 120                 125

Thr Ala Tyr Tyr Val Val Thr Trp Ile Val Gly Ala Lys Arg Tyr His
    130                 135                 140

Asp Leu Asp Ile Asp Tyr Ile Gly Ile Trp Asn Glu Arg Ser Tyr Asn
145                 150                 155                 160

Ala Asn Tyr Ile Lys Ile Leu Arg Lys Met Leu Asn Tyr Gln Gly Leu
                165                 170                 175

Gln Arg Val Lys Ile Ile Ala Ser Asp Asn Leu Trp Glu Ser Ile Ser
            180                 185                 190

Ala Ser Met Leu Leu Asp Ala Glu Leu Phe Lys Val Val Asp Val Ile
        195                 200                 205

Gly Ala His Tyr Pro Gly Thr His Ser Ala Lys Asp Ala Lys Leu Thr
    210                 215                 220

Gly Lys Lys Leu Trp Ser Ser Glu Asp Phe Ser Thr Leu Asn Ser Asp
225                 230                 235                 240

Met Gly Ala Gly Cys Trp Gly Arg Ile Leu Asn Gln Asn Tyr Ile Asn
                245                 250                 255

Gly Tyr Met Thr Ser Thr Ile Ala Trp Asn Leu Val Ala Ser Tyr Tyr
            260                 265                 270

Glu Gln Leu Pro Tyr Gly Arg Cys Gly Leu Met Thr Ala Gln Glu Pro
        275                 280                 285

Trp Ser Gly His Tyr Val Val Glu Ser Pro Val Trp Val Ser Ala His
    290                 295                 300

Thr Thr Gln Phe Thr Gln Pro Gly Trp Tyr Tyr Leu Lys Thr Val Gly
305                 310                 315                 320

His Leu Glu Lys Gly Gly Ser Tyr Val Ala Leu Thr Asp Gly Leu Gly
                325                 330                 335

Asn Leu Thr Ile Ile Ile Glu Thr Met Ser His Lys His Ser Lys Cys
            340                 345                 350

Ile Arg Pro Phe Leu Pro Tyr Phe Asn Val Ser Gln Gln Phe Ala Thr
        355                 360                 365
```

-continued

Phe Val Leu Lys Gly Ser Phe Ser Glu Ile Pro Glu Leu Gln Val Trp
       370                 375                 380

Tyr Thr Lys Leu Gly Lys Thr Ser Glu Arg Phe Leu Phe Lys Gln Leu
385                 390                 395                 400

Asp Ser Leu Trp Leu Leu Asp Ser Asp Gly Ser Phe Thr Leu Ser Leu
                405                 410                 415

His Glu Asp Glu Leu Phe Thr Leu Thr Thr Leu Thr Thr Gly Arg Lys
            420                 425                 430

Gly Ser Tyr Pro Leu Pro Pro Lys Ser Gln Pro Phe Pro Ser Thr Tyr
        435                 440                 445

Lys Asp Asp Phe Asn Val Asp Tyr Pro Phe Phe Ser Glu Ala Pro Asn
450                 455                 460

Phe Ala Asp Gln Thr Gly Val Phe Glu Tyr Phe Thr Asn Ile Glu Asp
465                 470                 475                 480

Pro Gly Glu His His Phe Thr Leu Arg Gln Val Leu Asn Gln Arg Pro
                485                 490                 495

Ile Thr Trp Ala Ala Asp Ala Ser Asn Thr Ile Ser Ile Ile Gly Asp
            500                 505                 510

Tyr Asn Trp Thr Asn Leu Thr Thr Lys Cys Asp Val Tyr Ile Glu Thr
        515                 520                 525

Pro Asp Thr Gly Gly Val Phe Ile Ala Gly Arg Val Asn Lys Gly Gly
    530                 535                 540

Ile Leu Ile Arg Ser Ala Arg Gly Ile Phe Pro Trp Ile Phe Ala Asn
545                 550                 555                 560

Gly Ser Tyr Arg Val Thr Gly Asp Leu Ala Gly Trp Ile Ile Tyr Ala
                565                 570                 575

Leu Gly Arg Val Glu Val Thr Ala Lys Lys Trp Tyr Thr Leu Thr Leu
            580                 585                 590

Thr Ile Lys Gly His Phe Ala Ser Gly Met Leu Asn Asp Lys Ser Leu
        595                 600                 605

Trp Thr Asp Ile Pro Val Asn Phe Pro Lys Asn Gly Trp Ala Ala Ile
    610                 615                 620

Gly Thr His Ser Phe Glu Phe Ala Gln Phe Asp Asn Phe Leu Val Glu
625                 630                 635                 640

Ala Thr Arg

<210> SEQ ID NO 16
<211> LENGTH: 643
<212> TYPE: PRT
<213> ORGANISM: Macaca mulatta

<400> SEQUENCE: 16

Tyr Val Leu Asp Asp Ser Asp Gly Leu Gly Arg Glu Phe Asp Gly Ile
1               5                   10                  15

Gly Ala Val Ser Gly Gly Ala Thr Ser Arg Leu Leu Val Asn Tyr
            20                  25                  30

Pro Glu Pro Tyr Arg Ser Gln Ile Leu Asp Tyr Leu Phe Lys Pro Asn
        35                  40                  45

Phe Gly Ala Ser Leu His Ile Leu Lys Val Glu Ile Gly Gly Asp Gly
    50                  55                  60

Gln Thr Thr Asp Gly Thr Glu Pro Ser His Met His Tyr Ala Leu Asp
65                  70                  75                  80

Glu Asn Tyr Phe Arg Gly Tyr Glu Trp Trp Leu Met Lys Glu Ala Lys
                85                  90                  95

```
Lys Arg Asn Pro Asn Ile Thr Leu Ile Gly Leu Pro Trp Ser Phe Pro
                100                 105                 110

Gly Trp Leu Gly Lys Gly Phe Asp Trp Pro Tyr Val Asn Leu Gln Leu
            115                 120                 125

Thr Ala Tyr Tyr Val Val Thr Trp Ile Val Gly Ala Lys Arg Tyr His
130                 135                 140

Asp Leu Asp Ile Asp Tyr Ile Gly Ile Trp Asn Glu Arg Ser Tyr Asn
145                 150                 155                 160

Ala Asn Tyr Ile Lys Ile Leu Arg Lys Met Leu Asn Ser Gln Gly Leu
                165                 170                 175

Gln Arg Val Lys Ile Ile Ala Ser Asp Asn Leu Trp Glu Ser Ile Ser
                180                 185                 190

Ala Ala Met Leu Leu Asp Ala Glu Leu Phe Lys Val Val Asp Val Ile
            195                 200                 205

Gly Ala His Tyr Pro Gly Thr His Ser Val Lys Asp Ala Arg Leu Thr
            210                 215                 220

Gly Lys Lys Leu Trp Ser Ser Glu Asp Phe Ser Thr Leu Asn Ser Asp
225                 230                 235                 240

Thr Gly Ala Gly Cys Trp Gly Arg Ile Leu Asn Gln Asn Tyr Val Asn
                245                 250                 255

Gly Tyr Met Thr Ser Thr Ile Ala Trp Asn Leu Val Ala Ser Tyr Tyr
            260                 265                 270

Glu Gln Leu Pro Tyr Gly Arg Cys Gly Leu Met Thr Ala Gln Glu Pro
            275                 280                 285

Trp Ser Gly His Tyr Val Val Glu Ser Pro Val Trp Val Ser Ala His
            290                 295                 300

Thr Thr Gln Phe Thr Gln Pro Gly Trp Tyr Tyr Leu Lys Thr Val Gly
305                 310                 315                 320

His Leu Glu Lys Gly Gly Ser Tyr Val Ala Leu Thr Asp Gly Leu Gly
                325                 330                 335

Asn Leu Thr Ile Ile Ile Glu Thr Met Ser His Lys His Ser Lys Cys
                340                 345                 350

Ile Arg Pro Phe Leu Pro Tyr Phe Asn Val Ser Gln Gln Phe Ala Thr
            355                 360                 365

Phe Val Leu Lys Gly Ser Phe Ser Glu Ile Pro Glu Leu Gln Val Trp
370                 375                 380

Tyr Thr Lys Leu Gly Lys Thr Ser Glu Arg Phe Leu Phe Lys Gln Leu
385                 390                 395                 400

Asp Ser Leu Trp Leu Leu Asp Ser Asn Gly Ser Phe Thr Leu Lys Leu
                405                 410                 415

Gln Glu Asp Glu Leu Phe Thr Leu Thr Thr Leu Thr Thr Gly Arg Lys
            420                 425                 430

Gly Ser Tyr Leu Pro Pro Lys Ser Gln Arg Phe Pro Ser Thr Tyr
            435                 440                 445

Lys Asp Asp Phe Asn Val Asp Tyr Pro Phe Phe Ser Glu Ala Pro Asn
            450                 455                 460

Phe Ala Asp Gln Thr Gly Val Phe Glu Tyr Phe Thr Asn Met Glu Asp
465                 470                 475                 480

Pro Gly Glu His His Phe Thr Leu Arg Gln Val Leu Asn Gln Arg Pro
                485                 490                 495

Ile Thr Trp Ala Ala Asp Ala Ser Asn Thr Ile Ser Ile Ile Gly Asp
            500                 505                 510
```

-continued

```
Tyr Asn Trp Thr Asn Leu Thr Ile Lys Cys Asp Val Tyr Ile Glu Thr
        515                 520                 525

Pro Asp Thr Gly Gly Val Phe Ile Ala Gly Arg Val Asn Lys Gly Gly
    530                 535                 540

Ile Leu Ile Arg Ser Ala Arg Gly Ile Phe Phe Trp Ile Phe Ala Asn
545             550                 555                 560

Gly Ser Tyr Arg Val Thr Gly Asp Leu Ala Gly Trp Ile Ile Tyr Ala
                565                 570                 575

Leu Gly His Val Glu Val Thr Ala Lys Thr Trp Tyr Thr Leu Thr Leu
            580                 585                 590

Thr Ile Lys Gly Arg Phe Ala Ser Gly Met Leu Asn Asp Lys Ser Leu
        595                 600                 605

Trp Thr Asp Ile Pro Val Asn Phe Pro Lys Asn Gly Trp Ala Ala Ile
        610                 615                 620

Gly Thr His Ser Phe Glu Phe Ala Gln Phe Asp Asn Phe His Val Glu
625                 630                 635                 640

Ala Thr Arg
```